(12) United States Patent  
Chapman et al.

(10) Patent No.: US 11,137,409 B2
(45) Date of Patent: Oct. 5, 2021

(54) IDENTIFICATION OF NOVEL DISEASE STATES USING VISCOELASTIC ANALYSIS IN THE PRESENCE OF A THROMBOLYTIC AGENT

(71) Applicant: The Regents of the University of Colorado, a body corporate, Denver, CO (US)

(72) Inventors: Michael P. Chapman, Denver, CO (US); Hunter B. Moore, Denver, CO (US); Eduardo Gonzalez Barreda, Denver, CO (US); Ernest E. Moore, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 442 days.

(21) Appl. No.: 15/524,095

(22) PCT Filed: Nov. 5, 2015

(86) PCT No.: PCT/US2015/059146
§ 371 (c)(1),
(2) Date: May 3, 2017

(87) PCT Pub. No.: WO2016/073668
PCT Pub. Date: May 12, 2016

(65) Prior Publication Data
US 2017/0336423 A1 Nov. 23, 2017

Related U.S. Application Data

(60) Provisional application No. 62/076,386, filed on Nov. 6, 2014.

(51) Int. Cl.
 *G01N 33/86* (2006.01)
 *A61K 38/36* (2006.01)
 *C12Q 1/56* (2006.01)

(52) U.S. Cl.
 CPC ............ *G01N 33/86* (2013.01); *A61K 38/36* (2013.01); *C12Q 1/56* (2013.01); *G01N 2800/224* (2013.01); *G01N 2800/226* (2013.01)

(58) Field of Classification Search
 CPC ............ G01N 2800/226; G01N 33/86; G01N 2800/224; A61K 38/36; C12Q 1/56
 See application file for complete search history.

(56) References Cited

U.S. PATENT DOCUMENTS

| 4,529,614 A | 7/1985 | Burns ............................ 472/2 |
| 4,687,765 A | 8/1987 | Vairel et al. ................... 514/56 |

(Continued)

FOREIGN PATENT DOCUMENTS

| EP | 2741086 A1 | 6/2014 |
| JP | 2011518542 A | 6/2011 |

(Continued)

OTHER PUBLICATIONS

Chapman et al., "Fibrinolysis greater than 3% is the critical value for initiation of antifibrinolytic therapy," *J Trauma Acute Care Surg.*, 75(6), pp. 961-967, Dec. 2013.

(Continued)

*Primary Examiner* — Rebecca M Fritchman
(74) *Attorney, Agent, or Firm* — Wilson Sonsini Goodrich & Rosati

(57) ABSTRACT

In some embodiments, the invention provides methods for detecting an aberrant fibrinolysis condition in a patient. The method includes subjecting a blood sample from the patient to a viscoelastic analysis in the presence of a known amount (Continued)

of a thrombolytic agent, to obtain a coagulation characteristic value of the patient; and comparing the coagulation characteristic value of the patient to a coagulation characteristic value of a healthy individual, the coagulation characteristic value of the healthy individual obtained by subjecting a blood sample from a healthy individual to the viscoelastic analysis in the presence of the known amount of the thrombolytic agent, wherein a difference in the coagulation characteristic value of the patient as compared to the coagulation characteristic value of the healthy individual identifies the patent as having aberrant fibrinolysis. In some embodiments, the invention also provides a container adapted for detecting an aberrant fibrinolysis condition in a blood sample using viscoelastic analysis comprising an interior having a coating comprising a thrombolytic agent.

15 Claims, 38 Drawing Sheets

(56) References Cited

U.S. PATENT DOCUMENTS

| | | | |
|---|---|---|---|
| 4,705,756 | A | 11/1987 | Spillert et al. |
| 4,898,825 | A | 2/1990 | Morii et al. ............... 435/212 |
| 6,472,161 | B1 | 10/2002 | Baugh |
| 7,261,861 | B2 | 8/2007 | Kautzky |
| 7,811,792 | B2 | 10/2010 | Cohen et al. |
| 8,637,320 | B2 | 1/2014 | Schubert et al. |
| 8,772,039 | B2 | 7/2014 | Nadkarni |
| 10,509,512 | B2 | 12/2019 | Kikuchi |
| 2007/0184508 | A1 | 8/2007 | Cohen et al. ............... 435/11 |
| 2008/0268483 | A1 | 10/2008 | Goldenberg et al. |
| 2009/0130645 | A1 | 5/2009 | Schubert et al. ............ 435/2 |
| 2010/0062981 | A1 | 3/2010 | Jeppsson et al. |
| 2010/0318178 | A1 | 12/2010 | Rapaport et al. |
| 2011/0268732 | A1 | 11/2011 | Johansson |
| 2011/0288732 | A1 | 11/2011 | Kuwahara et al. |
| 2012/0301967 | A1 | 11/2012 | Nadkarni |
| 2013/0261171 | A1 | 10/2013 | Hessels et al. |
| 2013/0261177 | A1 | 10/2013 | Johansson et al. |
| 2015/0316565 | A1 | 11/2015 | Chapman et al. |
| 2018/0011116 | A1 | 1/2018 | Chapman |
| 2019/0072570 | A1 | 3/2019 | Chapman |

FOREIGN PATENT DOCUMENTS

| | | |
|---|---|---|
| JP | 2013543491 A | 12/2013 |
| RU | 2517116 C2 | 5/2014 |
| WO | WO-9614581 A1 | 5/1996 |
| WO | WO-2006036744 A2 | 4/2006 |
| WO | WO 2007/047961 | 4/2007 |
| WO | WO 2011/057143 | 5/2011 |
| WO | WO 2012/159021 | 11/2012 |
| WO | WO-2014031253 A1 | 2/2014 |
| WO | WO-2014100378 A1 | 6/2014 |
| WO | WO-2015171116 A1 | 11/2015 |
| WO | WO-2016073668 A1 | 5/2016 |
| WO | WO-2016126849 A1 | 8/2016 |
| WO | WO-2016200765 A1 | 12/2016 |

OTHER PUBLICATIONS

International Searching Authority, International Search Report and Written Opinion, International Application No. PCT/US15/59146, 24 pages, dated Jan. 14, 2016.
Moore et al., "Hyperfibrinolysis, physiologic fibrinolysis, and fibrinolysis shutdown: The spectrum of postinjury fibrinolysis and relevance to antifibrinolytic therapy," J Trauma Acute Care Surg., 77(6), pp. 811-817, Dec. 2014.
Brohi et al. Acute Coagulopathy of Trauma: Hypoperfusion Induces Systemic Anticoagulation and Hyperfibrinolysis. The Journal of Trauma and Acute Care Surgery, vol. 64, Issue 5, pp. 1211-1217, May 2008.
Brohi et al. Acute Coagulopathy of Trauma: Mechanism, Identification and Effect. Current Opinion in Critical Care, vol. 13, Issue 6, pp. 680-685, Dec. 2007.
Brohi et al. Acute Traumatic Coagulopathy: Initiated by Hypoperfusion, Modulated Through the Protein C Pathway? Annals of Surgery, vol. 245, No. 5, pp. 812-818, May 2007.
Chapman, Michael P. "Fibrinolysis Greater than 3% is the Critical value for initiation of antifibrinolytic therapy" Journal of Trauma and Acute Care Surgery, (2013) vol. 75, No. 6, pp. 1-16.
Cohen et al. Critical Role of Activated Protein C in Early Coagulopathy and Later Organ Failure, Infection and Death in Trauma Patients. Annals of Surgery, 255 (2) pp. 379-385, Feb. 2012.
Cohen et al. Towards Hemostatic Resuscitation: The Changing Understanding of Acute Traumatic Biology, Massive Bleeding, and Damage-Control Resuscitation. Surg. Clin. NorthAm., vol. 92, Issue 4. pp. 877-91, Aug. 2012.
Cotton, B., et al., Rapid Thrombelastography Delivers Real-Time Results That Predict Transfusion Within 1 Hour of Admission, The Journal of Trauma: Injury, Infection, and Critical Care, 71, Aug. 2, 2011, pp. 407-441.
Cotton et al. Hyperfibrinolysis at Admission is an Uncommon but Highly Lethal Event Associated with Shock and PreHospital Fluid Administration. Journal of Trauma and Acute Care Surgery, vol. 73, Issue 2, pp. 365-370, Aug. 2012.
David W., et al., "TEG and ROTEM: Technology and clinical applications, American Journal of Hematology, (2014) vol. 89, No. 2, pp. 228-232".
Dekker, Simone Esther et al., Lysis Onset Time as Diagnostic Rotational Thromboelastometry Parameter for Fast Detection of Hyperfibrinolysis, Anesthesiology, vol. 121, No. 1, Jul. 2014, pp. 89-97, XP002778643.
Dunn et al. Acidosis-Induced Coagulopathy. Surg. Forum, 30, pp. 471-473, Jan. 1979.
Eastridge et al. Died of Wounds on the Battlefield: Causation and Implications for Improving Combat Casualty Care. Journal of Trauma, 71 (1 Suppl.): S4-8, Jul. 2011.
EP16747211.7 Extended European Search Report dated Jun. 1, 2018.
Extended European Search Report dated Jan. 24, 2020 for EP Patent Appl. No. 17803282.7.
Extended European Search Report relating to EP Appl. No. 15856414.6 dated Mar. 14, 2018.
Ganter, et al., Coagulation monitoring: current techniques and clinical use of viscoelastic point-of-care coagulation devices. Anesthesia & Analgesia, May 2008;106(5): 1366-1375.
Geier, Bruno et al., Pharmacokinetics of tissue plasminogen activator in an isolated extracorporeal circuit, J. Vascular Surgery, 2001, vol. 33, No. 1, pp. 165-169.
Genet et al., Detection of tPA-lnduced Hyperfibrinolysis in Whole Blood by RapidTED, KaolinTEG, and Functional Fibrinogen TEG in Healthy Individuals, Clinical and Applied Thrombosis/Hemostasis 18(6) 638-644 (2012).
Gonzalez, E., Differentiation of Enzymatic from Platelet Hypercoagulability Using the Novel Thromboelastography Parameter Delta J. of Surgical Research, 103, Sep. 1, 2010, pp. 96-1010.
Gonzalez et al. Fresh Frozen Plasma Should be Given Earlier to Patients Requiring Massive Transfusion. Journal of Trauma Injury, Infection, and Critical Care. 62(1), pp. 112-119, 2007.
Hirsh et al. Management of deep vein thrombosis and pulmonary embolism. A statement for healthcare professionals. Council on Thrombosis (in consultation with the Council on Cardiovascular Radiology), American Heart Association. Circulation. Jun. 15, 1996;93(12):2212-45.
Holcomb, et al., Admission rapid thrombelastography can replace conventional coagulation tests in the emergency department. Ann Surg, 2012;256: 476-486.
International Preliminary Report on Patentability dated Nov. 22, 2018 for PCT/US2017/32226.
International Search Report and Written Opinion dated Jun. 30, 2016 for International PCT Patent Application No. PCT/US2016/016412.

(56) References Cited

OTHER PUBLICATIONS

International Search Report and Written Opinion dated Aug. 23, 2017 for International PCT Patent Application No. PCT/US2017/032226.
International Search Report and Written Opinion dated Aug. 26, 2016 for International PCT Patent Application No. PCT/US2016/036143.
International Search Report and Written Opinion dated Jan. 14, 2016, for PCT/US15/59146.
International Search Report and Written Opinion dated Jun. 30, 2016 for PCT/US2016/016412.
Johansson, et al., Current management of massive hemorrhage in trauma. Scandinavian Journal of Trauma, resuscitation and emergency medicine, 2012;20(47): 1-10.
Johnson et al. Effect of Blood Products Transfusion on the development of Post Injury Multiple Organ Failure. Achieves of Surgery, 145(10), pp. 973-977, 2010.
Kashuk et al. Major Abdominal Vascular Trauma-A Unified Approach, Journal of Trauma, 22(8), pp. 672-679, Aug. 1982.
Kashuk et al. Post Injury Life Threatening Coagulopathy: Is 1:1 Fresh Frozen Plasma: Packed Red Blood Cells The Answer? Journal of Trauma, Infection, and Critical Care, 65(2), pp. 261-271,2008.
Meesters, M, et al., Whole blood coagulation thrombelastographic profiles employing minimal tissue factor activation, J. Thrombosis and haemostasis, 1, Mar. 3, 2003, pp. 551-558. (Year 2003).
Moore et al. Blood Transfusion: An Independent Risk Factor for Post Injury Multiple Organ Failure. Archives of Surgery, 132(6), pp. 620-624, Jun. 1997.
Neal et al. Massive Transfusion: An Evidence-Based Review of Recent Developments. Archives of Surgery, 147(6), pp. 563-571, 2012.
Non-Final Office Action dated Oct. 25, 2019 for U.S. Appl. No. 15/524,095.
Non-Final Office Action dated Jul. 23, 2020, for U.S. Appl. No. 16/300,491.
Non-Final Office Action dated Jun. 22, 2020, for U.S. Appl. No. 15/580,968.
Pham, et al., Update on massive transfusion. British journal of anaesthesia. 2013;111 (S1): 171-782.
Semon et al. Thromboelastography (TEG) in Trauma. Department of Surgical Education, Orlando Medical Center, 7 pages, Dec. 2014.
Sorensen, B. et al., Whole blood coagulation thrombelastograph profiles employing minimal tissue factor activation, J. Thrombosis and Haemostasis, 1, Mar. 3, 2003, pp. 551-558.
Watson et al. Fresh Frozen Plasma is Independently Associated with a Higher Risk of Multiple Organ Failure and Acute Respiratory Distress Syndrome. Journal of Trauma, 67(2), pp. 221-227, I Aug. 2009.
Whiting, David et al., TEG and ROTEM: Technology and clinical applications, American Journal of Hematology, vol. 89, No. 2, Feb. 2014, pp. 228-232, XP002778641.

PAI-1 is the Cognate Inhibitor of tPA

PAI-1 is the Cognate Inhibitor of tPA

PAI-1 is the Cognate Inhibitor of tPA aPC Proposed as Primer Mover in Systematic Hyperfibrinolysis aPC Proposed as Primer Mover in Systematic Hyperfibrinolysis aPC Proposed as Primer Mover in Systematic Hyperfibrinolysis Principle Components of TIC:
Hyperfibrinolysis is Independent of Soluble Phase Coagulopathy

| | PC 1 | PC 2 | PC 3 |
|---|---|---|---|
| Eigenvalue | 5.1 | 1.4 | 1.0 |
| % Variance | 63% | 17% | 13% |
| ACT | -30 | 90* | 6 |
| K | -95* | 15 | -4 |
| angle | -92* | -26 | 5 |
| MA | -95* | -15 | -10 |
| LY30 | -4 | 0 | 99* |
| TMRTG | -13 | 95* | -5 |
| MRTG | 94* | -23 | 3 |
| TTG | 94* | -14 | -16 |

IDENTIFICATION OF NOVEL DISEASE STATES USING VISCOELASTIC ANALYSIS IN THE PRESENCE OF A THROMBOLYTIC AGENT

CROSS REFERENCE TO RELATED APPLICATION

This Application is a U.S. national stage entry under 35 USC § 371 of PCT/US2015/059146 filed Nov. 5, 2015 which itself claims priority to U.S. provisional application No. 62/076,386 filed Nov. 6, 2014, the entire contents of each of which is hereby incorporated by reference.

STATEMENT REGARDING FEDERAL SPONSORED RESEARCH OR DEVELOPMENT

This invention was made with government support under Grant Nos. T32-GM008315, P50-GM49222, and UMHL120877 awarded by the National Institutes of Health, and under DoD contract no. W81XWH1220028. The government has certain rights in the invention.

BACKGROUND

The present invention relates to the fields of medicine and surgery and emergent and chronic critical care for traumatic injury and sequelae of traumatic injury.

Following traumatic injury, the human body's normal response to tissue injury is to produce blood clots to prevent the loss of blood from damaged vessels. The process of appropriate blood clot formation is called coagulation and it is an essential component of hemostasis: the maintenance of the integrity of the vasculature and the containment of blood flow within these vessels. However, in up to one-third of severely injured trauma patients a pathological failure of coagulation occurs, known as "trauma induced coagulopathy" or "TIC". TIC is due to physiologic exhaustion, consumption of the component factors of blood clotting and other less well understood causes. The risk of death is up to four-times higher in patients with TIC than similarly injured patients with normal coagulation.

Thus, it would be useful to find methods and reagents to identify and treat patients with trauma induced coagulopathy.

SUMMARY OF THE EMBODIMENTS

The invention provides methods and reagents to rapidly and accurately detect and treat patients with traumatic induced coagulopathy or "TIC". In some embodiments, the invention provides methods and reagents to rapidly and accurately detect and treat patients with the newly defined disorders fibrinolysis shutdown and latent hyperfibrinolysis.

In a first aspect, the invention provides a method for detecting aberrant fibrinolysis in a patient, comprising (a) subjecting a blood sample from the patient to a viscoelastic analysis in the presence of a known amount of a thrombolytic agent, to obtain a coagulation characteristic value of the patient; and (b) comparing the coagulation characteristic value of the patient to a coagulation characteristic value of a healthy individual or to an averaged coagulation characteristic value of a group of healthy individuals, the coagulation characteristic value of the healthy individual obtained by subjecting a blood sample from a healthy individual to the viscoelastic analysis in the presence of the known amount of the thrombolytic agent and the averaged coagulation characteristic value of the group of healthy individuals obtained by subjecting blood samples from healthy individuals to the viscoelastic analysis in the presence of the known amount of the thrombolytic agent, wherein a difference in the coagulation characteristic value of the patient as compared to the coagulation characteristic value of the healthy individual or to the averaged coagulation characteristic value of the group of healthy individuals identifies the patent as having aberrant fibrinolysis. In some embodiments, the thrombolytic agent is human single chain tissue plasminogen activator (tPA). In some embodiments, the thrombolytic agent is tPA, human single chain tPA, human double chain tPA, tPA from a non-human mammalian species, alteplase, reteplase, tenecteplase, anistreplase, serokinase, streptokinase, urokinase, kallikrein, and/or a combination of one or more of the foregoing.

In some embodiments, the known amount of a thrombolytic agent is a low amount of thrombolytic agent and wherein the aberrant fibrinolysis condition is hyperfibrinolysis (e.g., latent fibrinolysis). In some embodiments, the low amount is between about 1 ng/ml to about 100 ng/ml thrombolytic agent. In some embodiments, the low amount is between about 10 ng/ml to about 90 ng/ml thrombolytic agent. In some embodiments, the thrombolytic agent is human single chain tPA and the low amount is about 75 ng/ml human single chain tPA. In some embodiments, an increase in the coagulation characteristic value of the patient as compared to the coagulation characteristic value of the healthy individual or to the averaged coagulation characteristic value of the group of healthy individuals identifies the patient as having hyperfibrinolysis (e.g., latent hyperfibrinolysis).

In some embodiments, the known amount of a thrombolytic agent is a high amount of thrombolytic agent and wherein the aberrant fibrinolysis condition is fibrinolysis shutdown. In some embodiments, the high amount is between about 110 ng/ml to about 1200 ng/ml thrombolytic agent. In some embodiments, the high amount is between about 130 ng/ml to about 1000 ng/ml thrombolytic agent. In some embodiments, the thrombolytic agent is human single chain tPA and the high amount is about 150 ng/ml human single chain tPA. In some embodiments, a decrease in the coagulation characteristic value of the patient as compared to the coagulation characteristic value of the healthy individual or to the averaged coagulation characteristic value of the group of healthy individuals identifies the patient as having fibrinolysis shutdown.

In another aspect, the invention provides a method for detecting hyperfibrinolysis (e.g., latent fibrinolysis) or fibrinolysis shutdown in a patient, the method comprising (a) subjecting a first blood sample from the patient to a viscoelastic analysis in the presence of a low amount of a thrombolytic agent, to obtain a low coagulation characteristic value of the patient; (b) subjecting a second blood sample from the patient to a viscoelastic analysis in the presence of a high amount of a thrombolytic agent, to obtain a high coagulation characteristic value of the patient; (c) comparing the low coagulation characteristic value of the patient to a low coagulation characteristic value of a healthy individual or an averaged low coagulation characteristic value of a group of healthy individuals, the low coagulation characteristic value of the healthy individual obtained by subjecting a blood sample from a healthy individual to the viscoelastic analysis in the presence of the low amount of the thrombolytic agent and the averaged low coagulation characteristic value of the group of healthy individuals obtained by subjecting blood samples from healthy individuals to the viscoelastic analysis in the presence of the low amount of the thrombolytic agent, and (d) comparing the high coagulation characteristic value of the patient to a high coagulation characteristic value of a healthy individual, the high coagulation characteristic value of the healthy individual obtained by subjecting a blood sample from a healthy individual to the viscoelastic analysis in the presence of the high amount of the thrombolytic agent, wherein a difference in the low coagulation characteristic value of the patient as compared to the low coagulation characteristic value of the healthy individual or to the averaged low coagulation characteristic value of the group of healthy individuals identifies the patent as having hyperfibrinolysis (e.g., latent hyperfibrinolysis) and wherein a difference in the high coagulation characteristic value of the patient as compared to the high coagulation characteristic value of the healthy individual or to the averaged high coagulation characteristic value of the group of healthy individuals identifies the patent as having fibrinolysis shutdown. In some embodiments, an increase in the low coagulation characteristic value of the patient as compared to the low coagulation characteristic value of the healthy individual or to the averaged low coagulation characteristic value of the group of healthy individuals identifies the patient as having hyperfibrinolysis (e.g., latent hyperfibrinolysis). In some embodiments, a decrease in the high coagulation characteristic value of the patient as compared to the high coagulation characteristic value of the healthy individual or to the averaged high coagulation characteristic value of the group of healthy individuals identifies the patient as having fibrinolysis shutdown.

In some embodiments, the thrombolytic agent is human single chain tissue plasminogen activator (tPA). In some embodiments, the thrombolytic agent is tPA, human double chain tPA, tPA from a non-human mammalian species, alteplase, reteplase, tenecteplase, anistreplase, serokinase, streptokinase, urokinase, and/or kallikrein.

In various embodiments of all of the aspects of the invention, the coagulation characteristic value (e.g., low, high, averaged, averaged low, or averaged high) is an LY30 value or an LI30 value.

In various embodiments, the viscoelastic analysis is performed using a container containing the sample on an interior of the container. In various embodiments, the viscoelastic analysis is performed using the container and a pin, wherein the pin moves relative to the container. In various embodiments, the viscoelastic analysis is performed using the container and a pin, wherein the container moves relative to the pin. In various embodiments, the container lacks a bottom surface.

In various embodiments, the patient is a human or a non-human animal. In various embodiments, the patient has or is undergoing a condition such as surgery, a disease condition, a critical illness, trauma, bleeding, and/or a thromboembolic event.

In various embodiments, the patient identified as having hyperfibrinolysis (e.g., latent hyperfibrinolysis) is administered a therapeutically relevant amount of a therapeutic agent that strengthens a blood clot or slows the dissolution of a blood clot. Non-limiting therapeutic agents that strengthen a blood clot or slows the dissolution of a blood clot include an antifibrinolytic agent (e.g., tranexamic acid, aminocaproic acid, or aprotinin), whole blood, blood plasma, cryoprecipitate, factor XIII, fibrinogen, a combination of one or more of the foregoing, and/or other specific clotting factor concentrates. In some embodiments, the therapeutically relevant amount of the therapeutic agent that strengthens a blood clot or slows the dissolution of a blood clot is determined based on the coagulation characteristic value of the patient.

In various embodiments, the patient identified as having fibrinolysis shutdown is administered a therapeutically relevant amount of a therapeutic agent that weakens a blood clot or speeds the dissolution of a blood clot. Non-limiting therapeutic agents that weaken a blood clot or speeds the dissolution of a blood clot include aspirin, heparin, clopidogrel, warfarin, a direct thrombin inhibitor, a Factor Xa inhibitor, tPA, an anticoagulant, a thrombolytic agent, an antifibrinogen agent, an anti-Factor XIII agent, a glycoprotein IIb/IIIa inhibitor, an antiplatelet agent and/or a combination of one or more of the foregoing. In some embodiments, the therapeutically relevant amount of the therapeutic agent that weakens a blood clot or speeds the dissolution of a blood clot is determined based on the coagulation characteristic value of the patient.

In another aspect, the invention provides a container adapted for detecting hyperfibrinolysis (e.g., latent hyerfibrinolysis) in a blood sample using viscoelastic analysis comprising an interior having a coating comprising a low amount of a thrombolytic agent. In some embodiments, the thrombolytic agent is human single chain tissue plasminogen activator (tPA). In some embodiments, the low amount is between about 1 ng/ml to about 100 ng/ml thrombolytic agent, or between about 10 ng/ml to about 90 ng/ml thrombolytic agent. In some embodiments, the container lacks a bottom surface. In some embodiments, the container further comprises a stabilization agent (e.g., EDTA or a surfactant) to stabilize the thrombolytic agent.

In another aspect, the invention provides a container adapted for detecting fibrinolytic shutdown in a blood sample using viscoelastic analysis comprising an interior having a coating comprising a high amount of a thrombolytic agent. In some embodiments, the thrombolytic agent is human single chain tissue plasminogen activator (tPA). In some embodiments, the high amount is between about 110 ng/ml to about 1200 ng/ml thrombolytic agent, or between about 150 ng/ml to about 1000 ng/ml thrombolytic agent. In some embodiments, the container lacks a bottom surface. In some embodiments, the container further comprises a stabilization agent (e.g., EDTA) to stabilize the thrombolytic agent.

In another aspect, the invention provides a kit comprising a first container adapted for detecting hyperfibrinolysis (e.g., latent hyerfibrinolysis) in a blood sample using viscoelastic analysis comprising an interior having a coating comprising a low amount of a thrombolytic agent, a second container adapted for detecting fibrinolytic shutdown in a blood sample using viscoelastic analysis comprising an interior having a coating comprising a high amount of a thrombolytic agent, and instructions for using the first and second container in a viscoelastic analysis to identify hyperfibrinolysis and/or fibrinolysis shutdown in a blood sample. In some embodiments, the containers lack a bottom surface.

In yet another aspect, the invention provides a cartridge comprising multiple containers for detecting aberrant fibrinolysis in a blood sample, wherein at least one of the containers comprises an interior having a coating comprising a low amount of a thrombolytic agent and at least one container comprises an interior having a coating comprising a high amount of the thrombolytic agent. In some embodiments, the thrombolytic agent is human single chain tissue plasminogen activator (tPA). In some embodiments, the high amount is between about 110 ng/ml to about 1200 ng/ml thrombolytic agent, or between about 150 ng/ml to about 1000 ng/ml thrombolytic agent. In some embodiments, the low amount is between about 1 ng/ml to about 100 ng/ml thrombolytic agent, or between about 10 ng/ml to about 90 ng/ml thrombolytic agent. In some embodiments, the containers lack a bottom surface. In some embodiments, the containers further comprise a stabilization agent (e.g., EDTA) to stabilize the thrombolytic agent.

BRIEF DESCRIPTION OF THE DRAWINGS

The present patent or application file contains at least one drawing executed in color. Copies of this patent with color drawing(s) will be provided by the Patent and Trademark Office upon request and payment of necessary fee.

The foregoing features of embodiments will be more readily understood by reference to the following detailed description, taken with reference to the accompanying drawings, in which:

In FIGS. 6A and 6B, CT indicates clotting time, CFT indicates clot formation time, alpha is the alpha-angle, lambda-angle is the lysis rate, MCF is the maximum clot firmness, LI130 is the lysis index 30 minutes after CT, and ML is maximum lysis.

As shown in FIG. 13A, in the presence of the low dose (e.g., 75 ng/ml) of tPA, the blood samples of most healthy volunteers had LY30 values of 5 or 10. In FIG. 13B, in the presence the high dose (e.g., 150 ng/ml) of tPA, the blood samples of most healthy volunteers had LY30 values of between 50 and 70.

FIG. 38 is the same as that depicted in FIG. 3 above. Over 60% of severely injured trauma patients exhibit fibrinolysis shutdown while fewer than 20% exhibit hyperfibrinolysis.

DETAILED DESCRIPTION OF SPECIFIC EMBODIMENTS

The invention stems, in part, from the discovery that latent hyperfibrinolysis and fibrinolysis shutdown exist, and that these two disease conditions can be detected. Thus, in some embodiments, the invention provides methods and reagents (e.g., cups) for detecting latent hyperfibrinolysis and/or fibrinolysis shutdown. The publications (including patent publications), web sites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Hemostasis is a tightly regulated, extremely complex process involving many interacting factors, which include coagulation and fibrinolytic proteins, activators, inhibitors and cellular elements, such as platelet cytoskeleton, platelet cytoplasmic granules and platelet cell surfaces, that controls bleeding in the body of an individual (e.g., a human individual). Hemostasis includes and comprises the balance between two processes: (1) the coagulation process, namely blood coagulation by formation of a fibrin-containing blood clot, and (2) the fibrinolytic process, namely the process involved in the breakdown of that clot, for example, by activation of plasmin to dissolve the fibrin mesh holding the clot together.

In the body, circulating blood remains fluid under normal conditions, but forms localized clots when the integrity of the vascular system is breeched. Trauma, infection, and inflammation all activate the blood's clotting system, which depends on the interaction of enzymatic proteins in a clotting cascade (e.g., clotting factors such as Factor VII or Factor IX), activated platelets, and the damaged vascular endothelium. These three elements work in concert to plug defects in the broken blood vessels.

Figure 1A:
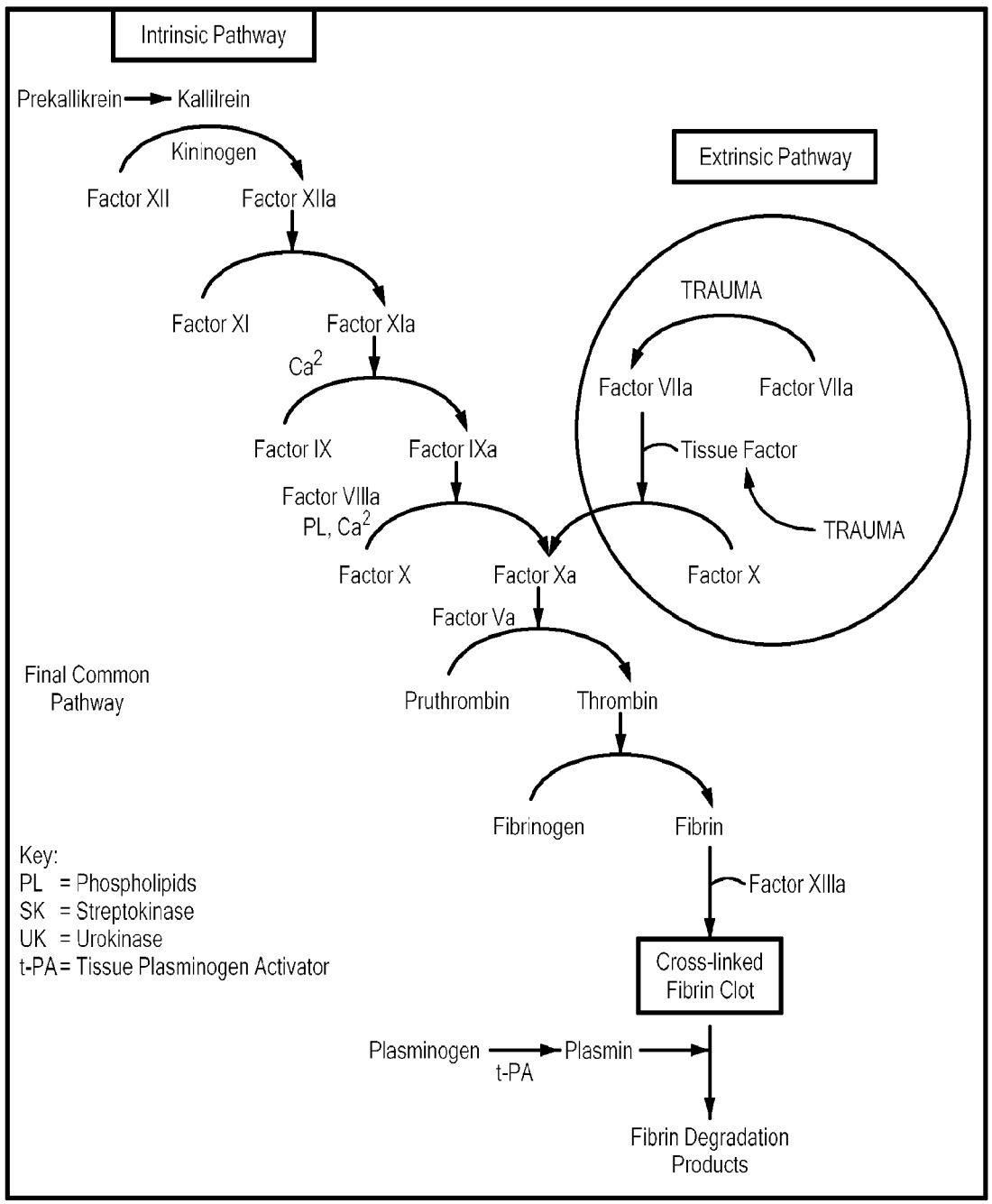
FIGS. 1A and 1B are schematic diagrams showing the clotting cascade that leads eventually to the formation of the fibrin clot made of cross-linked fibrin (FIG. 1A) and the breakdown of the clot during fibrinolysis (FIG. 1B). Activation of plasminogen by tPA produces plasmin which degrades the fibrin into fibrin degradation products.

A blood clot (also called a thrombus) forms during hemostasis (see FIG. 1A). A blood clot needs to be of sufficient strength to resist dislodgement by circulating blood or mechanical movement. If a particular clotting factor is dysfunctional or absent, as in hemophilia, an insufficient amount of fibrin forms. Ultimately, reduced fibrin formation or platelet aggregation results in clots of inadequate tensile strength. This hypocoagulable state makes the patient prone to bleeding. Conversely, injury, immobility, inflammation, infection, cancer, or genetic disorders lead to hypercoagulability and, potentially, to thrombosis (i.e., blood clot) formation, exemplified by deep-vein thromboses, pulmonary emboli, and arterial occlusions such as stroke and myocardial infarction. It is also thought that microvascular thrombi and vasoocclusive disease of small vessels is a significant contributor to multiple organ failure (MOF) is critically ill patients with a variety of underlying disease processes.

Figure 1B:
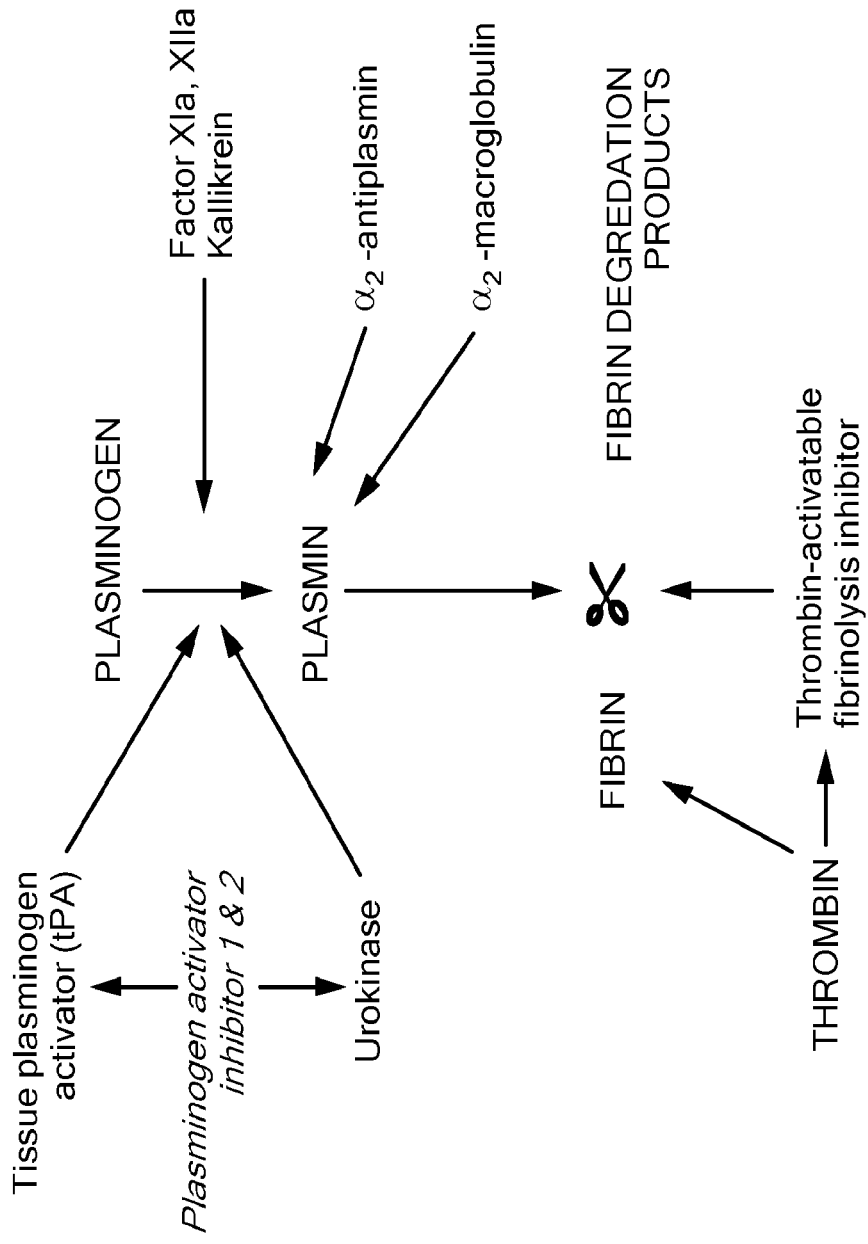

The precursor of plasmin, plasminogen, is zymogen that is incorporated into a blood clot (see FIG. 1B). Tissue plasminogen activator (tPA) and urokinase are serine proteases that are able to convert the plasminogen in the blood clot into plasmin, thus activating it and allowing fibrinolysis to occur. Fibrinolysis, namely the process of breaking down blood clots so that they do not become problematic, is a normal biological process. Normally, tPA is released very slowly into the blood by the damaged endothelium of blood vessels. As a result, after bleeding is stopped, the clot is broken down as the inactive zymogen plasminogen in the clot is activated to become plasmin, which acts to break down the fibrin mesh holding the clot together. The resulting fragments, called fibrin degradation products (FDPs), are then cleared by other enzymes, or by the kidney and liver.

The principal inhibitor of tissue plasminogen activator (tPA) and urokinase is plasminogen activator inhibitor-1 (PAI-1) (see FIG. 1B). PAI-1 is a serine protease inhibitor (serpin) encoded by the PM-1 gene SERPINE1, located on chromosome 7 (7q21.3-q22) in humans. PM-1 is mainly produced by the endothelium (cells lining blood vessels), but is also secreted by other tissue types, such as adipose tissue. By inhibiting tPA and urokinase, PM-1 is an inhibitor of fibrinolysis. The role of PAI-1 in fibrinolysis is depicted in FIG. 1B. Note that there are numerous other inhibitors of the fibrinolytic enzyme system, including PM-2 and 3, TAFI, alpha 2-antiplasmin, alph-2 macroglobulin and others. However, the principal inhibitor of tPA and urokinase is PM-1.

In normal, healthy individuals (e.g., male and female humans between 14 and 44 years of age or between 20 and 40 years of age), the blood concentrations of PM-1 and tPA exist in a balance, where there is slightly more tPA than PM-1. Thus, a "healthy individual" is defined a healthy patient. For example, if the patient is a human, a healthy human individual is between the ages of 14 to 44, who has a normal (i e, uninjured) blood concentration of tPA that is 1%, or 2%, or 5%, or 10% higher than the normal (i.e., uninjured) blood concentration of PM-1.

In some embodiments, the patient is a non-human animal, such as a mammal, bird, reptile, or fish. Accordingly, the patient may be a non-human primate (e.g., chimpanzee, baboon), a cat, dog, cow, pig, sheep, chicken, turkey, llama, elephant, laboratory animal (e.g., rat, mouse, guinea pig, zebrafish), exotic animal (e.g., tiger, lion, komodo dragon, zebra, giraffe, wolf). In some embodiments, the patient is a mammal.

A blood sample from a healthy individual will have little or no fibrinolysis response to a low amount of a thrombolytic agent such as tPA, and will have a fibrinolysis response to a high amount of the thrombolytic agent.

In contrast, by an "apparently healthy individual" is meant that an individual (e.g., a male and female human between 14 and 44 years of age or between 20 and 40 years of age) when uninjured appears to be normal (e.g., the apparently healthy individual does not have haemophilia), but when that individual is injured, bleeding (e.g., undergoing surgery) or critically ill, that individual's PM-1 and tPA concentrations shift either too much to the PM-1 side (i.e., too much PM-1 compared to tPA) or too much to the tPA side (e.g., too much tPA compared to PM-1), and the apparently healthy individual can have aberrant fibrinolysis (e.g., latent hyperfibrinolysis or fibrinolysis shutdown). Of course, since most male and female humans who are not critically ill, bleeding, or injured do not routinely have their blood concentrations of PAI-1 and tPA measured, prior to some embodiments of the present invention, it was impossible to distinguish the apparently healthy individuals from the healthy individuals. In some embodiments, the invention allows rapid identification of such apparently healthy individuals enables the medical practitioner to triage such individuals with greater urgency for treatment than would otherwise be afforded a healthy individual.

The invention stems, in part, from the discovery that if, during or shortly after an injury (which includes, for example, an accidental injury such as a car accident, or a purposeful injury, such as elective surgery), the tPA to PM-1 ratio in an apparently healthy individual starts changing, that apparently healthy individual may have an aberrant fibrinolysis condition such as latent hyperfibrinolysis or fibrinolysis shutdown. If the ratio shifts to more tPA than normal, that apparently healthy individual may have latent hyperfibrinolysis. If the ratio shifts to more PM-1 in that ratio, that apparently healthy individual may have fibrinolysis shutdown.

As used herein, by "aberrant fibrinolysis" is meant a disease condition in which the fibrinolysis prong of hemostasis is not normal. In some embodiments, the aberrant fibrinolysis is trauma induced coagulopathy or "TIC".

Fibrinolysis, as discussed above, is the breakdown of a blood clot. This is accomplished by the activation of inactive plasminogen zymogen into active plasmin. Plasmin will then break down the fibrin mesh holding a blood clot together. As shown in FIG. 1B, multiple agents are able to activate plasminogen into active plasmin. These agents as shown in FIG. 1B include Factor XIa, Factor XIIa, Kallikrein, tissue plasminogen activator (tPA) (including human single chain tPA and human double chain tPA), streptokinase, and urokinase. Additional agents that are able to active plasminogen into active plasmin include, without limitation, urkokinase plasminogen activator (uPA). The conversion of plasminogen to plasmin involves the cleavage of the peptide bond between Arg-561 and Val-562 in plasminogen.

A particularly dangerous aspect of TIC is hyperfibrinolysis. In this condition, the fibrinolytic system (which is usually responsible for the maintenance of blood flow by breaking down blood clots after an injury has healed) is upregulated in a pathological manner and destroys the necessary blood clots which form after injury. This condition is associated with a mortality rate in excess of 60%. While treatable, this condition occasionally presents in a particularly dangerous occult or latent form, which is not detectable by existing laboratory tests. Patients with latent hyperfibrinolysis will be well appearing but are apt to decompensate unexpectedly and dramatically, bleed massively and frequently die, in part due to the fact that their degree of acuity is underestimated by the treating physician. In some embodiments, the invention allows the detection and/or diagnosis of latent hyperfibrinolysis.

Another occult condition which can occur in trauma patients is essentially the reverse of hyperfibrinolysis: fibrinolysis shutdown. This condition of severe impairment of the fibrinolytic system is present in more than half of all severely injured trauma patients as well as in patients with other medical and surgical conditions including kidney disease. Fibrinolysis shutdown is also not detectable by existing clinical laboratory tests. In some embodiments, the invention also provides methods for detecting and/or diagnosing fibrinolysis shutdown.

As used herein, by "latent hyperfibrinolysis" (which is sometimes referred to as "occult hyperfibrinolysis") is meant a type of aberrant fibrinolysis disease condition in which a patient (e.g., a human patient) with an injury (e.g., during surgery or following a traumatic injury) initially appears stable but then abruptly begins to bleed heavily either internally or externally due to overly rapid breakdown of blood clots. In latent hyperfibrinolysis, thus, the first part of hemostasis, namely the formation of blood clots or the coagulation process, is normal. However, the breakdown of the blood clot (i.e., the fibrinolysis part of hemostasis) is abnormal. In latent hyperfibrinolysis, too much plasminogen is broken down into plasmin by too much tissue plasminogen activator. In other words, the ratio of tPA to PM-1 shifts to too much tPA in latent hyperfibrinolysis.

Figure 2:
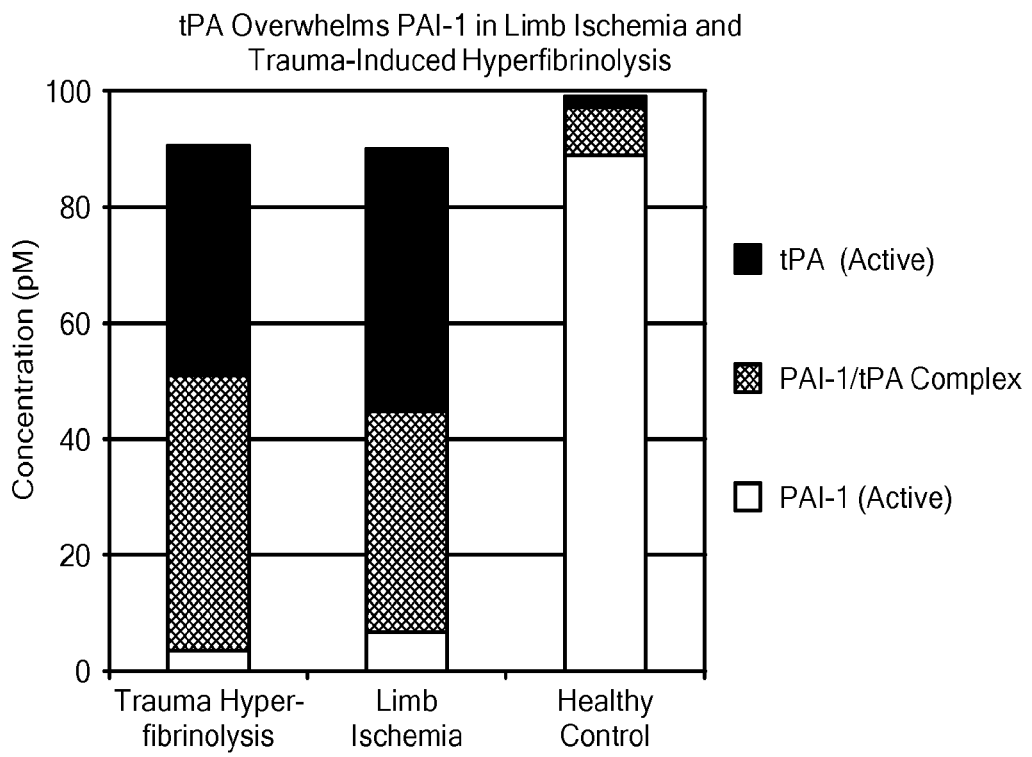
FIG. 2 is a bar graph showing the concentrations of tissue plasminogen activator (tPA) (black), plasminogen activator inhibitor 1 (PAI-1)(light gray) and complexes of tPA and PM-1 (dark gray) in trauma induced hyperfibrinolysis patients (left bar), limb ischemia patients (middle bar) and healthy individuals (right bar).

Note that trauma induced hyperfibrinolysis can also skew this ratio. For example, as shown in FIG. 2, in patients with limb ischemia or with trauma induced hyperfibrinolysis, tPA concentrations overwhelm the PM-1 concentration, thereby shifting the ratio to too much tPA. This results in the clot breaking down too rapidly; hence hyperfibrinolysis results.

As used herein by "fibrinolysis shutdown" is meant a type of aberrant fibrinolysis disease condition in which a blood clot in a patient (e.g., formed after a traumatic injury) is delayed in breaking down. In other words, fibrinolysis shutdown is an extreme form of fibrinolysis resistance that may occur in some patients where blood clots cannot be broken down properly, potentially resulting in organ failure and thromboembolic events. In fibrinolysis shutdown, while the coagulation process of hemostasis is normal, the fibrinolysis process is abnormal. In fibrinolysis shutdown, too little plasminogen is broken down into plasmin by too much PM-1. In other words, the ratio of tPA to PM-1 shifts to too much PM-1 in fibrinolysis shutdown. Fibrinolysis shutdown results in thrombosis, i.e., the formation of thrombuses (i.e., blood clots). The presence a thrombus can reduce blood flow to a tissue, causing hypoxia or anoxia, which can result in tissue death and organ failure. If part of the thrombus breaks off and migrates through the body (e.g., via the blood stream), the migrating thrombus is called an embolus. Where that embolus eventually lodges is capable of clogging blood vessels and killing the tissues and organs that are supplied by the clogged blood vessel.

Because of the difficulty in detecting latent hyperfibrinolysis and fibrinolysis shutdown, the mortality rates from these two conditions is high. Most of our understanding of disorders of fibrinolysis comes two distinct populations of surgical patients: traumatically injured patients and those undergoing liver transplantation. It has been known since the 1960s that patients undergoing liver transplant have a profound upregulation of their fibrinolytic system during the anhepatic phase of surgery and that this hyperfibrinolytic state puts them at risk for massive coagulopathic hemorrhage. Similarly, a proportion of severely injured trauma patients (roughly 20%) will present with hyperfibrinolysis and are at markedly increased risk of death from bleeding, with a roughly 50%-60% mortality or about 4-times the expected rate of death in similarly injured patients without hyperfibrinolysis.

We have recently come to recognize another pathological entity with respect to the fibrinolytic system: fibrinolysis shutdown. While less immediately lethal than hyperfibrinolysis, fibrinolysis shutdown puts patients at greater risk for vasocclusive events (i.e. venous thromboembolism) and multiple organ failure from microvascular thrombosis. Moreover, fibrinolysis shutdown is a far more common phenomenon than hyperfibrinolysis, effecting over 60% of severely injured patients.

Figure 3:
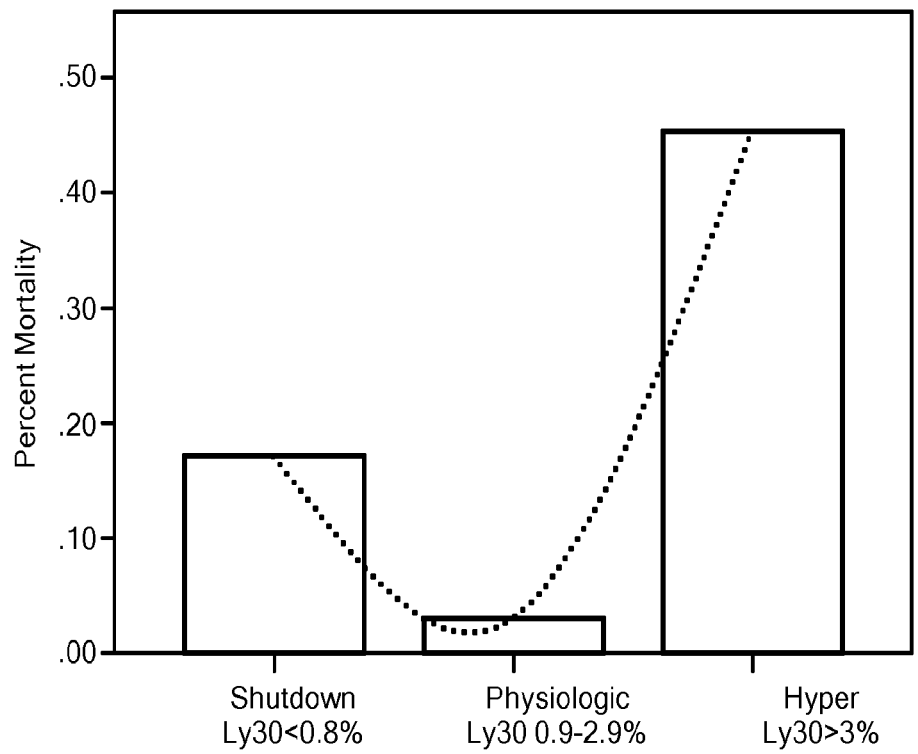
FIG. 3 is a bar graph showing the mortality percentages of patients with fibrinolysis shutdown (left bar; in this figure, with an LY30 of less than 0.8%), physiologically normal levels of fibrinolysis (middle bar; in this figure, with an LY30 of between 0.9% to 2.9%), and hyperfibrinolysis (right bar; in this figure, with a LY30 of greater than 3%) from all causes within 28 days following injury.
Figure 38:
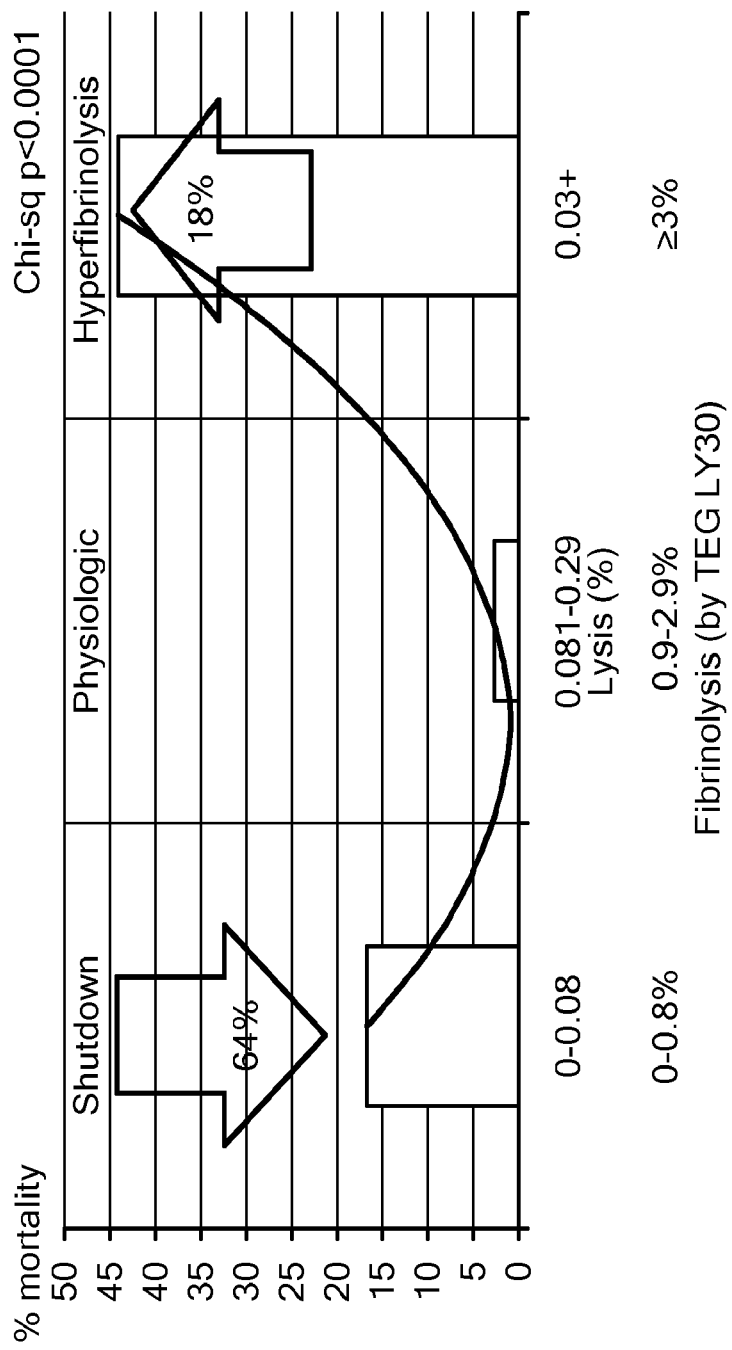
FIG. 38 is a bar graph showing the spectrum of fibrinolysis in trauma patients. Note that data in this

Hyperfibrinolysis and fibrinolysis shutdown are thusdangerous syndromes associated with an increased mortality rate. As shown in FIG. 3 (and in FIG. 38), the all-cause mortality rate of patients with fibrinolysis shutdown is 18% within 28 days of injury and the all-cause mortality rate of patients with latent fibrinolysis is 45% within 28 days of injury. In contrast, only about 2% of the patients who die of all causes within 28 days of injury have physiologically normal hemostasis. In some embodiments, if the patients are treated (e.g., prophylactically) with a therapeutically relevant amount of a therapeutic agent that strengthens a blood clot or slows the dissolution of a blood clot, such as the antifibrinolytic agent tranexamic acid (TXA), the number of mortalities due to latent hyperfibrinolysis may be reduced.

Hence, it is clear that some patients (namely those with hyperfibrinolysis) will benefit from prophylactic treatment with a therapeutic agent that strengthens a blood clot or slows the dissolution of a blood clot, such as an antifibrinolytic agent (e.g., TXA). However, a therapeutic agent that strengthens a blood clot or slows the dissolution of a blood clot cannot be uniformly given to all trauma patients in the emergency room because if the patient has fibrinolysis shutdown, "treatment" with TXA is actually not a treatment at all, but rather results in a worse outcome for these patients than if they received no TXA.

Note that given the complexity of the fibrinolysis process, prior to the present disclosure, it was difficult to measure or even detect either fibrinolysis shutdown or latent hyperfibrinolysis. Moreover, to be beneficial to a patient who may need to be treated (e.g., with therapeutically relevant amount of a therapeutic agent that strengthens a blood clot or slows the dissolution of a blood clot such as tranexamic acid or epsilon aminocaproic acid in the case of a patient with latent hyperfibrinolysis or with a therapeutic agent that weakens a blood clot or speeds the dissolution of a blood clot such as rivaroxaban (a Factor Xa inhibitor) or argatroban (a direct thrombin inhibitor) in the case of a patient with fibrinolysis shutdown), the detection of latent hyperfibrinolysis or fibrinolysis shutdown is preferably very rapid.

In some embodiments, the invention provides methods and reagents for rapidly detecting fibrinolysis shutdown or latent hyperfibrinolysis in a blood sample of a patient. In some embodiments, the invention employs exogenous tPA to shift the balance of PAI-1, tPA and the PAI-1/tPA complex in blood and read out a functional outcome. In some embodiments, the invention provides an indirect functional assay for tPA inhibition. In some embodiments of the present invention, patients can be quickly identified to determine which patients should receive no treatment, which patients have latent hyperfibrinolysis and should receive treatment with a therapeutic agent that strengthens a blood clot or slows the dissolution of a blood clot (e.g., tranexamic acid or epsilon aminocaproic acid), and which patients have fibrinolysis shutdown and should receive either no treatment or treatment with therapeutic agent that weakens a blood clot or speeds the dissolution of a blood clot (e.g., heparin, warfarin, aspirin, clopidogrel, a direct thrombin inhibitor such as hirudin, or a Factor Xa inhibitor such as edoxaban).

Accordingly, in a first aspect, the invention provides method for detecting an aberrant fibrinolysis in a patient, comprising subjecting a blood sample from the patient to a viscoelastic analysis in the presence of a known amount of a thrombolytic agent, to obtain a coagulation characteristic value of the patient; and comparing the coagulation characteristic value of the patient to a coagulation characteristic value of a healthy individual, the coagulation characteristic value of the healthy individual obtained by subjecting a blood sample from a healthy individual to the viscoelastic analysis clotting assay in the presence of the known amount of the thrombolytic agent, wherein a difference in the coagulation characteristic value of the patient as compared to the coagulation characteristic value of the healthy individual identifies the patent as having the aberrant fibrinolysis condition.

It should be noted that the coagulation characteristic value of a healthy individual may be an averaged value from multiple healthy individuals. Additionally, the coagulation characteristic value of a healthy individual(s) may be a stored value or a known value.

As used herein, by "blood sample" is meant a sample of blood (e.g., whole blood, treated blood, or a component of blood) taken, for example, from a patient. The patient may be a human, but may also be any other animal (e.g., veterinary animal or exotic animal). Blood is the circulating tissue of an organism that carries oxygen and nutritive materials to the tissues and removes carbon dioxide and various metabolic products for excretion. Blood (often called whole blood) consists of a pale yellow or gray yellow fluid, plasma, in which are suspended red blood cells, white blood cells, and platelets. In some embodiments, the blood sample is whole blood. The blood may be untreated, or may be treated (e.g., with citrate). For example, a blood sample may be citrated blood (e.g., whole blood collected into a 3.5 mL container containing 3.2% citrate). The blood sample may also be heparinized blood or may be a blood sample treated with protamine to reverse the effects of heparin. In some embodiments, the blood sample is one or more components of whole blood. Thus, a blood sample may be plasma or platelet-free plasma taken from the blood of the patient. In some embodiments, the blood sample may be a sample that has reduced platelet function. For example, the blood sample may be treated with an inhibitor of platelet function such as cytochalasin D.

In some embodiments, the blood sample is taken from a source. The source can be any source including a donor bag or directly from a patient. In some embodiments, the patient from whom the blood sample is taken is responsive to the therapeutic agent that strengthens a blood clot or slows the dissolution of a blood clot (e.g., the antifibrinolytic agent tranexamic acid). In some embodiments, the patient from whom the blood sample is taken is responsive to the therapeutic agent that weakens a blood clot or speeds the dissolution of a blood clot (e.g., tPA).

In some embodiments, the aberrant fibrinolysis condition is latent hyperfibrinolysis. In methods where the aberrant fibrinolysis is latent hyperfibrinolysis, the known amount of the thrombolytic agent (e.g., tPA) is a low amount. In some embodiments, the low amount of thrombolytic agent (e.g., tPA) is between about 1 ng/ml to about 100 ng/ml. In some embodiments, the low amount of thrombolytic agent (e.g., tPA) is between about 10 ng/ml to about 90 ng/ml. In some embodiments, the low amount of thrombolytic agent (e.g., tPA) is between about 20 ng/ml to about 80 ng/ml.

In some embodiments, where the viscoelastic assay is performed in the presence of a low amount of thrombolytic agent, a decrease in the coagulation characteristic value reflective of the coagulation process (e.g., a MA value) of the patient as compared to the coagulation characteristic value reflective of the coagulation process of the healthy individual identifies the patient as having latent hyperfibrinolysis. In some embodiments, a coagulation characteristic value reflective of the coagulation process of the patient that is at least about 7.5% less than the coagulation characteristic value reflective of the coagulation process of the healthy individual identifies the patient as having latent hyperfibrinolysis. In some embodiments, a coagulation characteristic value reflective of the coagulation process of the patient that is at least about 10% less than the coagulation characteristic value reflective of the coagulation process of the healthy individual identifies the patient as having latent hyperfibrinolysis.

In some embodiments, where the viscoelastic assay is performed in the presence of a low amount of thrombolytic agent, an increase in the coagulation characteristic value reflective of the fibrinolysis process (e.g., a LY30 value) of the patient as compared to the coagulation characteristic value reflective of the fibrinolysis process of the healthy individual identifies the patient as having latent hyperfibrinolysis. In some embodiments, a coagulation characteristic value reflective of the fibrinolysis process of the patient that is at least about 7.5% greater than the coagulation characteristic value reflective of the fibrinolysis process of the healthy individual identifies the patient as having latent hyperfibrinolysis. In some embodiments, a coagulation characteristic value reflective of the fibrinolysis process of the patient that is at least about 10% greater than the coagulation characteristic value reflective of the fibrinolysis process of the healthy individual identifies the patient as having latent hyperfibrinolysis.

Patients who are identified as having latent hyperfibrinolysis may benefit from treatment with a therapeutically relevant amount of a therapeutic agent that strengthens a blood clot or slows the dissolution of a blood clot.

By a "therapeutic agent that strengthens a blood clot or slows the dissolution of a blood clot" is meant any chemical that either interferes with or inhibits the breakdown or dissolution of a blood clot or slows down or inhibits the dissolution or breakdown of a blood clot. In some embodiments, a therapeutic agent that strengthens a blood clot or slows the dissolution of a blood clot is not the same as a therapeutic agent that weakens a blood clot or speeds the dissolution of a blood clot.

In some embodiments, a therapeutic agent that strengthens a blood clot or slows the dissolution of a blood clot includes, without limitation, antifibrinolytic agents (also called antifibrinolytics), specific factor replacement (e.g., Factor XIII), prothrombic complex concentrate, fibrinogen concentrate, and living donor human blood products such as plasma. Non-limiting antifibrinolytic agents include plasminogen activator inhibitor 1 (PAI-1), plasminogen activator inhibitor 2 (PAI-2), tranexamic acid, aminocaproic acid (e.g., epsilon aminocaproic acid), aprotinin.

In some embodiments, the aberrant fibrinolysis condition is fibrinolysis shutdown. In methods where the aberrant fibrinolysis is fibrinolysis shutdown, the known amount of thrombolytic agent (e.g., tPA) is a high amount. In some embodiments, the high amount of thrombolytic agent (e.g., tPA) is between about 110 ng/ml to about 1200 ng/ml. In some embodiments, the high amount of thrombolytic agent (e.g., tPA) is between about 150 ng/ml to about 1000 ng/ml. In some embodiments, the high amount of thrombolytic agent (e.g., tPA) is between about 200 ng/ml to about 900 ng/ml. In some embodiments, the high amount of thrombolytic agent (e.g., tPA) is between about 300 ng/ml to about 900 ng/ml.

In some embodiments, where the viscoelastic assay is performed in the presence of a high amount of thrombolytic agent, an increase in the coagulation characteristic value reflective of the coagulation process of the patient as compared to the coagulation characteristic value reflective of the coagulation process of the healthy individual identifies the patient as having fibrinolysis shutdown. In some embodiments, a coagulation characteristic value reflective of the coagulation process of the patient that is at least about 7.5% greater than the coagulation characteristic value reflective of the coagulation process of the healthy individual identifies the patient as having fibrinolysis shutdown. In some embodiments, a coagulation characteristic value reflective of the coagulation process of the patient that is at least about 10% greater than the coagulation characteristic value reflective of the coagulation process of the healthy individual identifies the patient as having fibrinolysis shutdown.

In some embodiments, where the viscoelastic assay is performed in the presence of a high amount of thrombolytic agent, a decrease in the coagulation characteristic value reflective of the fibrinolysis process of the patient as compared to the coagulation characteristic value reflective of the fibrinolysis process of the healthy individual identifies the patient as having fibrinolysis shutdown. In some embodiments, a coagulation characteristic value reflective of the fibrinolysis process of the patient that is at least about 7.5% lower than the coagulation characteristic value reflective of the fibrinolysis process of the healthy individual identifies the patient as having fibrinolysis shutdown. In some embodiments, a coagulation characteristic value reflective of the fibrinolysis process of the patient that is at least about 10% lower than the coagulation characteristic value reflective of the fibrinolysis process of the healthy individual identifies the patient as having fibrinolysis shutdown.

Patients who are identified as having fibrinolysis shutdown may benefit from treatment with a therapeutically relevant amount of a therapeutic agent that weakens a blood clot or speeds the dissolution of a blood clot.

By a "therapeutic agent that weakens a blood clot or speeds the dissolution of a blood clot" is meant any chemical that interferes with or inhibits the formation of a blood clot or speeds the dissolution or breakdown of a blood clot. In some embodiments, a therapeutic agent that weakens a blood clot or speeds the dissolution of a blood clot is not the same as a therapeutic agent that strengthens a blood clot or slows the dissolution of a blood clot. Thus the term "therapeutic agent that weakens a blood clot or speeds the dissolution of a blood clot" includes, without limitation, anticoagulants, thrombolytic agents, antifibrinogen agents, anti-Factor XIII agents, and antiplatelet agents. Anticoagulants include, without limitation, chemicals that inhibit platelets or inhibit factors in the coagulation cascade such as direct thrombin inhibitors (e.g., argatroban, melagatran, ximelagatran, and dabigatran), direct Factor Xa inhibitors (e.g., rivaroxaban, apixaban and edoxaban), heparin, and vitamin K antagonists (e.g., warfarin). Thrombolytic agents (also called thrombolytics) include, without limitation, chemicals that activate the breakdown of a blood clot such as single or double chain human tissue plasminogen activator (tPA), tPA from other species, alteplase, reteplase, tenecteplase, anistreplase, serokinase, streptokinase, urokinase, kallikrein, or any other upregulator of the plasmin/fibrinolytic system. Antiplatelet agents include, without limitation, aspirin, clopidogrel (a $P2Y_{12}$ receptor antagonist), and Glycoprotein IIb/IIIa receptor antagonists.

In some embodiments, the invention enables the determination of the appropriate dosages of a therapeutic agent that weakens a blood clot or speeds the dissolution of a blood clot such as an anticoagulant or a thrombolytic agent for individual patients for treatment of disease conditions including deep vein thrombosis (DVT), pulmonary embolism (PE), myocardial infarction (MI) or ischemic stroke, by defining the patient's baseline level of resistance to the therapeutic agent that weakens a blood clot or speeds the dissolution of a blood clot (e.g., a thrombolytic agent such as tPA) and that patient's response to systemic therapy.

As used herein, by "viscoelastic analysis" is meant any analysis method that measures the characteristics of elastic solid (e.g., fibrin solids) and fluids. In other words, viscoelastic analysis allows the study of properties of a viscous fluid, such as blood or a blood sample.

In some embodiments, the viscoelastic analysis is performed under conditions that mimic the conditions in vivo that result in hemostasis. For example, the condition may include a temperature that mimics a body temperature (e.g., a temperature of 37° C.). The condition may also include clot formation and dissolution at flow rates that mimic those found in blood vessels.

In one non-limiting form, a non-limiting assay included in an embodiment of the invention includes a group of 3 citrated native TEGs with 0, 75 or 150 ng/mL of human single-chain tPA added to the whole blood mixture, with the LY30 of the two tPA-containing cups compared to the native TEG without tPA. This grouping may be performed, for example, in a single cartridge of a vasoelectric analysis instrument, where the cartridge has multiple channels, where one channel holds a separate sample (e.g., one channel holds untreated blood, another holds blood with 75 ng/ml tPA, etc.). The low concentration (75 ng/mL) sample produces minimal clot lysis in healthy individuals, but reveals latent hyperfibrinolysis with an elevated LY30 in individuals with latent hyperfibrinolysis. Conversely, the high concentration (150 ng/mL tPA) will produce severe fibrinolysis (roughly 20%) in blood of healthy individuals. However, if a severely injured individual displays resistance to fibrinolysis in the presence of 150 ng/ml tPA, that individual may have fibrinolysis shutdown. In certain individuals and in animal models, other concentrations of tPA or other thrombolytic agents may be employed, as needed.

In some embodiments, viscoelastic analysis of a blood sample may include subjecting the blood sample to analysis on a hemostasis analyzer instrument. One non-limiting viscoelastic analysis method is the thromboelastography ("TEG") assay. Thus in some embodiments, the viscoelastic analysis includes subjecting a blood sample to analysis using thromboelastography (TEG), which was first described by Helmut Hartert in Germany in the 1940's.

Various devices that perform thromboestography, and methods for using it are described in U.S. Pat. Nos. 5,223,227; 6,225,126; 6,537,819; 7,182,913; 6,613,573; 6,787,363; 7,179,652; 7,732,213, 8,008,086; 7,754,489; 7,939,329; 8,076,144; 6,797,419; 6,890,299; 7,524,670; 7,811,792; 20070092405; 20070059840; U.S. Pat. No. 8,421,458; US 20120301967; and U.S. Pat. No. 7,261,861, the entire disclosures of each of which are hereby expressly incorporated herein by reference.

Thromboelastography (TE) monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood. In essence, the clot is the elementary machine of hemostasis. Hemostasis instruments that measure hemostasis are able to measure the ability of the clot to perform mechanical work throughout its structural development. These hemostasis analyzers measure continuously all phases of patient hemostasis as a net product of whole blood components in a non-isolated, or static fashion from the time of test initiation until initial fibrin formation, through clot rate strengthening and ultimately clot strength through coagulation characteristic.

In some embodiments, the viscoelastic analysis and/or the hemostasis analyzer comprises a container which is in contact with the blood.

As used herein, by "container" is meant a rigid surface (e.g., a solid surface), a portion of which contacts a portion of a blood sample placed into the container at any point during the viscoelastic analysis. The portion of the container that contact the portion of blood sample may also be referred to as the "interior" of the container. Note that the phase "into the container" does not mean that the container has a bottom surface which is in contact with the portion of the blood sample. Rather, the container can be a ring-shaped structure, where the inside of the ring is the interior of the container, meaning that the inside of the ring is the portion of the ring-shaped container that contacts a portion of the blood sample. A blood sample can flow into the container and be held there, for example, by vacuum pressure or surface tension.

Still additional types of containers that are included in this definition are those present on cartridges and cassettes (e.g., a microfluidic cartridge), where the cartridge or cassette has multiple channels, reservoirs, tunnels, and rings therein. Each of the contiguous channels (comprising, for example, a channel, a reservoir, and a ring) is a container, as the term is used herein. Hence, there may be multiple containers on one cartridge. U.S. Pat. No. 7,261,861 (incorporated herein by reference) describes such a cartridge with multiple channels or containers. Any of the surfaces in any of the channels or tunnels of the cartridge may be an interior of the container if that surface comes into contact with any portion of the blood sample, at any time during the viscoelastic analysis.

One non-limiting hemostasis analyzer instrument is described in U.S. Pat. No. 7,261,861; US Patent Publication No. US US20070092405; and US Patent Publication No. US20070059840.

Another non-limiting hemostasis analyzer instrument that performs viscoelastic analysis using thromboelastography is the TEG thromboelastograph hemostasis analyzer system sold commercially by Haemonetics, Corp. (Braintree, Mass.).

Figure 4:
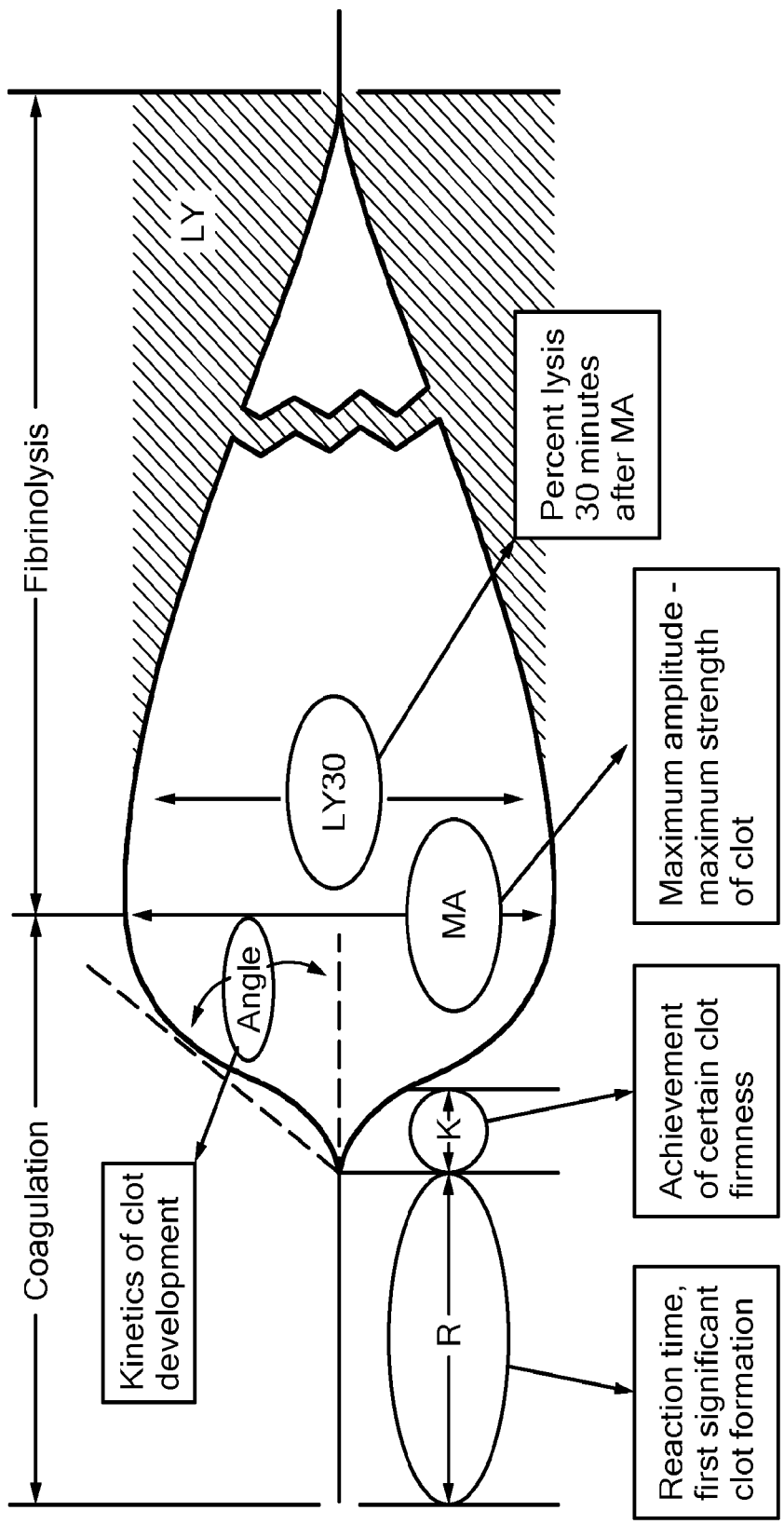
FIG. 4 is schematic diagram showing a thromboelastography ("TEG") assay tracing from a sample with normal hemostasis; that is, a normal amount of fibrinolysis and no hyperfibrinolysis. The R (reaction time) is the time of formation of the fibrin strand polymers, K (clot kinetics, measured in minutes), and MA (maximum amplitude, measured in mm) is the strength of the clot. The LY30 is the percent lysis present thirty minutes after the MA.
Figure 5:
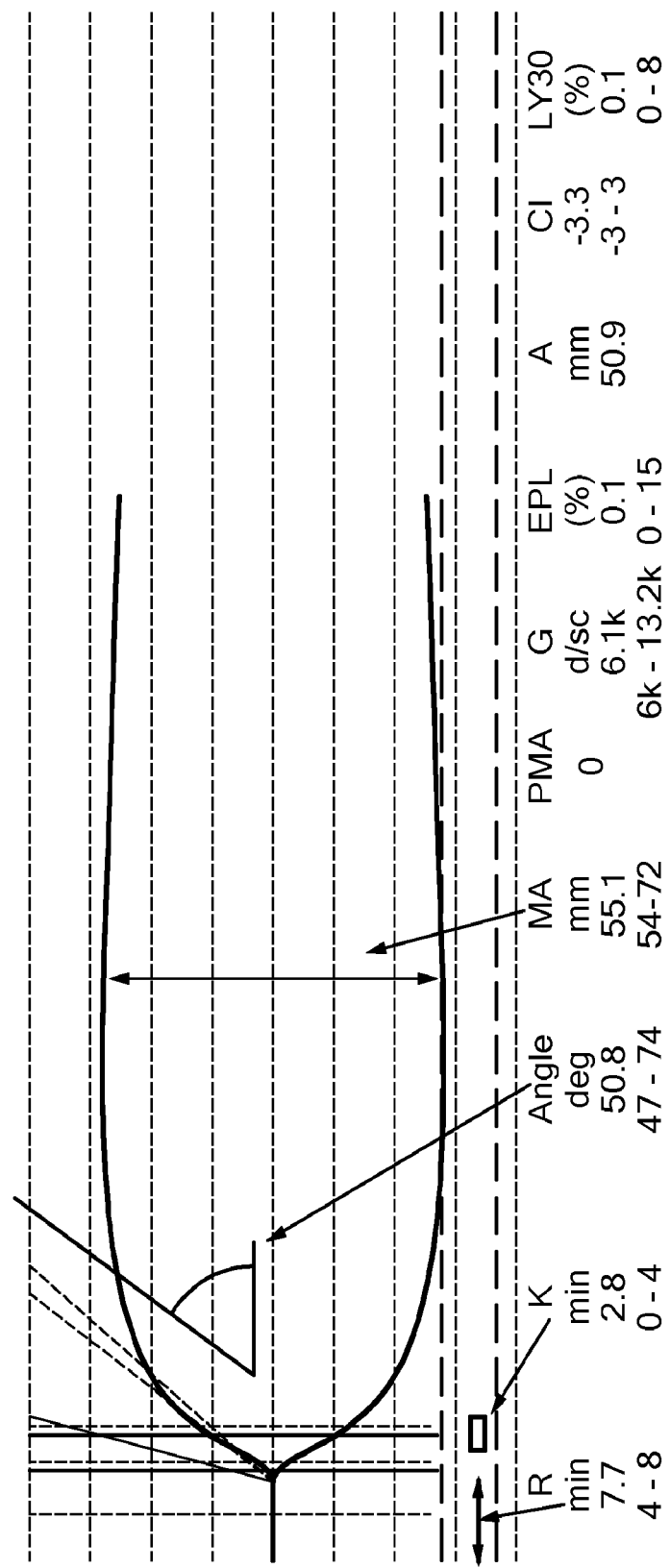
FIG. 5 is a TEG tracing of a blood sample from a healthy individual, where the blood sample has not been treated with either a therapeutic agent that strengthens a blood clot or slows the dissolution of a blood clot or a therapeutic agent that weakens a blood clot or speeds the dissolution of a blood clot.

Thus, the TEG assay may be performed using the TEG thromboelastograph hemostasis analyzer system that measures the mechanical strength of an evolving blood cloth. To run the assay, the blood sample is placed into a container (e.g., a cup or a cuvette), and a pin goes into the center of the container. Contact with the interior walls of the container (or addition of a clot activator to the container) initiates clot formation. The TEG thromboelastograph hemostasis analyzer then rotates the container in an oscillating fashion, approximately 4.45 degrees to 4.75 degrees, every 10 seconds, to imitate sluggish venous flow and activate coagulation. As fibrin and platelet aggregates form, they connect the inside of the container with the pin, transferring the energy used to move the container in the pin. A torsion wire connected to the pin measures the strength of the clot over time, with the magnitude of the output directly proportional to the strength of the clot. As the strength of the clot increases over time, a classic TEG tracing curve develops (See FIGS. 4 and 5). The schematic shown in FIG. 4 depicts a TEG tracing when fibrinolysis occurs. Of course, a typical TEG tracing of an untreated blood sample from a healthy individual (i.e., blood not treated with either a therapeutic agent that strengthens a blood clot or slows the dissolution of a blood clot or a therapeutic agent that weakens a blood clot or speeds the dissolution of a blood clot) is shown in FIG. 5.

Where there is a pin in the TEG analyzer, the rotational movement of the pin is converted by a transducer to an electrical signal, which can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the skills of one having ordinary skill in the art. As shown in FIG. 4, the resulting hemostasis profile (i.e., a TEG tracing curve) is a measure of the time it takes for the first fibrin strand to be formed, the kinetics of clot formation, the strength of the clot (measured in millimeters (mm) and converted to shear elasticity units of dyn/cm 2) and dissolution of clot. See also Donahue et al., *J. Veterinary Emergency and Critical Care:* 15(1): 9-16 (March 2005), herein incorporated by reference The descriptions for several of these measured parameters are as follows:

R is the period of time of latency from the time that the blood was placed in the thromboelastography analyzer until the initial fibrin formation. This is typically takes about 30 second to about 10 minutes; however the R range will vary based on the particular TEG assay performed (e.g., type of blood sample being tested (e.g., plasma only or whole blood), whether the blood component is citrated or not, etc.). For patients in a hypocoagulable state (i.e., a state of decreased coagulability of blood), the R number is longer, while in a hypercoagulable state (i.e., a state of increased coagulability of blood), the R number is shorter. In the methods described herein, the R value (in minutes or seconds) can be used as a non-limiting coagulation characteristic value.

K value (measured in minutes) is the time from the end of R until the clot reaches 20 mm and this represents the speed of clot formation. This K value is about 0 to about 4 minutes (i.e., after the end of R). In a hypocoagulable state, the K number is longer, while in a hypercoagulable state, the K number is shorter. In the methods described herein, the K value can be used as a non-limiting coagulation characteristic value.

α (alpha) value measures the rapidity of fibrin build-up and cross-linking (clot strengthening). Thus, the a (alpha) value is reflective of the coagulation process. It is angle between the line formed from the split point tangent to the curve and the horizontal axis. This angle is typically about 47° to 74°. In a hypocoagulable state, the a degree is lower, while in a hypercoagulable state, the a degree is higher. In the methods described herein, the a value can be used as a non-limiting coagulation characteristic value.

MA or Maximum Amplitude in mm, is a direct function of the maximum dynamic properties of fibrin and platelet bonding and represents the ultimate strength of the blood clot. The MA value is reflective of the coagulation process and is typically from about 54 mm to about 72 mm. The MA occurs typically between about 15 to about 35 minutes after the start of the viscoelastic assay. Note that if the blood sample tested has a reduced platelet function (e.g., platelet-free plasma), this MA represents the strength of the clot based mainly on fibrin. Decreases in MA may reflect a hypocoagulable state (e.g., with platelet dysfunction or thrombocytopenia), whereas an increased MA (e.g., coupled with decreased R) may be suggestive of a hypercoagulable state.

In some embodiments, a latent hyperfibrinolysis condition state is present in a patient if the MA coagulation characteristic value of the patient is less than the MA coagulation characteristic value of a healthy individual (or averaged MA value of a group of healthy individuals), as determined by TEG in the presence of a low amount of tPA or other thromolytic agent. In some embodiments, a latent hyperfibrinolysis condition state is present in a patient if the MA coagulation characteristic value of the patient is at least about 7.5% less than the MA coagulation characteristic value of a healthy individual (or averaged MA value of a group of healthy individuals), as determined by TEG in the presence of a low amount of tPA or other thromolytic agent. In some embodiments, an MA from a patient that is about 6%, or about 5%, or about 4%, less than the MA of a healthy individual (or averaged MA value of a group of healthy individuals) as determined by TEG in the presence of a low amount of tPA or other thrombolytic agent identifies a patient with latent hyperfibrinolysis. In some embodiments, a fibrinolysis shutdown condition is present in a patient if the MA coagulation characteristic value of the patient is greater than the MA coagulation characteristic value of a healthy individual (or averaged MA value of a group of healthy individuals), as determined by TEG in the presence of a high amount of tPA. In the methods described herein, the MA value can be used as a non-limiting coagulation characteristic value.

LY30 is a measure of amplitude reduction 30 minutes after MA and represents clot retraction, or lysis. The LY30 value is thus a percentage decrease in amplitude 30 minutes after the Ma, and is reflective of the fibrinolysis process. This number is typically 0% to about 8%. The larger the LY30 value, the faster fibrinolysis occurs. When no fibrinolysis occurs, the amplitude value at the MA tracing stays constant or may decrease slightly due to clot retraction. However, as fibrinolysis occurs (e.g., in a healthy individual), the curve of the TEG tracing starts to decay. The resultant loss in potential area-under-the-curve in the 30 minutes following Maximum Amplitude in the TEG assay is called the LY30 (see FIGS. 4 and 5). LY30, the percentage of lysis 30 minutes after the maximum amplitude point (expressed as a percentage of the clot lysed) indicates the rate of coagulation characteristic. In some embodiments, clot firmness (G, measured in dynes/cm2) may be used to express LY30. In some embodiments, a latent hyperfibrinolysis condition is present in a patient if the LY30 coagulation characteristic value of the patient is greater than the LY30 coagulation characteristic value as determined by TEG in the presence of a low amount of tPA or other thrombolytic agent.

In some embodiment, a latent hyperfibrinolysis condition is present in a patient if the LY30 coagulation characteristic value of the patient is at least about 3% greater than the LY30 coagulation characteristic value of a healthy individual (or averaged LY30 value of a group of healthy individuals), as determined by TEG in the presence of a low amount of tPA or other thrombolytic agent. In some embodiments, an LY30 from a patient that is at least about 5%, or at least about 7.5%, or at least about 10%, or at least about 15%, greater than the LY30 of a healthy individual (or averaged LY30 value of a group of healthy individuals) as determined by TEG in the presence of a low amount of tPA or other thrombolytic agent identifies a patient with latent hyperfibrinolysis. In some embodiments, a fibrinolysis shutdown condition is present in a patient if the LY30 coagulation characteristic value of the patient is less than the LY30 coagulation characteristic value of a healthy individual (or averaged LY30 value of a group of healthy individuals), as determined by TEG in the presence of a high amount of tPA or other thrombolytic agent. In some embodiments, a fibrinolysis shutdown condition is present in a patient if the LY30 coagulation characteristic value of the patient is at least about 3% less than the LY30 coagulation characteristic value of a healthy individual (or averaged LY30 value of a group of healthy individuals), as determined by TEG in the presence of a high amount of tPA. In some embodiments, an LY30 from a patient that is at least about 5%, or at least about 7.5%, or at least about 10%, or at least about 15%, less than the LY30 of a healthy individual (or averaged LY30 value of a group of healthy individuals) as determined by TEG in the presence of a high amount of tPA or other thrombolytic agent identifies a patient with fibrinolysis shutdown. In the methods described herein, the LY30 value can be used as a non-limiting coagulation characteristic value.

It should be noted that modifications of the TEG assay can be performed.

Another viscoelastic hemostasis assay that can be used is the thromboelastometry ("TEM") assay. This TEM assay may be performed using the ROTEM Thromboelastometry Coagulation Analyzer (TEM international GmbH, Munich, Germany), the use of which is well known (See, e.g., Sorensen, B., et al., *J. Thromb. Haemost.*, 2003. 1(3): p. 551-8. Ingerslev, J., et al., *Haemophilia*, 2003. 9(4): p. 348-52. Fenger-Eriksen, C., et al. *Br J Anaesth*, 2005. 94(3): p. 324-9]. In the ROTEM analyzer, the blood sample is placed into a container (also called a cuvette or cup) and a cylindrical pin is immersed. Between pin and the interior wall of the container there is a gap of 1 mm which is bridged by the blood. The pin is rotated by a spring to the right and the left. As long as the blood is liquid (i.e., unclotted), the movement is unrestricted. However, when the blood starts clotting, the clot increasingly restricts the rotation of the pin with rising clot firmness. The pin is connected to an optical detector. This kinetic is detected mechanically and calculated by an integrated computer to the typical tracing curves (TEMogram) and numerical parameters (see FIGS. 6A and 6B).

Figure 6A:
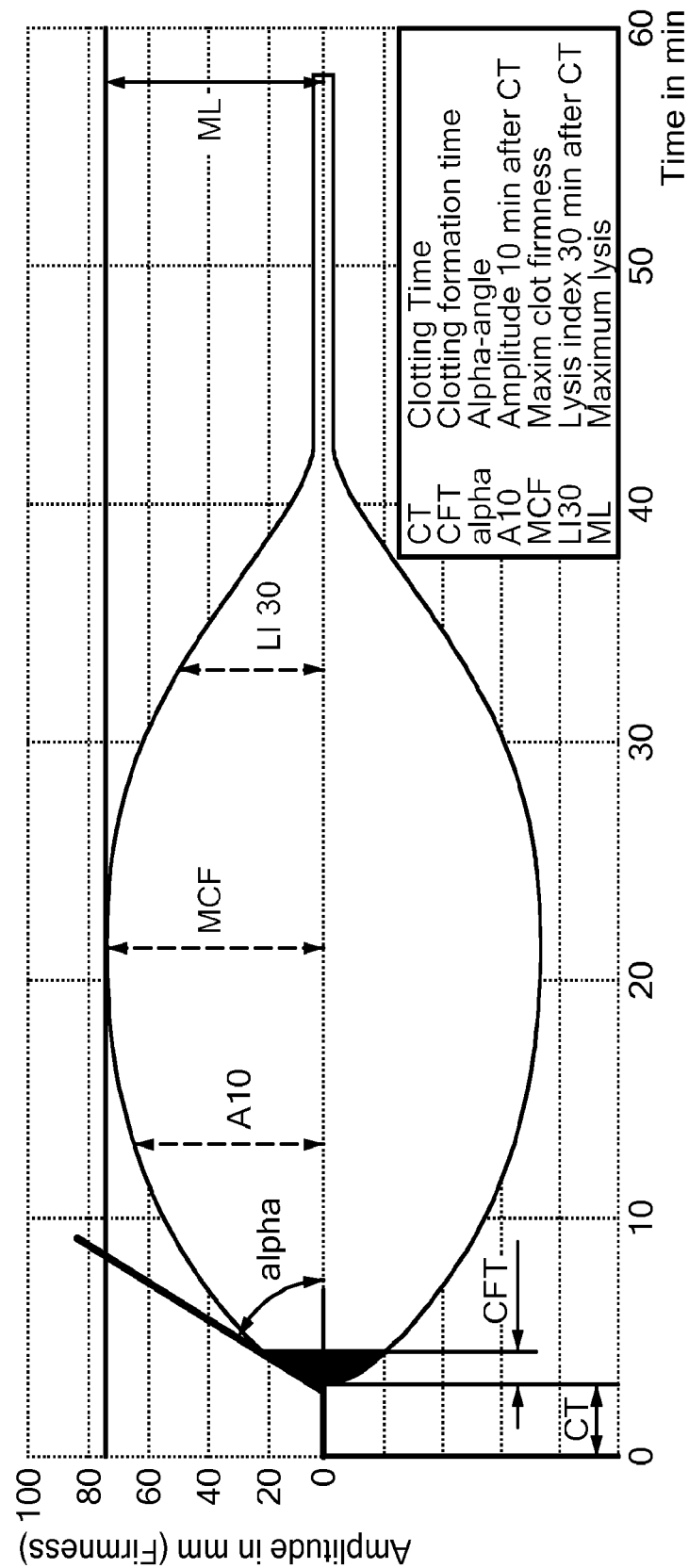
FIGS. 6A and 6B are schematic diagrams showing two typical TEMogram tracings.
Figure 6B:
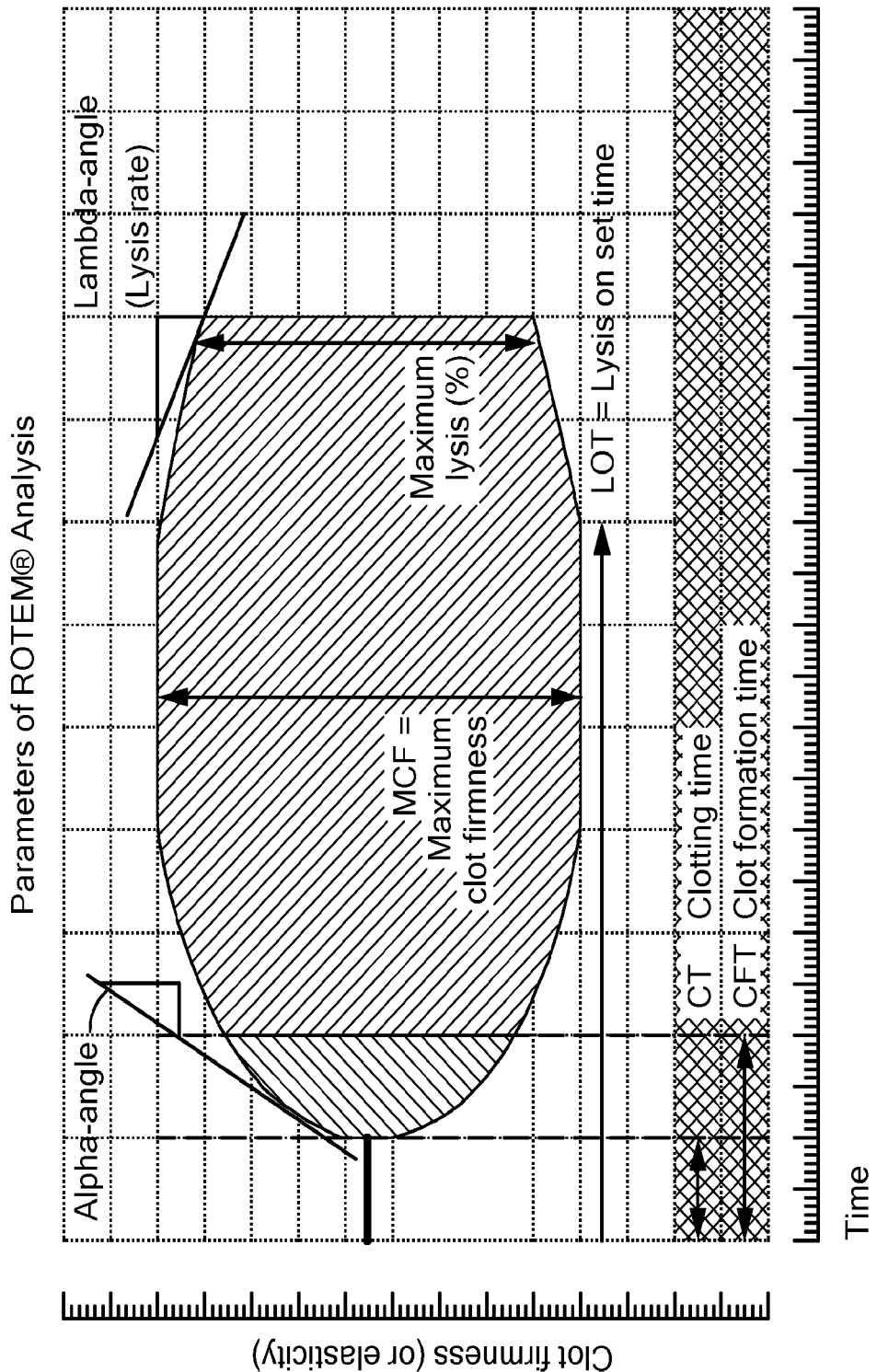

In the ROTEM Thromboelastometry Coagulation Analyzer, the movement of the pin can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile (called a TEMogram. Such a configuration of the computer is well within the skills of one having ordinary skill in the art. As shown in FIGS. 6A and 6B, the resulting hemostasis profile (i.e., a TEM tracing curve) is a measure of the time it takes for the first fibrin strand to be formed, the kinetics of clot formation, the strength of the clot (measured in millimeters (mm) and converted to shear elasticity units of dyn/cm 2) and dissolution of clot. The descriptions for several of these measured parameters are as follows:

CT (clotting time) is the period of time of latency from the time that the blood was placed in the ROTEM analyzer until the clot begins to form. This CT time may be used as a non-limiting coagulation characteristic value in accordance with the methods described herein.

CFT (Clot formation time): the time from CT until a clot firmness of 20 mm point has been reached. This CFT time may be used as a non-limiting coagulation characteristic value in accordance with the methods described herein.

alpha-angle: The alpha angle is the angle of tangent at 2 mm amplitude. This alpha angle may be used as a non-limiting coagulation characteristic value in accordance with the methods described herein.

MCF (Maximum clot firmness): MCF is the greatest vertical amplitude of the trace. MCF reflects the absolute strength of the fibrin and platelet clot. If the blood sample tested has a reduced platelet function, this MCF is a function of mainly the fibrin bonding strength. The MCF value may be used as a non-limiting coagulation characteristic value in accordance with the methods described herein.

A10 (or A5, A15 or A20 value). This value describes the clot firmness (or amplitude) obtained after 10 (or 5 or 15 or 20) minutes and provide a forecast on the expected MCF value at an early stage. Any of these A values (e.g., A10) may be used as a non-limiting coagulation characteristic value in accordance with the methods described herein.

LI 30 (Lysis Index after 30 minutes). The LI30 value is the percentage of remaining clot stability in relation to the MCF value at 30 min after CT. This LI30 value may be used as a non-limiting coagulation characteristic value in accordance with the methods described herein. When no fibrinolysis occurs, the amplitude value at the MCF on a TEM tracing stays constant or may decrease slightly due to clot retraction. However, as fibrinolysis occurs (e.g., in a hypocoagulable state), the curve of the TEM tracing starts to decay. LI30 corresponds to the LY30 value from a TEG tracing.

ML (Maximum Lysis). The ML parameter describes the percentage of lost clot stability (relative to MCF, in %) viewed at any selected time point or when the test has been stopped. This ML value may be used as a non-limiting coagulation characteristic value in accordance with the methods described herein.

A low LI 30 value or a high ML value indicates hyperfibrinolysis. While in normal blood fibrinolysis activity is quite low, in clinical samples a more rapid loss of clot stability by hyperfibrinolysis may lead to bleeding complications which can be treated by the administration of a therapeutic agent that strengthens a blood clot or slows the dissolution of a blood clot, such as an antifibrinolytic agent.

Thus, parameters of interest in TEG or TEM assays, each of which can be used as a coagulation characteristic value in accordance with the methods described herein, include the maximum strength of the clot which is a reflection of clot strength. This is the MA value in the TEG assay, and the MCF value in the TEM assay. The reaction time (R) in TEG (measured in seconds or minutes) and clotting time (CT) in TEM is the time until there is first evidence of clot; clot kinetics (K, measured in minutes) is a parameter in the TEG test indicating the achievement of clot firmness; and a in TEG or alpha-angle in TEM is an angular measurement from a tangent line drawn to the curve of the TEG tracing or TEM tracing starting from the point of clot reaction time that is reflective of the kinetics of clot development. (See Trapani, L. M. Thromboelastography: Current Applications, Future Directions", Open Journal of Anesthesiology 3(1): Article ID: 27628, 5 pages (2013); and Kroll, M. H., "Thromboelastography: Theory and Practice in Measuring Hemostasis," *Clinical Laboratory News: Thromboelastography* 36(12), December 2010; instruction manuals for the TEG instrument (available from Haemonetics, Corp.), and the instruction manual for the ROTEM instrument (available from TEM international GmbH), all of which documents are herein incorporated by reference in their entireties.

In some embodiments, the parameters (and hence the coagulation characteristic value) are recorded by observation of different excitation levels of the sample as coagulation occurs. For example, where the container is a microfluidic cartridge, or a particular channel in the cartridge, the blood sample may be excited at a resonant frequency and its behavior observed by an electromagnetic or light source as coagulation occurs. In other embodiments the sample's coagulation characteristic value may be observed for changes with a light source without exciting the sample.

Because a single cartridge may have multiple containers (e.g., different channels in the cartridge), a patient sample in a container contacted with a known amount of tPA is easily directly comparable to a control sample from a healthy individual in a container (e.g., in an adjacent channel in the same microfluidic cartridge) that is contacted with the same known amount of tPA.

When no fibrinolysis occurs (e.g., in a fibrinolysis shutdown situation with no added tPA), the amplitude value at the MA on a TEG tracing and the amplitude value at the MCF on a TEM tracing stays constant or may decrease slightly due to clot retraction. However, as fibrinolysis occurs (e.g., in a latent hyperfibrinolysis situation with a low amount of a thrombolytic agent such as tPA), the curve of the TEG tracing and the TEM tracing starts to decay. The resultant loss in potential area-under-the-curve in the 30 minutes following Maximum Amplitude in the TEG assay is called the LY30 (see FIGS. 4 and 5). LY30, the percentage of lysis 30 minutes after the maximum amplitude point (expressed as a percentage of the clot lysed) indicates the rate of coagulation characteristic. The corresponding value in the TEM assay is the LI30 value (see FIG. 6A).

As used herein, by a "coagulation characteristic" is meant a parameter that indicates the hemostasis status of the blood sample being tested. Any coagulation characteristic values measured using a viscoelastic analysis assay can be used in the methods described herein to determine if a patient has fibrinolysis shutdown or latent hyperfibrinolysis. For example, in the TEG assay, any of R (reaction time), K (time clot firmness is achieved), a (kinetics of clot development), MA (maximum amplitude), and LY30 can be compared (see FIGS. 4 and 5). For the TEM assay, any of CT (clotting time), CFT (clot formation time), alpha angle, MCF (maximum clot firmness), A10 (amplitude 10 minutes after CT), LI30 (lysis index 30 minutes after CT) and ML (maximum lysis) can be compared (see FIGS. 6A and 6B) as well as derivatives of any and all of these parameters can also be used as coagulation characteristics.

Thus, in some embodiments of the methods described herein, the viscoelastic analysis is performed using a TEG thromboelastography analyzer system or in a ROTEM thromboelastometry analyzer system.

Indeed, in some embodiments, in a trauma situation, the routinely skilled physician may simply perform a viscoelastic assay (e.g., a TEG assay) on blood samples (e.g., platelet-deleted blood samples) from the patient, one with thrombolytic agent (e.g., no tPA), one with a low amount of the thrombolytic agent, and one with the high amount of the thrombolytic agent in real time, and once the two tracings begin to diverge (e.g., as early as two minutes after the start of the assay) from a control blood sample (e.g., taken from donated blood from a healthy individual), the physician may choose to treat the patient with a therapeutic agent that strengthens a blood clot or slows the dissolution of a blood clot such as an antifibrinolytic agent (e.g., tranexamic acid or epsilon aminocaproic acid or, as a last resort, aprotinin), or a therapeutic agent that weakens a blood clot or speeds the dissolution of a blood clot such an anticoagulant agent or a thrombolytic agent (e.g., heparin, aspirin, or tPA) at that very moment. Or, from the patient's coagulation characteristic value (e.g., the patient's R time), the physician may be able to identify the patient a healthy individual, thus enabling the physician to attend to other patients in more imminent need of care. Hence, the speed in detecting fibrinolysis shutdown or latent hyperfibrinolysis in a patient is clinically relevant, particularly in the case of trauma patients where life and death outcomes can be decided within a matter of minutes.

The methods described herein thus compare a coagulation characteristic value in a patient blood sample treated with a known amount of a thrombolytic agent such as tPA and that same coagulation characteristic in a control blood sample from a healthy individual.

The invention stems, in part, from an attempt to reduce the amount of time required to detect fibrinolysis shutdown and latent hyperfibrinolysis, so as to improve patient outcomes. Prior to the discovery described in this disclosure, neither fibrinolysis shutdown nor latent hyperfibrinolysis were well known, and could not be detect. As a result, patients who seem otherwise healthy but for their injury (e.g., accidental or imposed during surgery) often surprisingly took a turn for the worse and died. Treatment with a therapeutic agent that strengthens a blood clot or slows the dissolution of a blood clot such as the antifibrinolytic tranexamic acid (TXA) can reduce the mortality of some hyperfibrinolysis patients, but is quite detrimental for patients with fibrinolysis shutdown. Plus, if the patient has latent hyperfibrinolysis, and thus receives no TXA, the outcome is very poor. The present invention allows identification of such patients with latent hyperfibrinolysis and fibrinolysis shutdown to improve their outcomes.

In some embodiments, the low amount or the high amount of the thrombolytic agent coats the interior of the container such that it is in contact with the blood sample once the blood sample is placed into the container.

During hemostasis, platelets are also involved. Produced by megakaryocytes in the bone marrow, these small cytoplasmic vesicles, about 1 um in diameter, are full of active biological agents. Just as the enzymes of the coagulation cascade need to be activated to form a fibrin clot, four agents—adenosine diphosphate (ADP), epinephrine, thrombin, and collagen—activate platelets. An adhesive protein called glycoprotein IIb-IIIa (Gp IIb-IIIa) mediates platelet aggregation. The procoagulant factor, fibrinogen, attaches to this receptor, linking the platelets to each other. The bridging, which is linked by fibrinogen, represents the main source of aggregation. Surgery or trauma exposes the procoagulant factors to the tissue factor, triggering the coagulation cascade. Besides transforming fibrinogen into fibrin, a polymer that strengthens clots, the coagulation cascade produces large amounts of thrombin, the main activator of platelets.

In some embodiments, the contribution of platelets to a patient's clot formation and strength may be removed or reduced, thereby allowing the determination of hyperfibrinolysis or fibrinolysis to be based upon only the fibrin content of the clot, and the contribution of fibrinogen.

Thus in some embodiments, the blood sample is a blood sample that has reduced platelet function. For example, the blood sample may be contacted with a platelet function inhibitor to reduce the function of the platelets in the blood sample. The blood sample may also be physically manipulated (e.g., subjected to centrifugation) to reduce the number of platelets in the blood sample by physical removal of the platelets from the blood sample.

As mentioned above, fibrinogen and platelets both contribute to clot integrity. In some of the methods described herein, fibrinolysis may be detected in a blood sample where platelet function has been reduced (for example by treating the sample with a platelet inhibitor such as cytochalasin D). If fibrinolysis in the platelet function-reduced sample is prevented with the addition of an anti-fibrinolytic agent (e.g., tranexamic acid), the fibrinolysis is likely not due to platelet function but, rather, to fibrin and other factors in the coagulation cascade. Therefore, the patient from whom the sample was obtained (and who is prone to develop, or is currently undergoing fibrinolysis or hyperfibrinolysis) will likely respond to treatment with an anti-fibrolytic agent. Thus, in some embodiments, the blood sample being tested has reduced platelet function as compared to normal whole blood.

Note that by "reduced platelet function" does not mean that the blood sample does not have any platelet function at all. Rather, the blood sample with reduced platelet function simply has reduced platelet function as opposed to normal whole blood. For example, a blood sample with reduced platelet function includes a blood sample that has a platelet function that is at least 25% less, or at least 50% less, or at least 75% less, or at least 90% less platelet function than whole blood. Platelet function includes, without limitation, the contribution to hemostasis. Reduced platelet function can thus be assessed by a reduction in the aggregation of platelets to one another during blood clotting (e.g., in the presence of Kaolin and calcium).

In some embodiments, the blood sample is physically manipulated to reduce the number of platelets in the blood sample. For example, whole blood can be centrifuged to remove some or most of the platelets. In one very simple procedure, 1.5 ul of blood can be centrifuged in a 2.0 ml microcentrifuge tube at 1000 rpm for 10 minutes. The platelet-rich plasma will float on the top of the blood in the supernatant. This supernatant can be removed (e.g., by aspiration) leaving the platelet reduced whole blood at the bottom of the tube. As less than 500 ul of blood is needed to perform the viscoelastic analyses described below, this is a very rapid method to quickly reduce the number of platelets in the blood.

In another method, platelet reduced whole blood can be obtained by contacting whole blood with platelet-specific antibodies attached to a solid surface. The platelets will selectively bind to the solid surface, and the platelet reduced whole blood can be obtained. For example, antibodies that specifically bind to the glycoprotein IIb/IIIa receptor (which is expressed on platelets but not on red blood cells) can be coupled to magnetic beads (e.g., the Dynabeads commercially available from Life Technologies, Carlsbad, Calif., USA). Whole blood can be contacted with the antibody-coated magnetic beads and, after the platelets are allowed to be bound by the antibodies, a magnetic applies. The magnet will attract the beads (and thereby will attract the platelets), and the remaining blood that has a reduced platelet content (and thus a reduced platelet function) will not be bound to the magnetic and can thus be collected.

In some embodiments, platelet function is reduced by contacting the blood sample with a platelet function inhibitor. One non-limiting platelet function inhibitor is abciximab (also known as c7E3 Fab). Abciximab is a glycoprotein IIb/IIIa receptor antagonist and inhibits platelet aggregation. Additional non-limiting platelet function inhibitors include adenosine diphosphate (ADP) receptor inhibitors (e.g., clopidogrel, prasugrel, ticagrelor, ticlopidine), phosphodiesterase inhibitors (e.g., cilostazol) glycoprotein IIb/IIIa receptor inhibitors (e.g., abciximab, eptifibatide, and tirofiban), adenosine reuptake inhibitors (e.g., dipyridamole) and thromboxane inhibitors, including thromboxane synthase inhibitors and thromboxane receptor antagonists (e.g., tertroban). Any of these platelet function inhibitors (or combinations thereof) can be used in the methods described herein.

Platelet function inhibitors (including those listed above and combinations thereof) are well known and can be used at known concentrations to reduce platelet function in whole blood. In various embodiments, the platelet function inhibitor is administered to a blood sample (e.g., a whole blood sample) at a concentration of between about 2.5 ug/ml to about 250 ug/ml.

In some embodiments of the methods described herein, once a whole blood sample is collected from the patient, the blood may be treated in such a way to reduce platelet function in the sample (e.g., by physical manipulation or by contact with a platelet function inhibitor). For example, the whole blood can be placed into a single container already containing an inhibitor of platelet function. Or, an inhibitor of platelet function can be added to the container containing whole blood. Or, the whole blood can be platelet depleted (e.g., by physically removing platelets from the blood). Following reduction in platelet function, the blood sample can then be separated into the three viscoelastic assay test groups, with the first test being performed in the absence of the thrombolytic agent, the second test being performed in the presence of a low amount of the thrombolytic agent, and the third test being performed in the presence of a high amount of the thrombolytic agent.

Of course in some embodiments, the platelet function of the samples is reduced at the same time that the thrombolytic agent is added to. Thus, in some embodiments, when blood sample being tested is placed in a container (e.g., a cup or a cuvette), the platelet function inhibitor is in the container prior to addition of the blood sample. In some embodiments, the platelet function inhibitor coats the interior of the container such that it is in contact with the blood sample once the blood sample is placed into the container.

A functional fibrinogen assay using the thromboelastography (TEG) methodology is commercially available from Haemonetics, Corp. (Braintree, Mass., USA). This assay includes a platelet inhibitor and thus removes the contribution of platelets from the measurement of fibrinolysis. The use of this functional fibrinogen assay has described (see Harr et al., *Shock* 39(1): 45-49, 2013).

As described below, to detect fibrinolysis shutdown or latent hyperfibrinolysis at a very early stage, a functional fibrinogen (FF) assay (i.e., a TEG assay removing the contribution of platelets to the hemostasis process) may be used in addition to a standard TEG or TEM assay. As described above blood from a patient with fibrinolysis shutdown or latent hyperfibrinolysis will show a difference between the tracings in the presence of low amount of thrombolytic agent or in the presence of a high amount of the thrombolytic agent as compared to normal blood. These tracings (e.g., from TEG, TEM, or an FF assay) will allow determination of coagulation characteristic values reflective of the coagulation process and coagulation characteristic values reflective of the fibrinolysis process.

In another aspect, the invention provides a method for detecting latent hyperfibrinolysis or fibrinolysis shutdown in a patient, the method comprising subjecting a first blood sample from the patient to a viscoelastic analysis in the presence of a low amount of a thrombolytic agent, to obtain a low coagulation characteristic value of the patient; subjecting a second blood sample from the patient to a viscoelastic analysis in the presence of a high amount of a thrombolytic agent, to obtain a high coagulation characteristic value of the patient; comparing the low coagulation characteristic value of the patient to a low coagulation characteristic value of a healthy individual, the low coagulation characteristic value of the healthy individual obtained by subjecting a blood sample from a healthy individual to the viscoelastic analysis clotting assay in the presence of the low amount of the thrombolytic agent, and comparing the high coagulation characteristic value of the patient to a high coagulation characteristic value of a healthy individual, the high coagulation characteristic value of the healthy individual obtained by subjecting a blood sample from a healthy individual to the viscoelastic analysis clotting assay in the presence of the high amount of the thrombolytic agent, wherein a difference in the low coagulation characteristic value of the patient as compared to the low coagulation characteristic value of the healthy individual identifies the patent as having latent hyperfibrinolysis and wherein a difference in the low coagulation characteristic value of the patient as compared to the low coagulation characteristic value of the healthy individual identifies the patent as having fibrinolysis shutdown.

In another aspect, the invention provides a container adapted for detecting hyperfibrinolysis in a blood sample using viscoelastic analysis comprising an interior having a coating comprising a low amount of a thrombolytic agent. In another aspect, the invention provides a container adapted for detecting fibrinolysis shutdown in a blood sample using viscoelastic analysis comprising an interior having a coating comprising a high amount of a thrombolytic agent.

The container, of course, may further comprise a stabilizing agent (also called simply a stabilizer) for stabilizing the thrombolytic agent. Non-limiting stabilizing agent include EDTa, polymers (e.g., PEG), amino acids (e.g., glycine), preservatives (e.g., benzyl alcohol), surfactants (e.g., non-ionic surfactants such as Polysorbate 80, Polysorbate 20, Triton X010, Pluronic F127, and sodium dodecyl sulfate (SDS)), and sugar and sugar alcohols such as sucrose and trehalose.

In some embodiments, the container may be either the container that the viscoelastic analysis is performed in (typically known as the "cup" in the context of TEG and ROTEM devices, for example) or a separate container in which the blood sample and the fibrinolytic agent and other agents are mixed and incubated prior to performance of the assay.

In yet another aspect, the invention provides a cartridge comprising multiple containers for detecting aberrant fibrinolysis in a blood sample, wherein at least one of the containers comprises an interior having a coating comprising a low amount of a thrombolytic agent and at least one container comprises an interior having a coating comprising a high amount of the thrombolytic agent. In some embodiments, the containers in the cartridge lack a bottom surface.

It should be noted that although the thrombolytic agent may be coated onto the interior of a container or containers within a cartridge, the low amount or high amount of thrombolytic agent can easily be in pre-packaged form (e.g., as pills or tablets or drops) which can then be added to the container (or containers in a cartridge) at the same time as, before, or after the blood sample is added to the container. For the tPA-challenged TEG or the tPA-challenged TEM, the thrombolytic agent is simply added to the blood sample in the container before TEG or TEM is performed on the blood sample.

In some embodiments, the thrombolytic agent is single or double chain human tissue plasminogen activator (tPA), tPA from another species, alteplase, reteplase, tenecteplase, anistreplase, serokinase, streptokinase, urokinase, kallikrein, or any other upregulator of the plasmin/fibrinolytic system. In some embodiments, the thrombolytic agent is human single chain tissue plasminogen activator or human double chain tissue plasminogen activator. In some embodiments, the low amount is between about 1 ng/ml and about 100 ng/ml thrombolytic agent or between about 10 ng/ml and about 90 ng/ml thrombolytic agent. In some embodiments, the high amount is between 110 ng/ml and about 1200 ng/ml or between about 150 ng/ml and about 1000 ng/ml thrombolytic agent.

In some embodiments, the container is used in a viscoelastic analysis performed using a TEG thromboelastography analyzer system or in a ROTEM thromboelastometry analyzer system.

In some embodiments, the cartridge is used in a viscoelastic analysis performed using a TEG thromboelastography analyzer system or in a ROTEM thromboelastometry analyzer system.

The following examples are provided which are meant to illustrate but not limit the invention described herein.

Example 1: A Functional Fibrinogen TEG Assay with a Thrombolytic Agent

Briefly, citrated whole blood samples are obtained from trauma patients. Venipuncture is performed with a 21-gauge needle in an antecubital vein, and blood is collected into evacuated containers containing 3.2% citrate (e.g., a 3.5 mL plastic Vacutainers® containing 3.2% citrate).

The Functional Fibrinogen assay is purchased from Haemonetics Corp. (Niles, Ill., USA and Braintree, Mass., USA), and performed on the TEG® 5000 device according to manufacturer's instructions.

To perform the Functional Fibrinogen (FF) assay, 0.5 mL of citrated blood is added to the designated FF-vial containing a mixture of tissue factor (a coagulation activator) and the abciximab (a monoclonal GPIIb/IIIa receptor antagonist; sometimes referred to as the FF reagent), and the blood sample is gently mixed. A 340 uL aliquot is transferred from the FF-vial to a 37° C. TEG cup preloaded with 20 µL 0.2 mol/L of CaCl$_2$. The FF-assay measures the coagulation parameters of a platelet-free clot. A second 340 uL aliquot is transferred from the FF-vial to a 37° C. TEG cup preloaded with 20 µL 0.2 mol/L of CaCl$_2$, where the second TEG cup is coated with 75 ng/ml tissue plasminogen activator ("low amount of tPA"). A third 340 uL aliquot is transferred from the FF-vial to a 37° C. TEG cup preloaded with 20 µL 0.2 mol/L of CaCl$_2$, where the third TEG cup is coated with 150 ng/ml tissue plasminogen activator ("high amount of tPA").

The three portions of the blood sample (i.e., the FF without tPA, the FF plus the low amount of tPA, and the FF plus the high amount of tPA) are analyzed simultaneously on a TEG 5000 device. If the blood sample is normal, each of the samples will be identical to FF without tPA, the FF plus the low amount of tPA, and the FF plus the high amount of tPA samples of healthy individuals.

However, if the blood sample is taken from a patient who has latent hyperfibrinolysis, the low amount of tPA-treated portion of the blood sample will provide a TEG tracing that is markedly different than the TEG tracing a blood samples from a healthy individual also treated with the low amount of tPA. If the blood sample is taken from a patient who has fibrinolysis shutdown, the high amount of tPA-treated portion of the blood sample will provide a TEG tracing that is markedly different than the TEG tracing a blood samples from a healthy individual also treated with the high amount of tPA.

Example 2: A MultiChannel TEG Assay with a Thrombolytic Agent

For these studies, the protocol in Example 1 is followed, with citrated but no Functional Fibrinogen assay is performed.

Briefly, whole blood is collected from a patient brought in for surgery. Venipuncture is performed with a 21-gauge needle in an antecubital vein, and blood is collected into evacuated containers containing 3.2% citrate (e.g., a 3.5 mL plastic Vacutainers® containing 3.2% citrate).

The blood sample taken is divided into portions and loaded into TEG channels on a multichannel (and multi-container) cartridge as follows.

In the first channel, 340 uL of the citrated whole blood is loaded into a channel is preloaded with 20 µL 0.2 mol/L of CaCl$_2$ and run as a "citrated native" sample. Note that each of the channels and containers in the cartridge lacks a bottom surface.

Blood for loading the second and third channels are added to vials of lyophilized tPA, containing 37.5 and 75 ng of tPA respectively. Then 500 uL of citrated blood (i.e., from the Vacutainers that contained 3.2% citrate) are added to each of these two vials, resulting in a final concentration of tPA in the vials of 75 ng/ml and 150 ng/ml. The vials are gently inverted 10 times and then 340 uL of their contents are pipetted into the TEG cups of the 2nd and 3rd channels and these channels are also run as "citrated native" with the annotation added that the second channel contains tPA at a final concentration of 75 ng/mL and the third channel contains tPA at a final concentration of 150 ng/mL. Each of the second and third channels is channel is preloaded with 20 µL 0.2 mol/L of CaCl$_2$.

Figure 7:
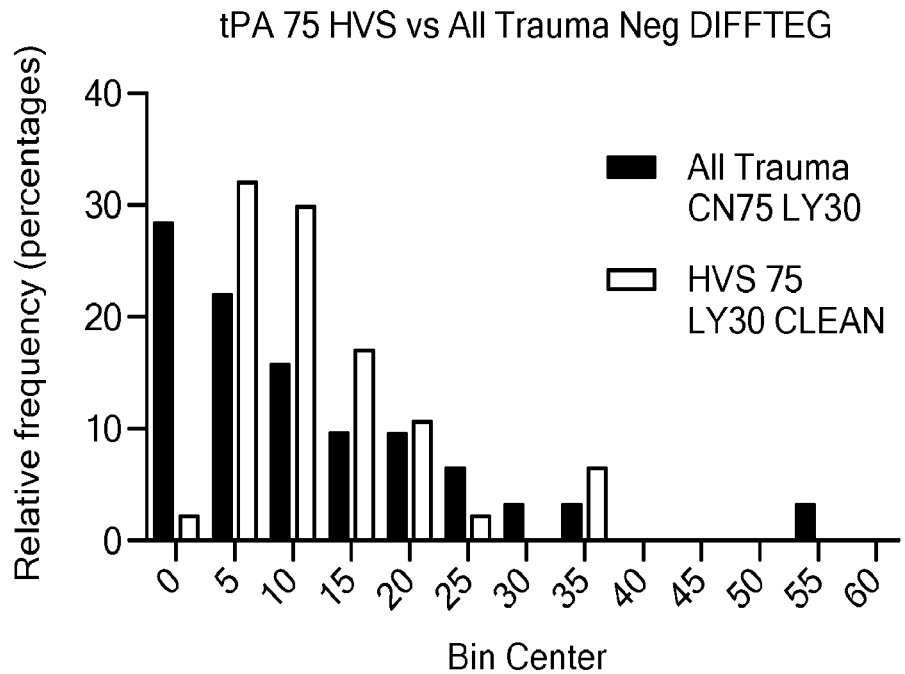
FIG. 7 is a bar graph showing the comparison of LY30 coagulation characteristic values of trauma patients (black bars) and healthy individuals (gray bars) as obtained through viscoelastic analysis in the presence of 75 ng/ml tPA.
Figure 8:
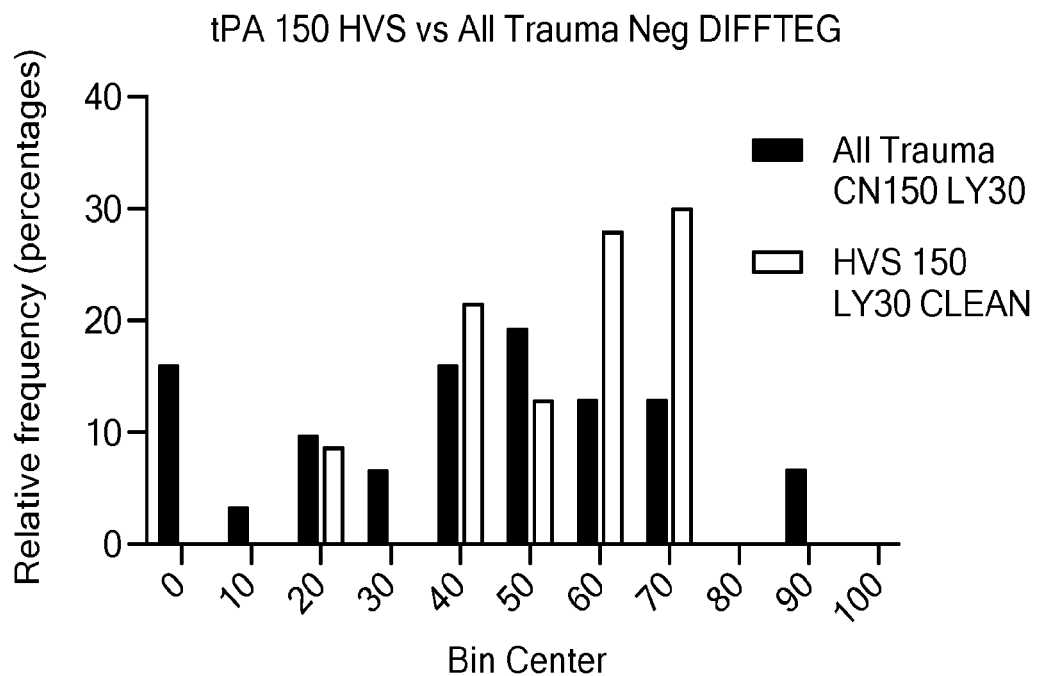
FIG. 8 is a bar graph showing the comparison of LY30 coagulation characteristic values of trauma patients (black bars) and healthy individuals (gray bars) as obtained through viscoelastic analysis in the presence of 150 ng/ml tPA.

The results are shown in Tables 1 and 1B and FIG. 7 (for low tPA of 75 ng/ml), and in Tables 2A and 2B and FIG. 8 (for high tPA of 150 ng/ml).

TABLE 1A

| | All Trauma patients LY30 with 75 ng/ml TPA | HVS (healthy individual volunteers) LY30 with 75 ng/ml TPA |
|---|---|---|
| Total number of values | 32 | 47 |
| Number of excluded values | 0 | 0 |
| Number of binned values | 32 | 47 |
| Minimum | 0 | 2.3 |
| 25% Percentile | 2.125 | 5.9 |
| Median | 7.15 | 10 |
| 75% Percentile | 17.025 | 15.3 |
| Maximum | 56.6 | 35.3 |
| Mean | 11.1 | 12.0489 |
| Std. Deviation | 12.2635 | 8.11196 |
| Std. Error of Mean | 2.1679 | 1.18325 |
| Lower 95% CI of mean | 6.67853 | 9.66718 |
| Upper 95% CI of mean | 15.5215 | 14.4307 |

TABLE 1B

| Bin Center | All Trauma LY30 with 75 ng/ml TPA | HVS (healthy individual volunteers) LY30 with 75 ng/ml TPA |
|---|---|---|
| 0 | 28.125 | 2.12766 |
| 5 | 21.875 | 31.91489 |
| 10 | 15.625 | 29.78723 |
| 15 | 9.375 | 17.02128 |
| 20 | 9.375 | 10.6383 |
| 25 | 6.25 | 2.12766 |
| 30 | 3.125 | 0 |
| 35 | 3.125 | 6.382979 |
| 40 | 0 | 0 |
| 45 | 0 | 0 |
| 50 | 0 | 0 |
| 55 | 3.125 | 0 |
| 60 | 0 | 0 |
| Total: 100% | | Total: 100% |

The results of Table 1B are graphically depicted in FIG. 7. Note that by "bin center" is meant a reflection of the average LY30 numbers of the samples in the particular bin. For example, in Table 1, 21.875% of trauma patients tested, where their samples were analyzed in the presence of 75 ng/ml tPA, had an average LY30 value of 5. In contrast, 31.915% of healthy individuals, where their samples were analyzed in the presence of 75 ng/ml tPA, had an average LY30 value of 5. This is the typical response of a trauma patient—samples from most patients analyzed in the presence of 75 ng/ml tPA will have a lower LY30 time than 75 ng/mml TPA-treated samples from a healthy individual.

However, there is a small subset of trauma patients whose blood samples, when analyzed in the presence of 75 ng/ml tPA, have a higher LY30 value than the LY30 values of healthy volunteers whose blood was analyzed in the presence of 75 ng/ml tPA. In FIG. 7, this sub population appears when the LY30 is 25 or higher. These trauma patients are likely to have latent hyperfibrinolysis and should be prophylactically administered a therapeutically relevant amount of a therapeutic agent that strengthens a blood clot or slows the dissolution of a blood clot such as an antifibrinolytic agent.

Tables 2A and 2B, and FIG. 8 show the LY30 numbers for TEG analysis in the presence of high (150 ng/ml) tPA in trauma patients and healthy individuals.

TABLE 2A

| | All Trauma LY30 with 150 ng/ml tPA | HVS (healthy individual volunteers) LY30 with 150 ng/ml tPA |
|---|---|---|
| Total number of values | 32 | 47 |
| Number of excluded values | 0 | 0 |
| Number of binned values | 32 | 47 |
| Minimum | 0 | 19.3 |
| 25% Percentile | 20 | 41.7 |
| Median | 45.5 | 57.2 |
| 75% Percentile | 59.125 | 66.2 |
| Maximum | 90.7 | 73.9 |
| Mean | 41.6625 | 53.4681 |
| Std. Deviation | 25.2437 | 14.3941 |
| Std. Error of Mean | 4.46249 | 2.09959 |
| Lower 95% CI of mean | 32.5612 | 49.2418 |
| Upper 95% CI of mean | 50.7638 | 57.6943 |

TABLE 2B

| Bin Center | All Trauma LY30 with 150 ng/ml tPA | HVS (healthy individual volunteers) LY30 with 150 ng/ml tPA |
|---|---|---|
| 0 | 15.625 | 0 |
| 10 | 3.125 | 0 |
| 20 | 9.375 | 8.510638 |
| 30 | 6.25 | 0 |
| 40 | 15.625 | 21.2766 |
| 50 | 18.75 | 12.76596 |
| 60 | 12.5 | 27.65957 |
| 70 | 12.5 | 29.78723 |
| 80 | 0 | 0 |
| 90 | 6.25 | 0 |
| 100 | 0 | 0 |

The results of Table 2B are graphically depicted in FIG. 8. As Tables 2A and 2B and FIG. 8 show, in the presence of 150 ng/ml tPA, the LY30 values of trauma patients are typically higher than the LY30 values from healthy individuals whose blood samples were run in a TEG assay with 150 ng/ml tPA. These individuals typically have LY30 values of above 40, and particularly above 60. These individuals have fibrinolysis shutdown and should be treated with a therapeutically relevant amount of a therapeutic agent that weakens a blood clot or speeds the dissolution of a blood clot to prevent thromboembolism events and other thrombus related injuries.

It is important to note that in this example, the patients were diagnosed based on their LY30 values. In other words, the patients were diagnosed thirty minutes after the MA time (maximum clot strength). As this point is typically reached less than 20 minutes after the viscoelastic analysis is started, the patient is diagnosed in less than 50 minutes. While that may seem like a long time, it is important to note that the latent hyperfibrinolysis and fibrinolysis shutdown conditions are commonly seen in apparently healthy individuals. If the patient was, in fact, a healthy individual, he or she may not be treated immediately, and may have to wait in the waiting room of the emergency room while other patients who are visibly not healthy individuals (e.g., elderly patients or children) are treated first. In some embodiments, the methods of the invention allow data to be collected when the patients immediately enter the emergency room, and provide the results within an hour of the start of the viscoelastic analysis.

Example 3. Comparison of TEG Tracings of Healthy Individuals and Apparently Healthy Individuals with Aberrant Fibrinolysis To highlight various embodiments of the invention, this Example 3 provides tracings from two patients from each of the following groups: healthy individuals (FIGS. 9A and 9B), fibrinolysis shutdown (FIGS. 10A and 10B), latent hyperfibrinolysis (FIGS. 11A and 11B), and, to provide a contrast to latent hyperfibrinolysis, regular (non-latent hyperfibrinolysis (FIGS. 12A-12B).

All of these studies were performed on a TEG 5000 Thrombelastograph system (commercially available from Haemonetics, Inc., Braintree, Mass.) using cups preloaded with 200 μL 0.2 mol/L of $CaCl_2$.

Figure 9A:
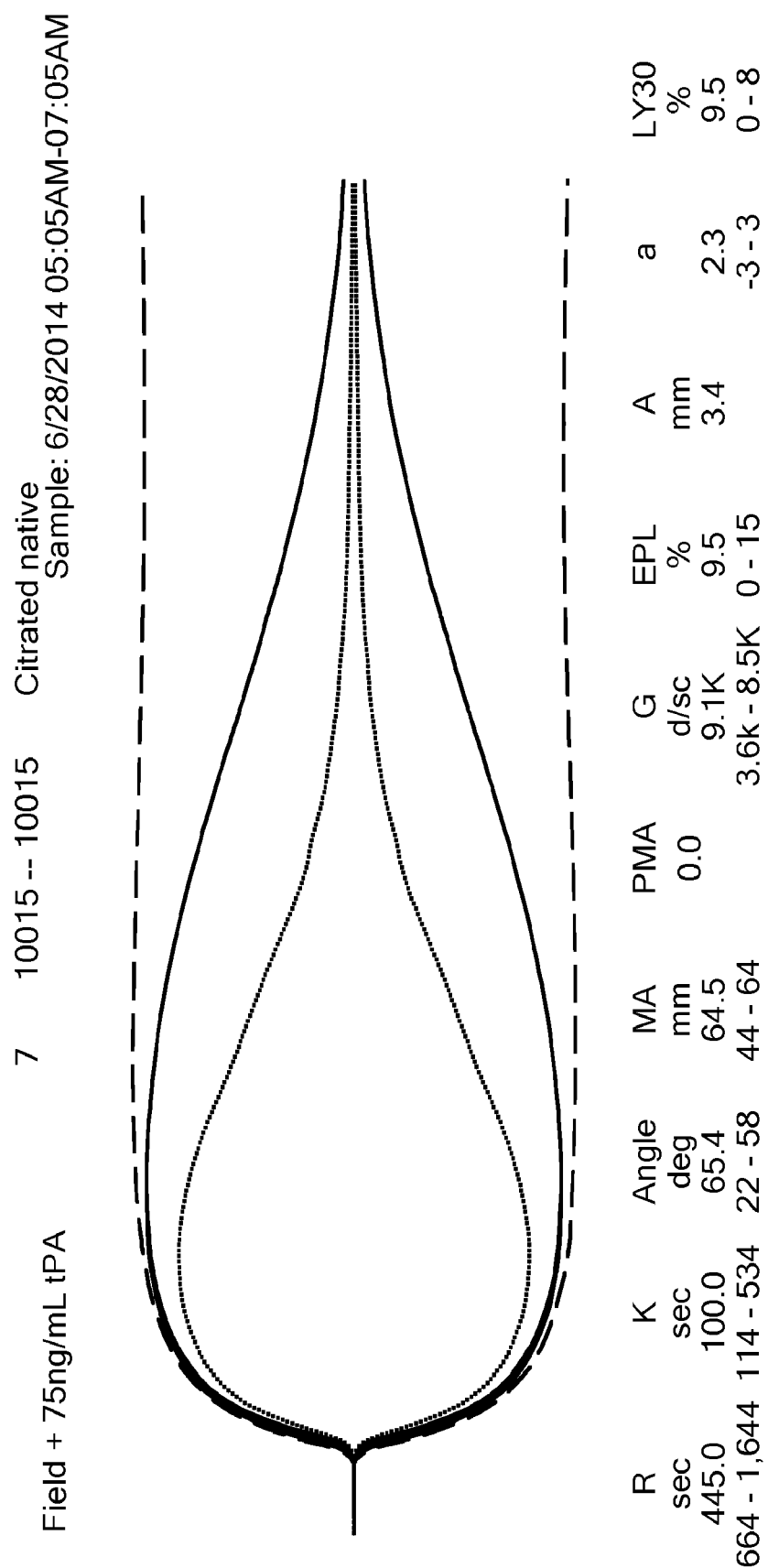
FIGS. 9A and 9B are TEG tracings from two healthy individuals, namely patient 15 (FIG. 9A) and patient 33 (FIG. 9B). The white lines in FIGS. 9A-9B are native TEG (on citrated whole blood), the green line is whole blood plus 75 ng/ml tPA, and the pink line is whole blood plus 150 ng/ml tPA. The values of the parameters shown below the tracings in FIG. 9A (e.g., R, K, MA, LY30, etc.) are the values from the sample of whole blood from healthy volunteer patient 15 plus 75 ng/ml tPA. The values of the parameters shown below the tracings in FIG. 9B (e.g., R, K, MA, LY30, etc.) are the values from the sample of whole blood from healthy volunteer patient 33 plus 75 ng/ml tPA.
Figure 9B:
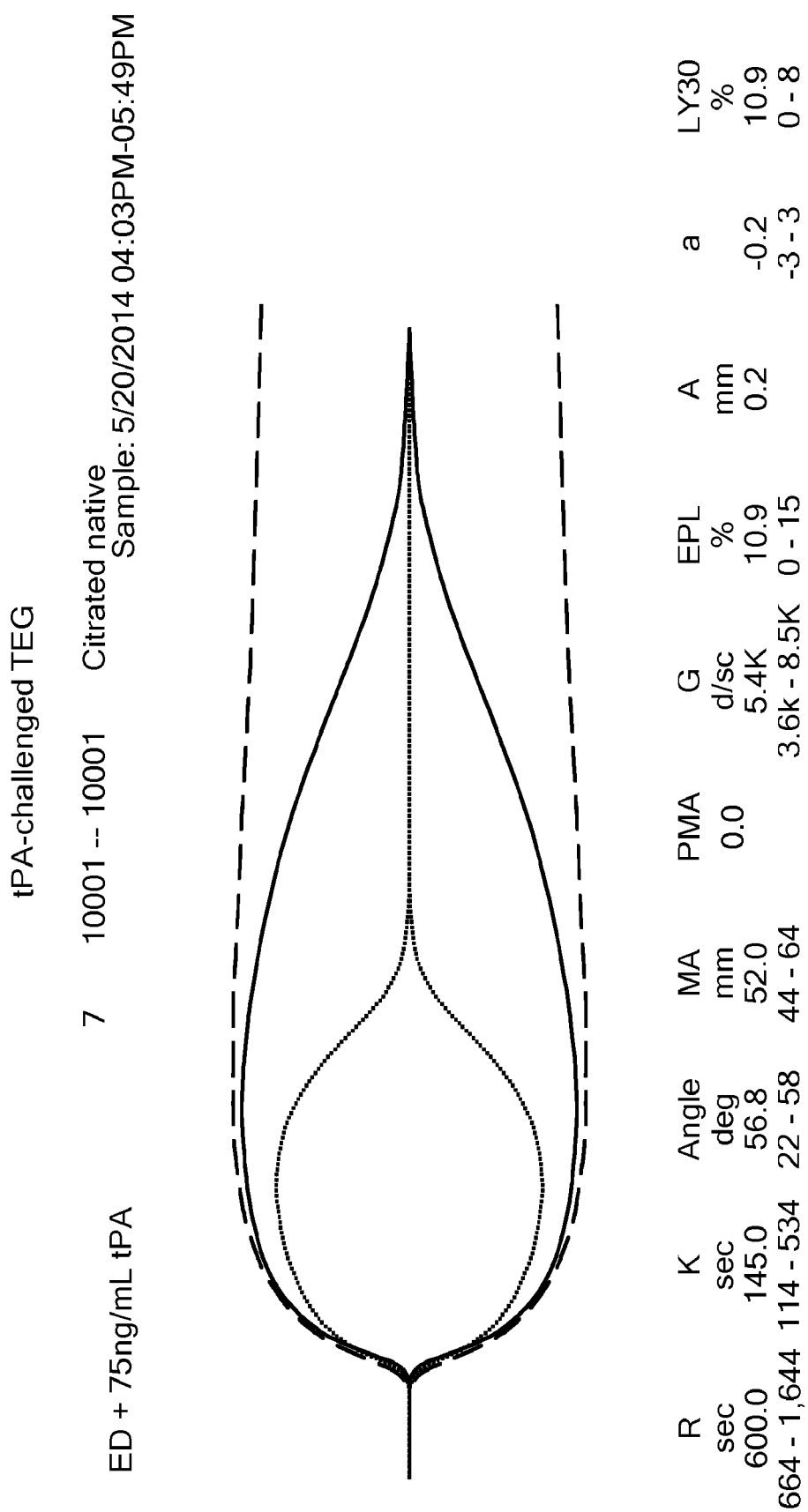

In FIGS. 9A and 9B, TEG tracings are shown from healthy individual patient 15 (FIG. 9A) and patient 33 (FIG. 9B). The white lines in FIGS. 9A-9B are native TEG (i.e., on citrated whole blood), the green line is whole blood plus 75 ng/ml tPA, and the pink line is whole blood plus 150 ng/ml tPA. As can be seen in both FIG. 9A and FIG. 9B, in healthy individuals, no fibrinolysis (or very little) is seen in untreated whole blood. When the blood is treated with 75 ng/ml tPA (green line), fibrinolysis occurs at a moderate pace. This pace of fibrinolysis dramatically increases in the presence of 150 ng/ml tPA (pink line). For a more detailed explanation of the TEG profile of healthy volunteer patient 33, please see Example 9 below and FIG. 40.

Figure 10A:
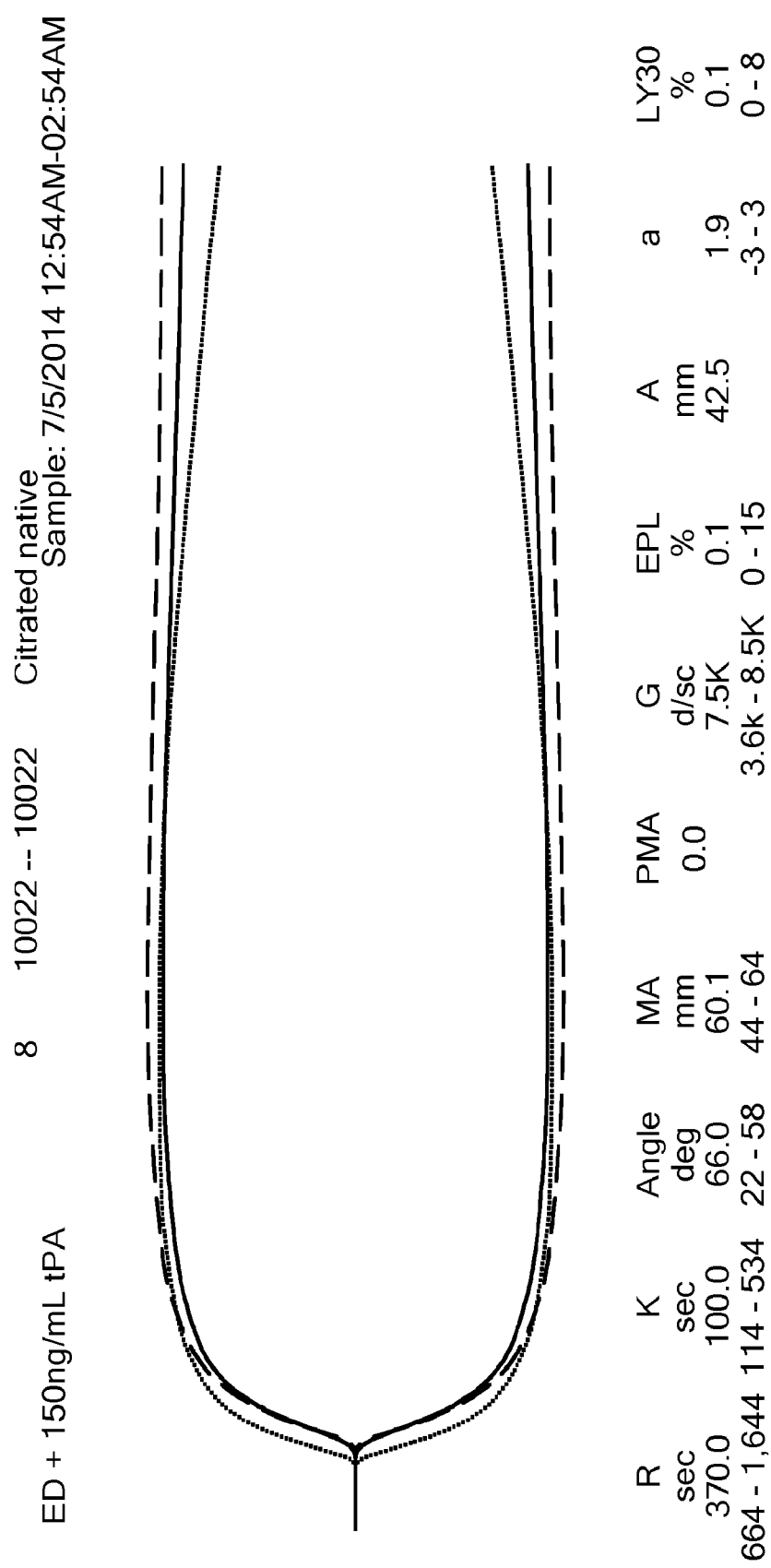
FIGS. 10A and 10B are TEG tracings from two individuals with fibrinolysis shutdown, namely patient 22 (FIG. 10A) and patient 38 (FIG. 10B). The white lines in FIGS. 10A-10B are native TEG (on citrated whole blood), the green line is whole blood plus 75 ng/ml tPA, and the pink line is whole blood plus 150 ng/ml tPA. The values of the parameters shown below the tracings in FIG. 10A (e.g., R, K, MA, LY30, etc.) are the values from the sample of whole blood from healthy volunteer patient 22 plus 150 ng/ml tPA. The values of the parameters shown below the tracings in FIG. 10B (e.g., R, K, MA, LY30, etc.) are the values from the sample of whole blood from healthy volunteer patient 38 plus 150 ng/ml tPA.
Figure 10B:
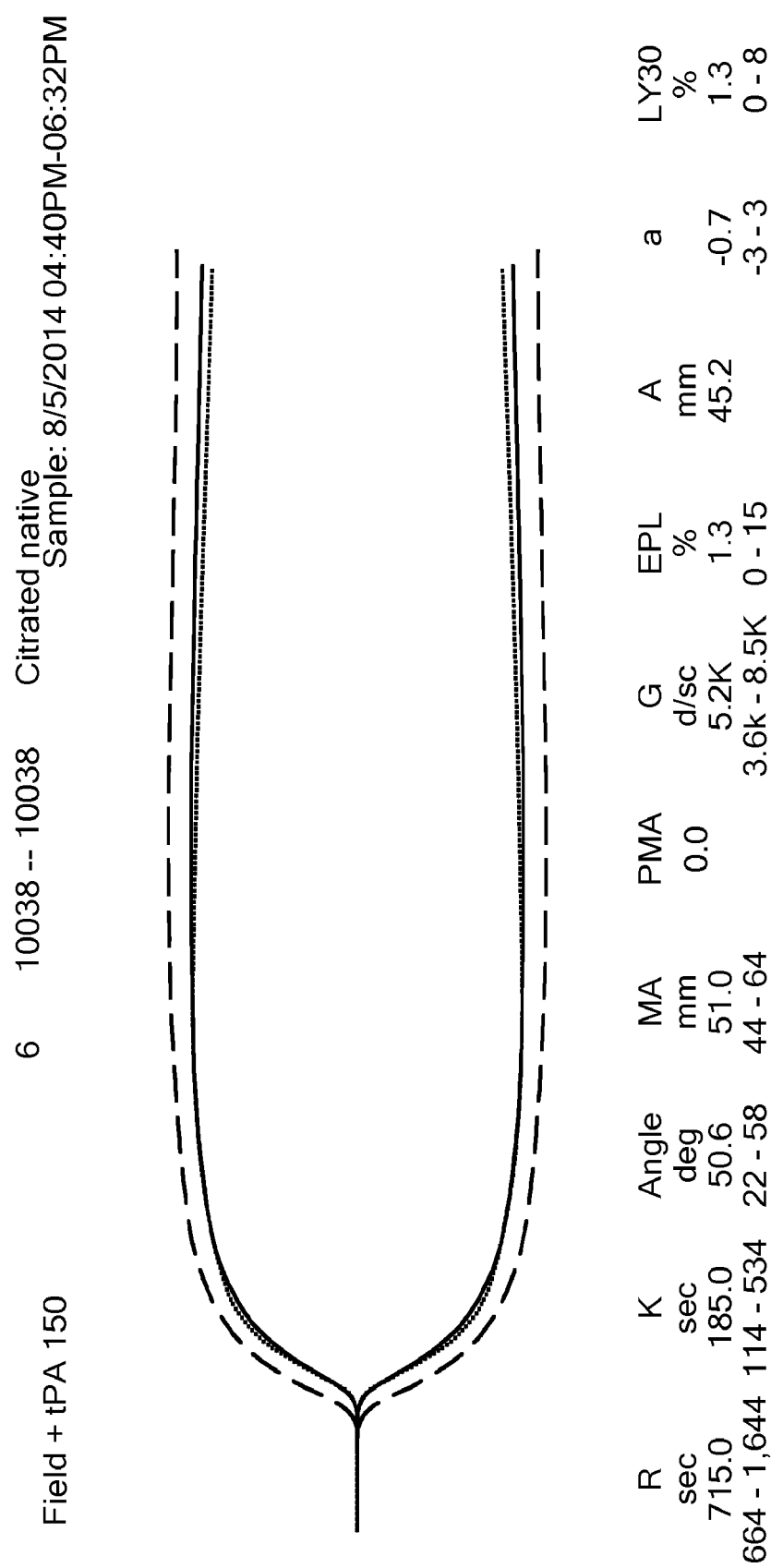

In FIGS. 10A and 10B, TEG tracings are shown from fibrinolysis shutdown patient 22 (FIG. 10A) and patient 38 (FIG. 10B). The white lines in FIGS. 10A-10B are native TEG (i.e., on citrated whole blood), the green line is whole blood plus 75 ng/ml tPA, and the pink line is whole blood plus 150 ng/ml tPA. As can be seen in both FIG. 10A and FIG. 10B, in patients with fibrinolysis shutdown, no fibrinolysis occurs, not even in the presence of a high amount of the thromolytic agent, tPA. If these patients are not immediately treated with a therapeutically relevant amount of tPA (or another therapeutic agent that weakens a blood clot or speeds the dissolution of a blood clot), they are in danger of organ failure from a thrombus blocking blood supply to the organ and/or a thromboembolism event (e.g., a pulmonary embolism if in the lung or a stroke if in the brain).

Figure 11A:
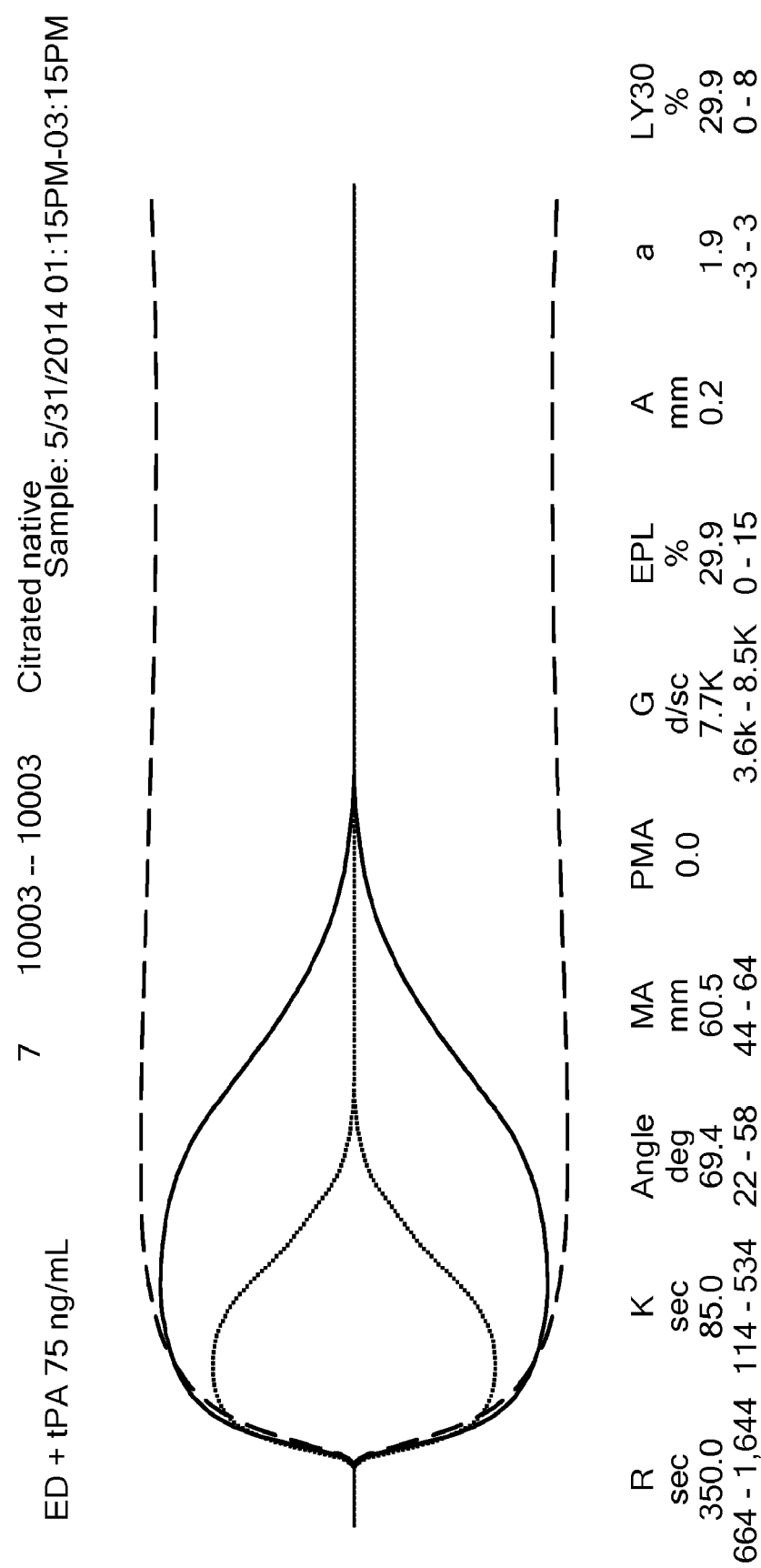
FIGS. 11A and 11B are TEG tracings from two individuals with latent hyperfibrinolysis, namely patient 3 (FIG. 11A) and patient 24 (FIG. 11B). The white lines in FIGS. 11A-11B are native TEG (on citrated whole blood), the green line is whole blood plus 75 ng/ml tPA, and the pink line is whole blood plus 150 ng/ml tPA. The values of the parameters shown below the tracings in FIG. 11A (e.g., R, K, MA, LY30, etc.) are the values from the sample of whole blood from patient 3 plus 75 ng/ml tPA. The values of the parameters shown below the tracings in FIG. 11B (e.g., R, K, MA, LY30, etc.) are the values from the sample of whole blood from patient 24 plus 75 ng/ml tPA.
Figure 11B:
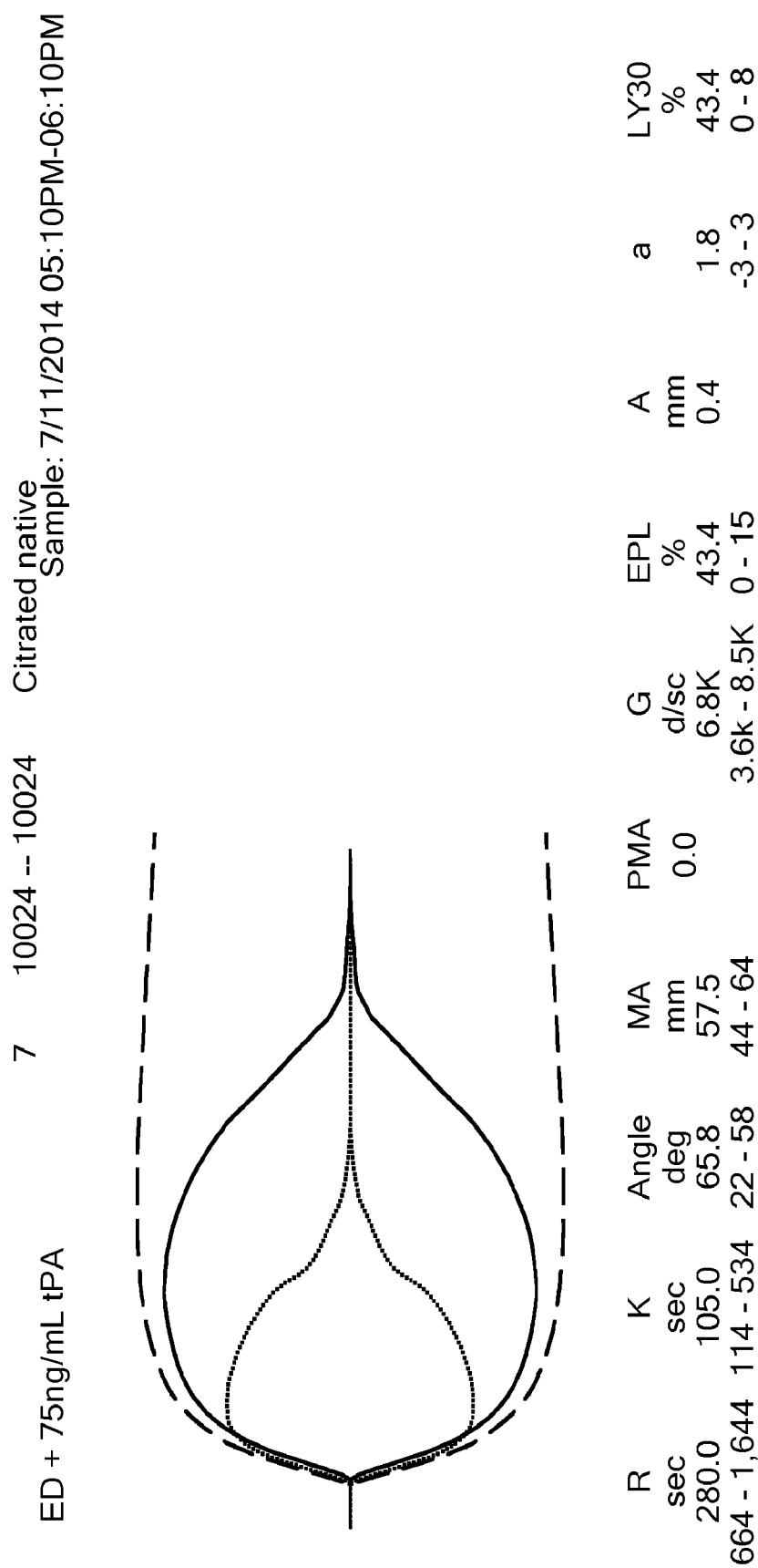
Figure 12A:
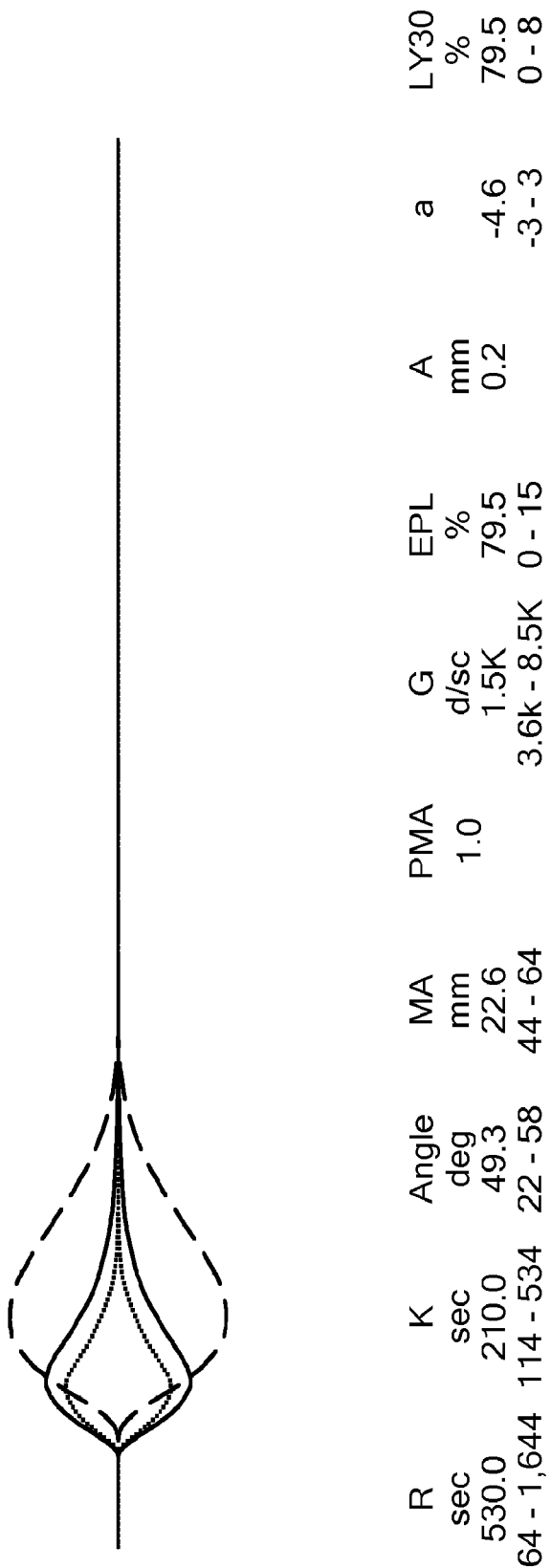
FIGS. 12A and 12B are TEG tracings from two individuals with classic (or overt) hyperfibrinolysis, namely patient 4 (FIG. 12A) and patient 36 (FIG. 12B). The white lines in FIGS. 12A-12B are native TEG (on citrated whole blood), the green line is whole blood plus 75 ng/ml tPA, and the pink line is whole blood plus 150 ng/ml tPA. The values of the parameters shown below the tracings in FIG. 12A (e.g., R, K, MA, LY30, etc.) are the values from the sample of whole blood from patient 4 plus 75 ng/ml tPA. The values of the parameters shown below the tracings in FIG. 12B (e.g., R, K, MA, LY30, etc.) are the values from the sample of whole blood from patient 36 plus 75 ng/ml tPA.
Figure 12B:
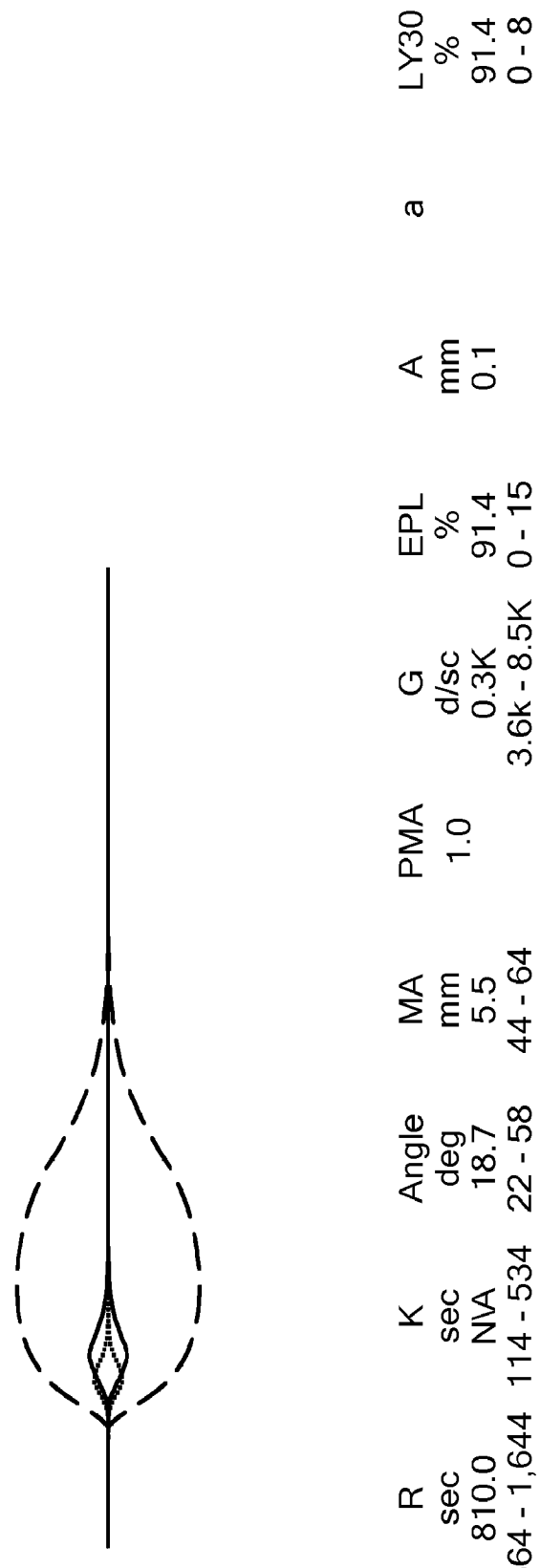

In FIGS. 11A and 11B, TEG tracings are shown from latent hyperfibrinolysis patient 3 (FIG. 11A) and patient 24 (FIG. 11B). The white lines in FIGS. 11A-11B are native TEG (i.e., on citrated whole blood), the green line is whole blood plus 75 ng/ml tPA, and the pink line is whole blood plus 150 ng/ml tPA. As can be seen in both FIG. 11A and FIG. 11B, in patients with latent hyperfibrinolysis, fibrinolysis occurs rapidly even with a low amount of a thrombolytic agent (i.e., 25 ng/ml tPA, green lines), and in the presence of high amount of 150 ng/ml tPA (pink lines), the clots dissolve so rapidly that they are effectively useless. If these patients are not immediately treated with a therapeutically relevant amount of a therapeutic agent that strengthens a blood clot or slows the dissolution of a blood clot (e.g., tranexamic acid), they are in danger of bleeding to death. Note that when the blood samples of these latent hyperfibrinolysis patients are not analyzed in the presence of tPA, their blood clots do not dissolve (see white lines in FIGS. 11A and 11B).

Finally, in FIGS. 12A and 12B, TEG tracings are shown from patients with classic (or overt) hyperfibrinolysis, namely patient 4 (FIG. 12A) and patient 36 (FIG. 12B). The white lines in FIGS. 12A-12B are native TEG (e.g., on citrated whole blood), the green line is whole blood plus 75 ng/ml tPA, and the pink line is whole blood plus 150 ng/ml tPA. As can be seen in both FIG. 12A and FIG. 12B, in patients with overt hyperfibrinolysis, fibrinolysis occurs without the addition of any tPA to the blood samples of these patients. When a low amount of a thrombolytic agent (e.g., 25 ng/ml tPA; green lines) is added, fibrinolysis occurs more quickly, and occurs more quickly still in the presence of a high amount of the thrombolytic agent (e.g., 150 ng/ml tPA; pink lines).

Note that for the patients identified as having fibrinolysis shutdown (FIGS. 10A and 10B) their blood samples can be tested using the TEG assay in the presence of varying amount of tPA to tailor the amount of tPA required to promote dissolution of their blood clots. For example, both patient 22 (FIG. 10A) and patient 38 (FIG. 10B) have clots that are not responding to 150 ng/mL tPA. Using the assays described herein, the concentration of tPA can be increased to find the concentration of tPA required to break down their clot in vitro in the TEG assay. The patients can then be administered this amount of tPA systemically to dissolve blood clots in vivo and thereby prevent the poor outcomes associated with blood clots. Some patients who would benefit from such tailoring of tPA therapy include, without limitation, patients with disease conditions including deep vein thrombosis (DVT), pulmonary embolism (PE), myocardial infarction (MI) or ischemic stroke.

Example 4: Identifying Apparently Healthy Individuals Who Benefit from the Methods Described Herein This Example 4 provides a hypothetical example to show a realistic use of some embodiments of the invention. In this hypothetical example, patients of various ages are brought into a hospital emergency room following a highway crash involving two buses, one carrying forty senior citizens and the other carrying forty student members of the orchestra of a local university. The average age of the senior citizens is 60 years. The average age of the students is 19 years. Both genders are represented equally in both buses.

Given the differences in their ages, the patients are triaged such that the senior citizens are given a higher priority for urgent care. However, TEG tracings in the presence of a low amount of a thrombolytic agent (e.g., 75 ng/ml tPA) and in the presence of a high amount of a thrombolytic agent (e.g., 150 ng/ml tPA) are obtained on all twenty students. As news of the accident spreads to the university, classmates and friends of the students arrive at the emergency room. TEG tracings in the presence of 75 ng/ml TPA and in the presence of 150 ng/ml tPA are obtained from the uninjured students. The average age of the uninjured students is 19 years.

Most of the injured orchestra students are have TEG tracings in the presence of 75 ng/ml TPA and in the presence of 150 ng/ml tPA that are substantively the same as the majority of the TEG tracings in the presence 75 ng/ml TPA and in the presence of 150 ng/ml tPA of the uninjured students. Most of these uninjured students are thus healthy individuals as the term is used herein.

However, two injured orchestra students are found have TEG tracings in the presence of 75 ng/ml tPA that are different from the TEG tracings in the presence of 75 ng/ml tPA of the uninjured students. The LY30 numbers of these two students are higher than the LY30 numbers of the uninjured students. One of these two students is immediately treated with transexamic acid. She makes a full recovery. The aberrant TEG tracing of the second of these two students is unfortunately overlooked. Consequently he not treated with transexamic acid. He has seems fine in the emergency waiting room, but then suddenly bleeding at his surface wounds increases and he shows the hallmarks of internal bleeding (e.g., light headedness, abdominal pain, headache). By the time the emergency room staff is alerted to his sudden turn for the worse, he dies.

Additionally, two injured orchestra are found have TEG tracings in the presence of 150 ng/ml tPA that are different from the TEG tracings in the presence of 150 ng/ml tPA of the uninjured students. The LY30 numbers of these two students are lower than the LY30 numbers of the uninjured students. One of the students is immediately treated with a therapeutic agent that weakens a blood clot or speeds the dissolution of a blood clot such as an anticoagulant (e.g., dabigatran) and makes a full recovery. The other of the two students is overlooked. By the time her abnormal TEG tracing is noticed, the large blood clots in her body have reduced blood supply to one of her kidneys. She survives but her kidney is permanently injured as a result.

This hypothetical example shows that using some of the methods described herein, four of the injured orchestra students are apparently healthy individuals who are not, however, healthy individuals. However, because of their youth, they are overlooked in the emergency room. Their aberrant TEG tracing in the presence of are found have TEG tracings in the presence of 75 ng/ml tPA or 150 ng/ml tPA as compared to the TEG tracings of in the presence of 75 ng/ml tPA or 150 ng/ml tPA of healthy individuals identify these four patients as apparently healthy individuals with aberrant fibrinolysis. As described herein, if a patient with latent hyperfibrinolysis is immediately treated with a therapeutic agent that strengthens a blood clot or slows the dissolution of a blood clot such as an antibrinolytic agent (e.g., tranexamic acid), that patient may make a full recovery but if not treated, that patient may die. Similarly, if a patient with fibrinolysis shutdown is immediately treated with a therapeutic agent that weakens a blood clot or speeds the dissolution of a blood clot such as an anticoagulant (e.g., dabigatran), that patient may make a full recovery, but if not treated, that patient may suffer permanent injury or may die.

Example 5: Identifying Individuals with End-Stage Renal Disease Who May Benefit from Graft Introduction: Patients in end-stage renal disease (ESRD) display various derangements of coagulation. A mixed pattern of hypo- and hypercoagulability can be found in these patients, with a paradoxical prolongation of the enzymatic phase of clot formation followed by rapid clot growth and elevated final clot strength. This example was performed to clarify the detailed features of the hypercoagulable component of the coagulopathy of ESRD to develop targets for prophylactic therapy aimed at prevention of dialysis access graft thrombosis.

Methods: Blood was collected from 16 consecutive ESRD human patients at the time of dialysis access construction and compared to that of 53 healthy individuals (volunteers) using multichannel thromboelastography (TEG). Rapid TEG and the Functional Fibrinogen (platelet-inhibited) TEG were used to assess clot strength and the relative contributions of platelets and fibrinogen. tPA-challenged TEG was used to assess fibrinolysis susceptibility, using the coagulation characteristic at 30 minutes (LY30) parameter of TEG, when the sample is challenged with exogenous tPA (e.g., at two doses, one at 75 ng/ml human single-chain tPA and one at 150 ng/ml human single-chain tPA. Platelet function was assessed by aggregometry and TEG platelet mapping.

Results: Overall clot strength, measured by Rapid TEG maximum amplitude (MA), was elevated at 71±6 mm in ESRD patients compared to 66±4 for healthy controls (p=0.0005, two-tailed Mann-Whitney test). Functional fibrinogen level (by platelet-inhibited TEG MA) was even more markedly elevated at 32 (IQR 29-37) mm in ESRD patients versus 20 (IQR 17-22) mm for controls (p<0.0001). ESRD patients also displayed increased resistance to fibrinolysis, with a tPA-challenged TEG LY30 of 29% (IQR 15-39%) compared to 56% (IQR 40-65%) for healthy controls (p=0.0004) at the high dosage of tPA (i.e., 150 ng/ml tPA). Platelet function tests on ESRD patients were within normal limits. The ESRD patients were resistant to both low dose and high dose tPA, showing that they are in fibrinolysis shutdown.

Conclusion: Hyperfibrinogenemia (i.e., latent hyperfibrinolysis) and impaired fibrinolysis (i.e., fibrinolysis shutdown) are responsible for the hypercoagulability observed in ESRD and may contribute to graft/fistula thrombosis. As enzymatic clotting is already prolonged in ESRD and platelet function is generally normal, traditional agents such as heparin or aspirin are of limited prophylactic benefit in prevention of graft/fistula thrombosis. Antifibrinolytic therapeutic agents affecting fibrin clot strength and promoting fibrinolysis (e.g., factor XIIIa inhibitors, tranexamic acid (TXA), PAI-1 antagonists or low dose thrombolytics such as tissue plasminogen activator (tPA)) may therefore be of greater utility for preservation of dialysis access.

The results of this Example 5 show that in TEG analysis in the presence of a high amount of a thrombolytic agent (e.g., 150 ng/ml of tPA), blood samples from ESRD patients have a lower LY30 value than blood samples from healthy individuals. In some embodiments of the present invention, these ESRD patients are identified as likely to have (or already have) fibrinolysis shutdown. These ESRD patients may benefit from prophylactic administration of a therapeutically relevant amount of a therapeutic agent that weakens a blood clot or speeds the dissolution of a blood clot (e.g., PAI-1 antagonists, inhibitors of Factor XIIIa, tPA, heparin, warfarin, direct thrombin inhibitors (e.g., dabigatran), and Factor Xa inhibitors (e.g., apixaban).

Example 6: Determination of Low and High Dose tPA Averages for Healthy Individuals These studies were performed to determine average LY30 values for healthy individuals whose blood samples were treated with either 75 ng/ml tPA or 150 ng/ml tPA For the 75 ng/ml tPA, blood samples of 150 healthy volunteers were tested. The minimum LY30 was 0.7. The 25% percentile LY30 value was 5.875. The median LY30 value was 8.6. The 75% percentile LY30 value was 12.3. And the maximum LY30 was 52.9. For these healthy individuals whose blood samples were tested in the presence of 75 ng/ml tPA, the mean LY30 value was 10.987 with a standard deviation of 7.565 and a standard error of mean of 0.6177. The lower 95% CI of the mean was 8.97813 and the upper 95% CI of the mean was 11.4192.

Figure 13A:
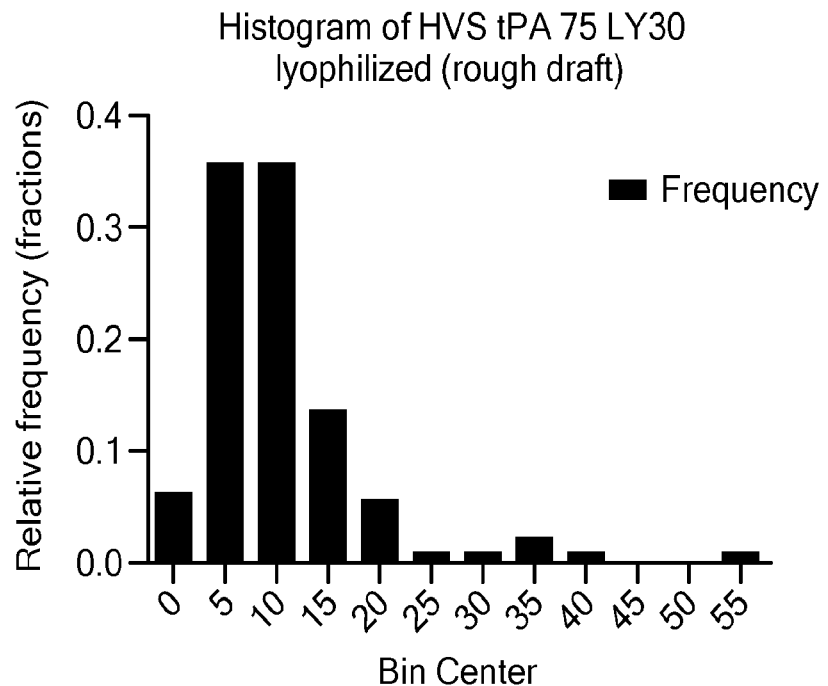
FIGS. 13A and 13B are bar graph showing the frequency of LY30 values in blood samples taken from healthy volunteers, where the samples were analyzed in the presence of 75 ng/ml tPA (FIG. 13A) or in the presence of 150 ng/ml tPA (FIG. 13B).

FIG. 13A shows the frequency of the LY30 numbers of blood samples of healthy volunteers in the presence of 75 ng/ml tPA. As mentioned above, the bins are a reflection of the average LY30 value of the samples in the particular bin. For example, all the samples with an LY30 value closest to 5 will be put into bin 5. As can be seen in FIG. 13A, bins 5 and 10 (i.e., LY30 numbers of 5 and 10) had the highest frequency.

For the 159 ng/ml tPA, blood samples of 115 healthy volunteers were tested. The minimum LY30 was 5.8. The 25% percentile LY30 value was 40.1. The median LY30 value was 53.5. The 75% percentile LY30 value was 62.4. And the maximum LY30 was 73.9. For these healthy individuals whose blood was tested in the presence of 150 ng/ml tPA, the mean LY30 value was 49.7 with a standard deviation of 16.8592 and a standard error of mean of 1.572. The lower 95% CI of the mean was 46.5865 and the upper 95% CI of the mean was 52.8152.

Figure 13B:
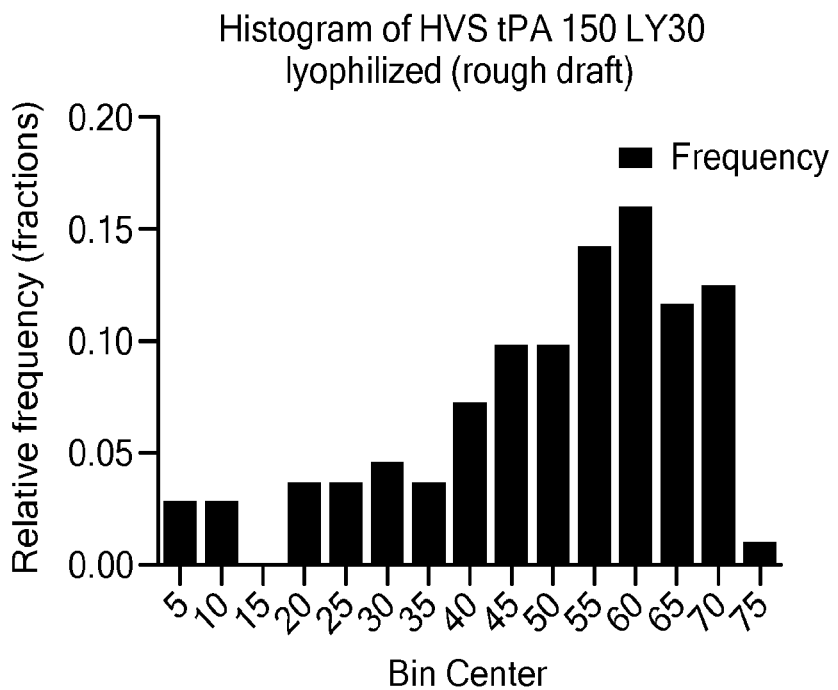

FIG. 13B shows the frequency of the LY30 numbers of blood samples of healthy volunteers in the presence of 150 ng/ml tPA. As can be seen in FIG. 13B, bins 55 and 60 (i.e., LY30 numbers of 55 and 60) had the highest frequency), although the majority of blood samples from the healthy individuals had LY30 values of between 50 and 70 in the presence of 150 ng/ml tPA.

Example 7: Production of Containers and Cartridges Containing a Low Amount of tPA and a High Amount of tPA Human single chain tissue plasminogen activator (tPA) was obtained from Molecular Innovations (Novi, Mich.). This was used to make individual 500 ul vials, where each vial contained either 37.5 ng tPA or 75 ng tPA. Following the addition of 500 ul. Lyophilized in a proprietary mixture.

The 37.5 ng tPA-containing 500 ul vials and the 75 ng tPA-containing 500 ul were made as follows:

Human single chain tPA is mixed with 25 ul of 30 mM Tris-HCl, 50 mM NaCl, pH7.4 with 1% BSA. The tPA is lyophilized and placed into the vials, such that either 37.5 ng or 75 ng is placed into each 500 ul vial. In some embodiments, the lyophilized tPA is coated onto the inner walls of the vial.

Upon addition of 500 ul (i.e., 0.5 ml) of a blood sample (e.g., whole blood, or plasma), the concentration of tPA in the vial containing 37.5 ng tPA is 75 ng/ml tPA and the concentration of tPA in the vial containing 75 ng tPA is 150 ng/ml tPA.

Of course, other concentrations of tPA can easily be achieved using vials or other containers or cartridges containing different amounts of tPA.

Once the blood sample is added to the vial, the tPA can be mixed into the blood sample by inverting the vial. The vial may be a TEG cup, for example. In another embodiments, the mixed contents of the vial (i.e., tPA mixed with the blood sample) can be transferred to a TEG container or a TEG cartridge.

For example, 340 ul of the mixed contents of the vial can be transferred to a 37° C. TEG cup preloaded with 20 μL 0.2 mol/L of $CaCl_2$. The TEG analysis can then be performed on the sample loaded into the TEG cup.

Example 8: Hyperfibrinolysis

Figure 14:
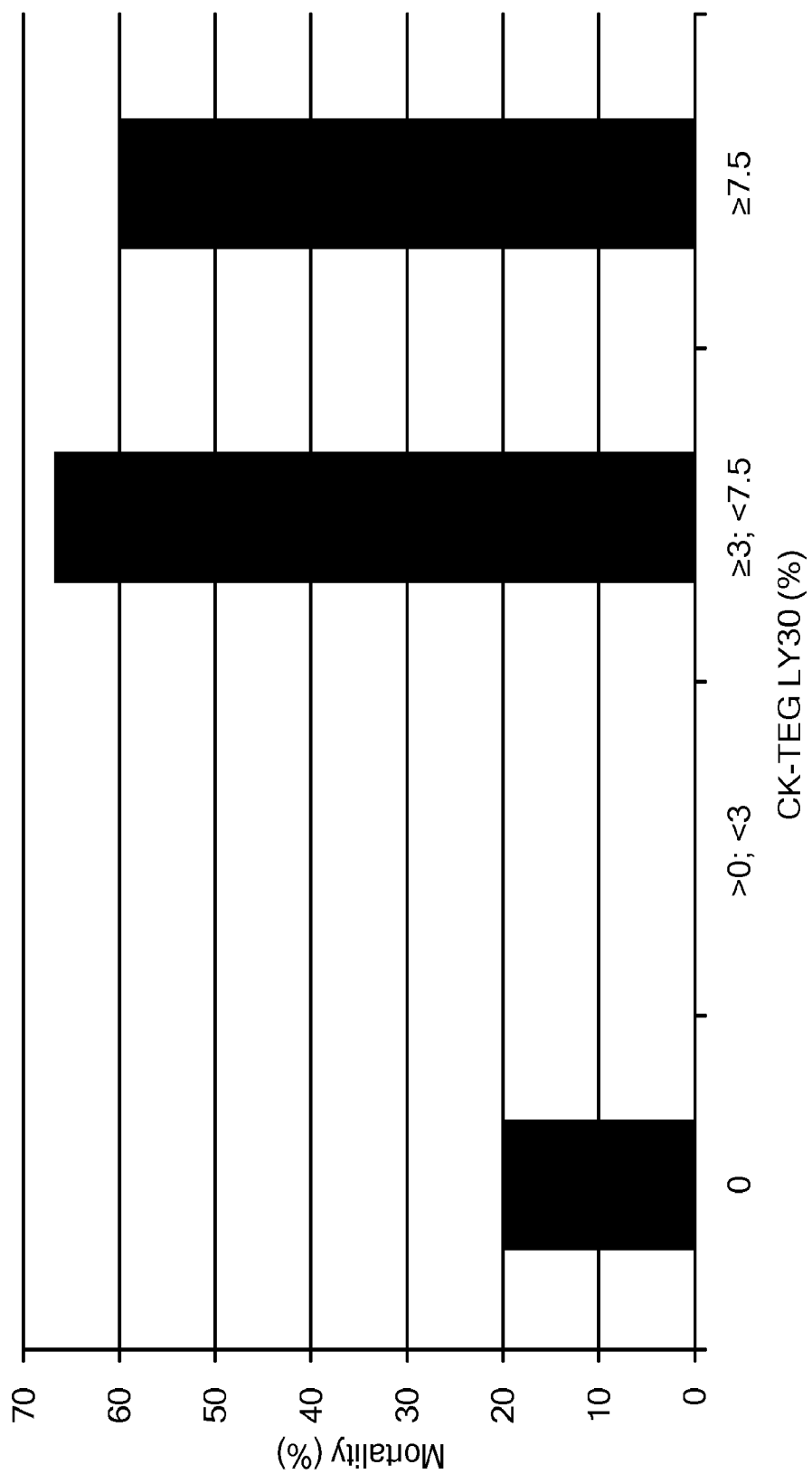
FIG. 14 is a bar graph showing the high mortality rate of systemic fibrinolysis.
Figures 15A, 15B:
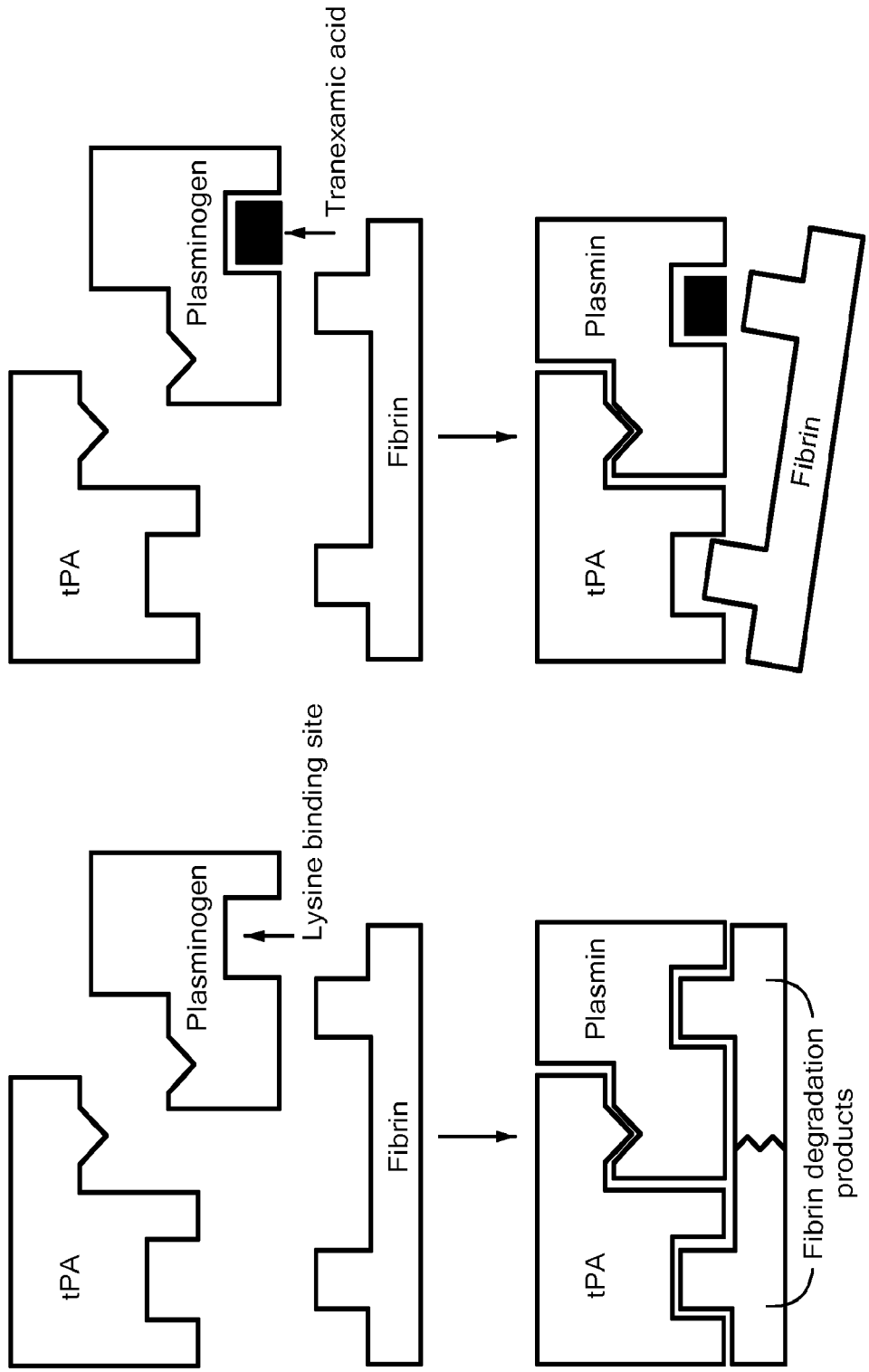
FIGS. 15A-15B are schematic diagrams showing the tPA/plasmin system without TXA (FIG. 15A) or with TXA (FIG. 15B).

Systemic hyperfibrinolysis is a critical component of trauma induced coagulopathy (TIC) and is highly lethal—it is associated with a mortality rate of up over 60% (FIG. 14). As schematically depicted in FIG. 15, the detailed molecular mechanisms of this pathology remain to be elucidated, but hyperfibrinolysis in trauma is known to be chiefly driven by the tPA/plasmin system, as proven by the its reversibility with tranexamic acid (TXA).

Figure 16:
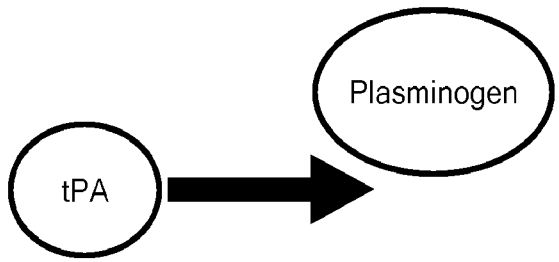
FIGS. 16-18 are schematic diagrams showing the interaction of tPA and PAI-1, and the role that PAI-1 plays as a cognate inhibitor of tPA.
Figure 17:
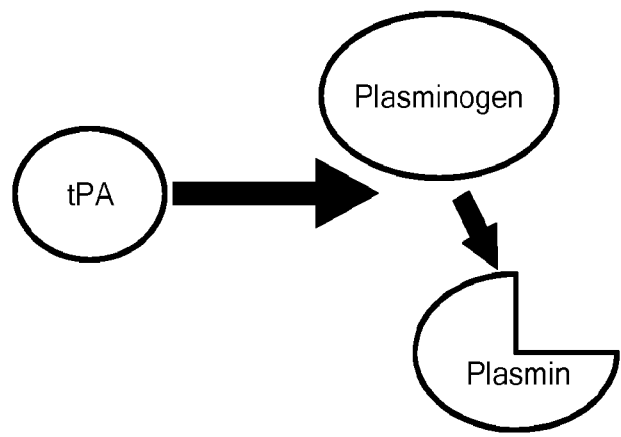
Figure 18:
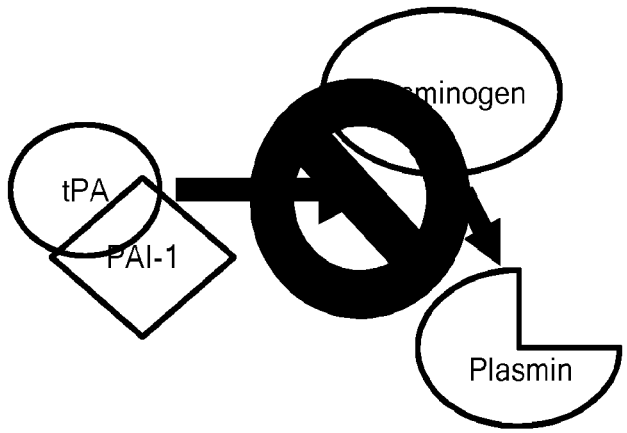
Figure 19:
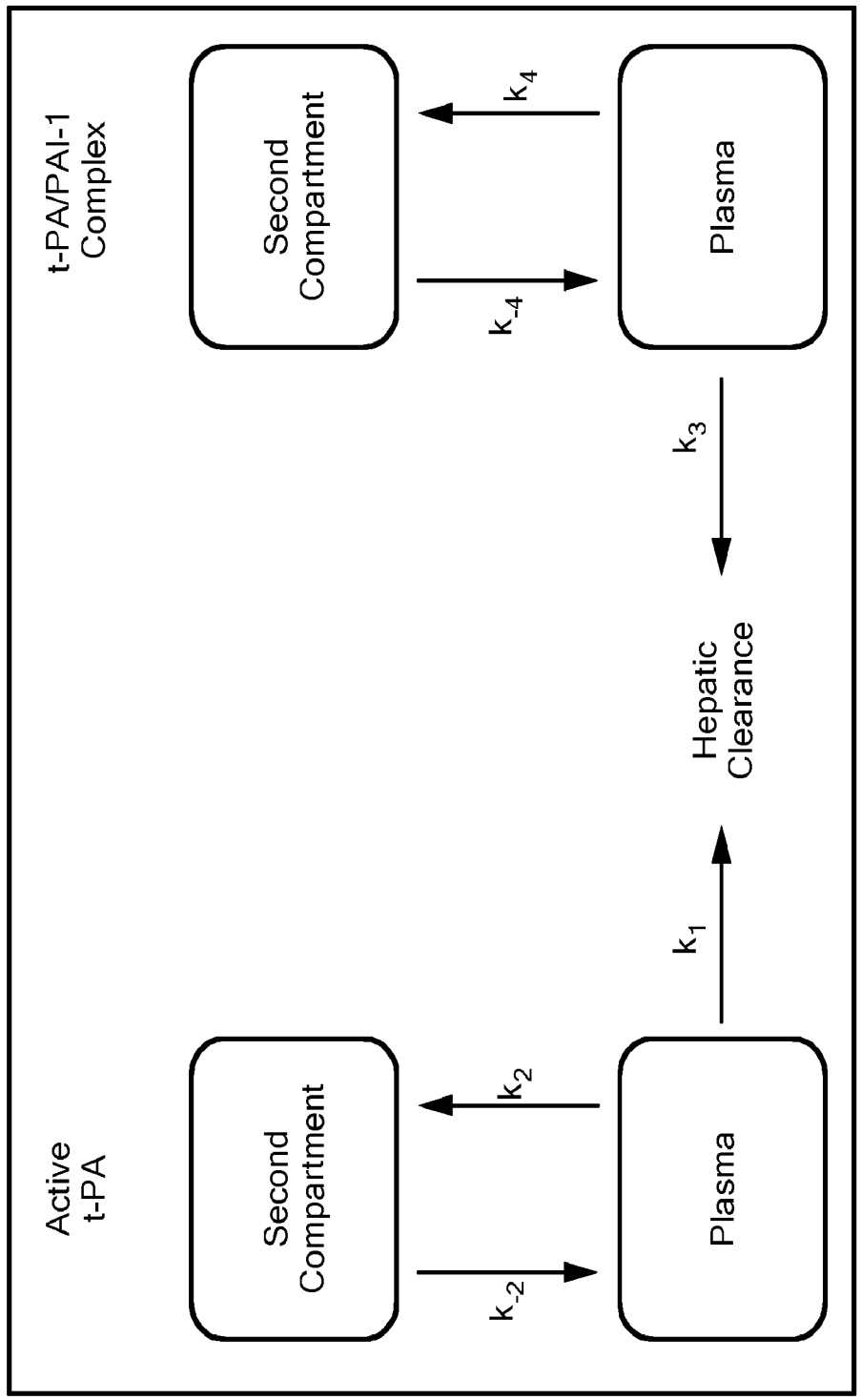
FIG. 19 is a schematic diagram showing how tPA and PM-1 are mutually inhibitory and exist in equilibrium with a covalent complex that is inactive and cleared by the liver.
Figure 20:
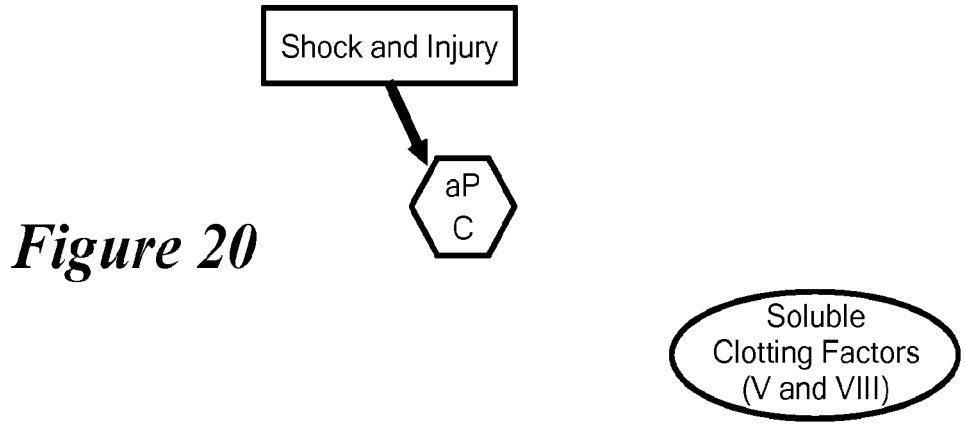
FIGS. 20-25 are a series of schematic diagrams showing that activated protein C (aPC) is a driver of trauma induced coagulopathy (TIC) via degradation of Factors V and VIII.
Figure 21:
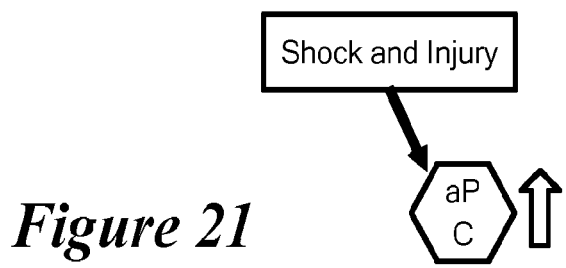
Figure 22:
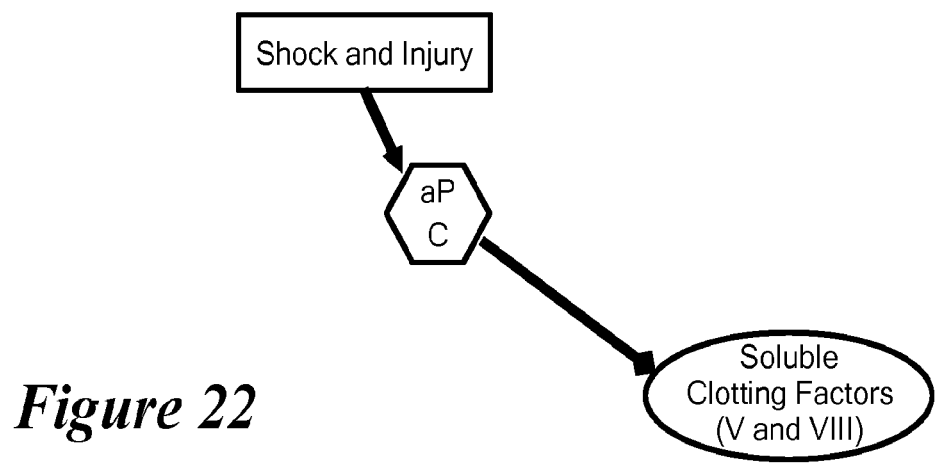
Figure 23:
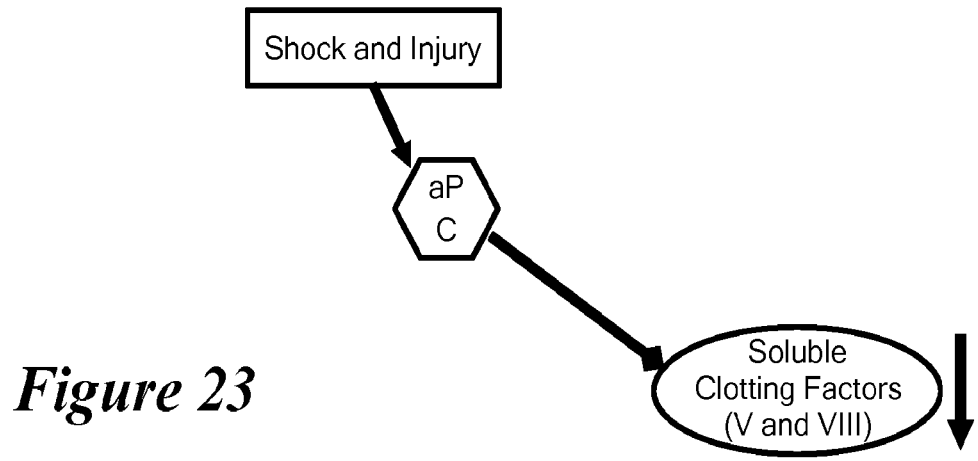

As schematically depicted in FIG. 16, tissue plasminogen activator (tPA) catalyzes the conversion of the zymogen plasminogen to its active, fibrinolytic form plasmin. Plasminogen activator inhibitor-1 (PAI-1) is the cognate inhibitor of tPA, with which it forms a mutually inhibitory covalent complex (FIG. 17). This shuts down the plasmin system (FIG. 18). tPA and PAI-1 are mutually inhibitory, existing in equilibrium with a covalent complex that is inactive and cleared by the liver (see FIG. 19). Preliminary work has shown undetectably low levels of PAI-1 activity in the subset of trauma patients with demonstrable hyperfibrinolysis on TEG. However, while total PM-1 is increased in ischemic conditions such as myocardial infarction (MI), stroke and vascular disease, this is largely in the form of the inactive covalent complex with PM-1. Moreover, the microvascular endothelium is capable of releasing tPA in response to ischemic stress as well as catecholamines and vasopressin which are markedly elevated in hemorrhagic shock.

Figure 24:
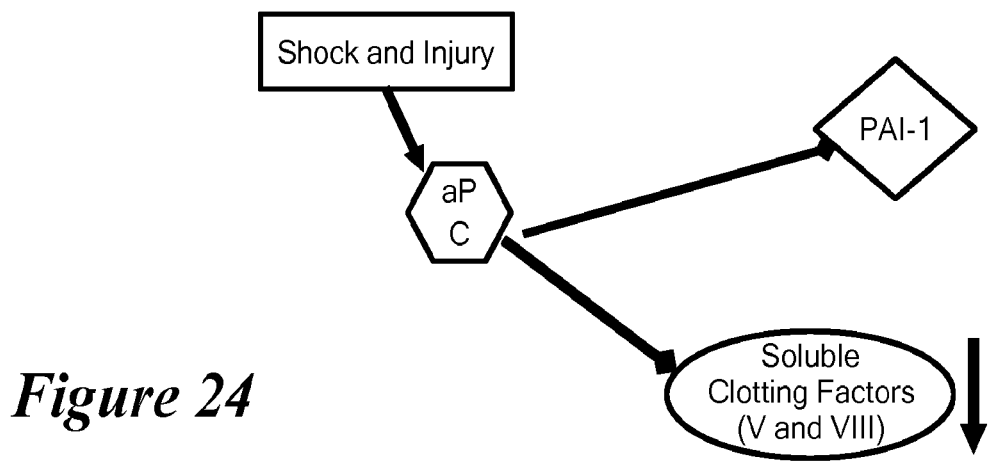
Figure 25:
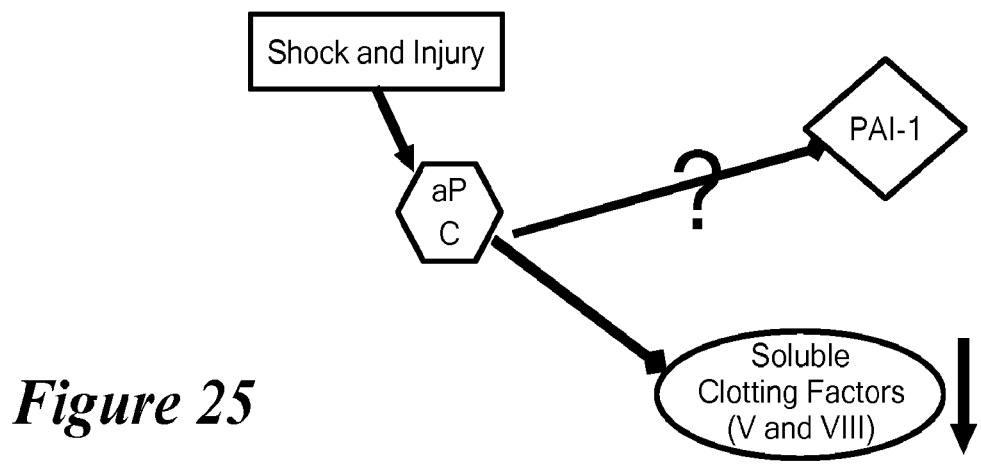

As depicted in FIGS. 20-25, it has been shown that activated protein C (aPC) is a driver of TIC via degradation of factors V and VIII (FIGS. 20-23); furthermore it has been suggested that aPC mediated degradation of PAI-1 is the chief cause of systemic hyperfibrinolysis in trauma (FIGS. 24-25).

Figure 26:
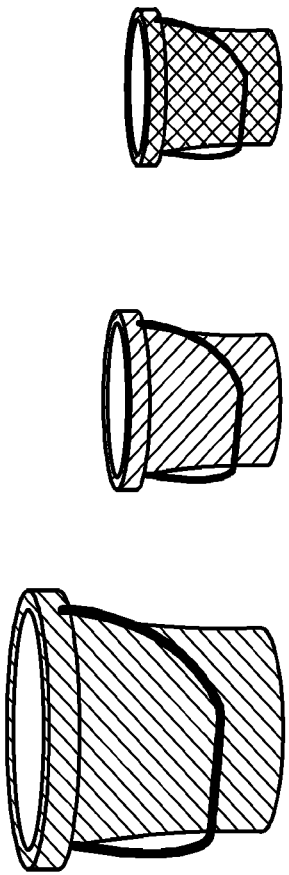
FIG. 26 is a chart showing the three principal components of trauma induced coagulopathy (TIC).

However, principal component analyses have demonstrated that the hyperfibrinolytic component of TIC (seen as the LY30 parameter of the thromboelastogram, which makes up Principal Component 3 in FIG. 26) is distinct and independent from the thrombin generation component of TIC. Therefore these two phenomena, must be mechanistically distinct, and cannot both be mediated by aPC.

Therefore, post-injury hyperfibrinolysis may be due to the excessive production of tPA and not the destruction of PAI-1.

To test this, 86 consecutive severely injured trauma patients (median injury severity score (ISS) of 25, median base excess: −7.5) were screened for hyperfibrinolysis and compared to healthy controls (e.g., healthy volunteers). Using activity ELISAs and immunoassays, the relative levels of active PAI-1, active tPA and the inactive covalent tPA/PAI-1 complex in these patient's plasma (and that of healthy controls) was quantitated.

Figure 27:
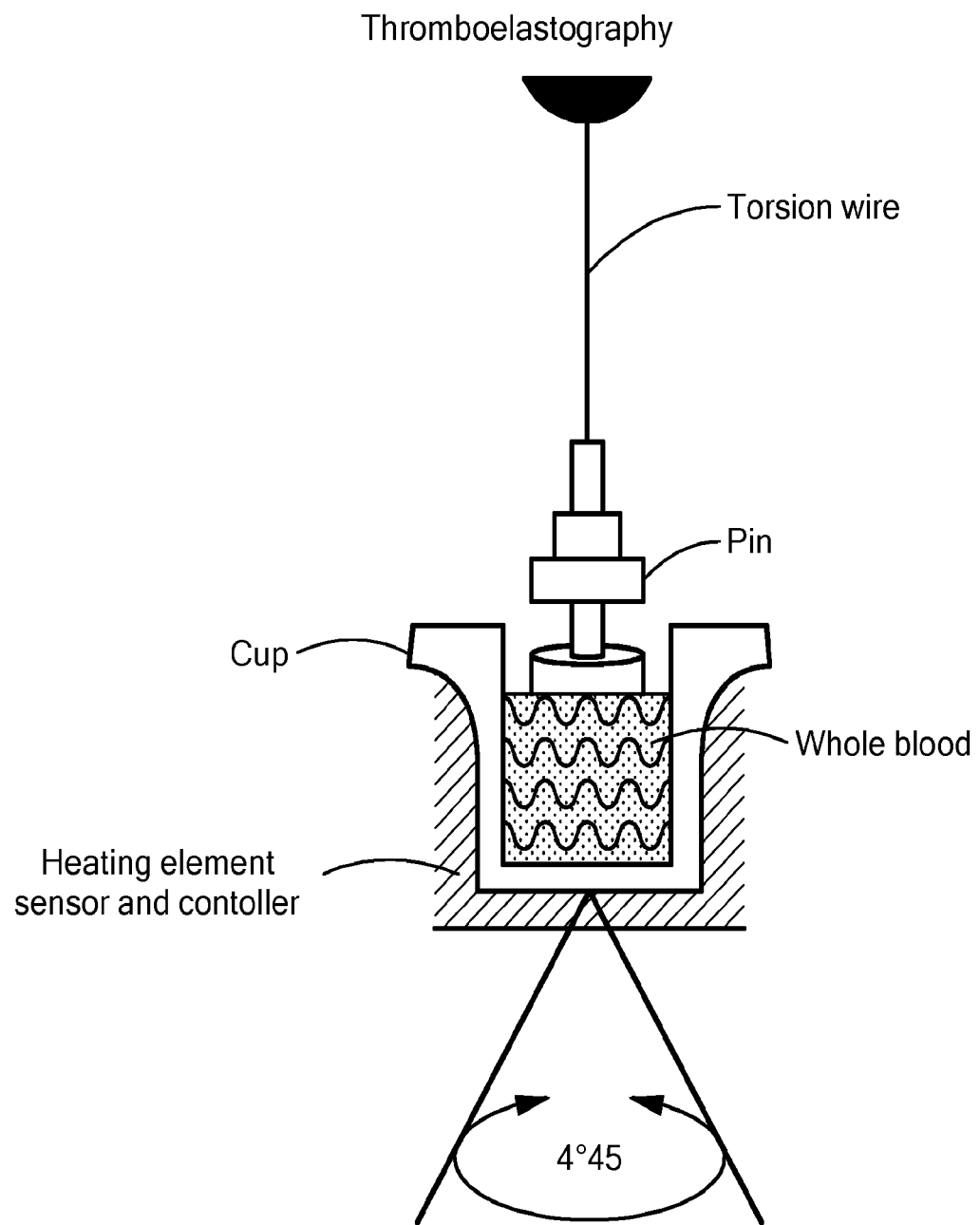
FIG. 27 is a diagram showing the mechanistic action of the thromboelastography (TEG) assay.

The viscoelastic hemostatic assay Thromboelastography or "TEG" measures the mechanical strength of the evolving blood clot to measure fibrinolysis (See FIG. 27)

Figure 28:
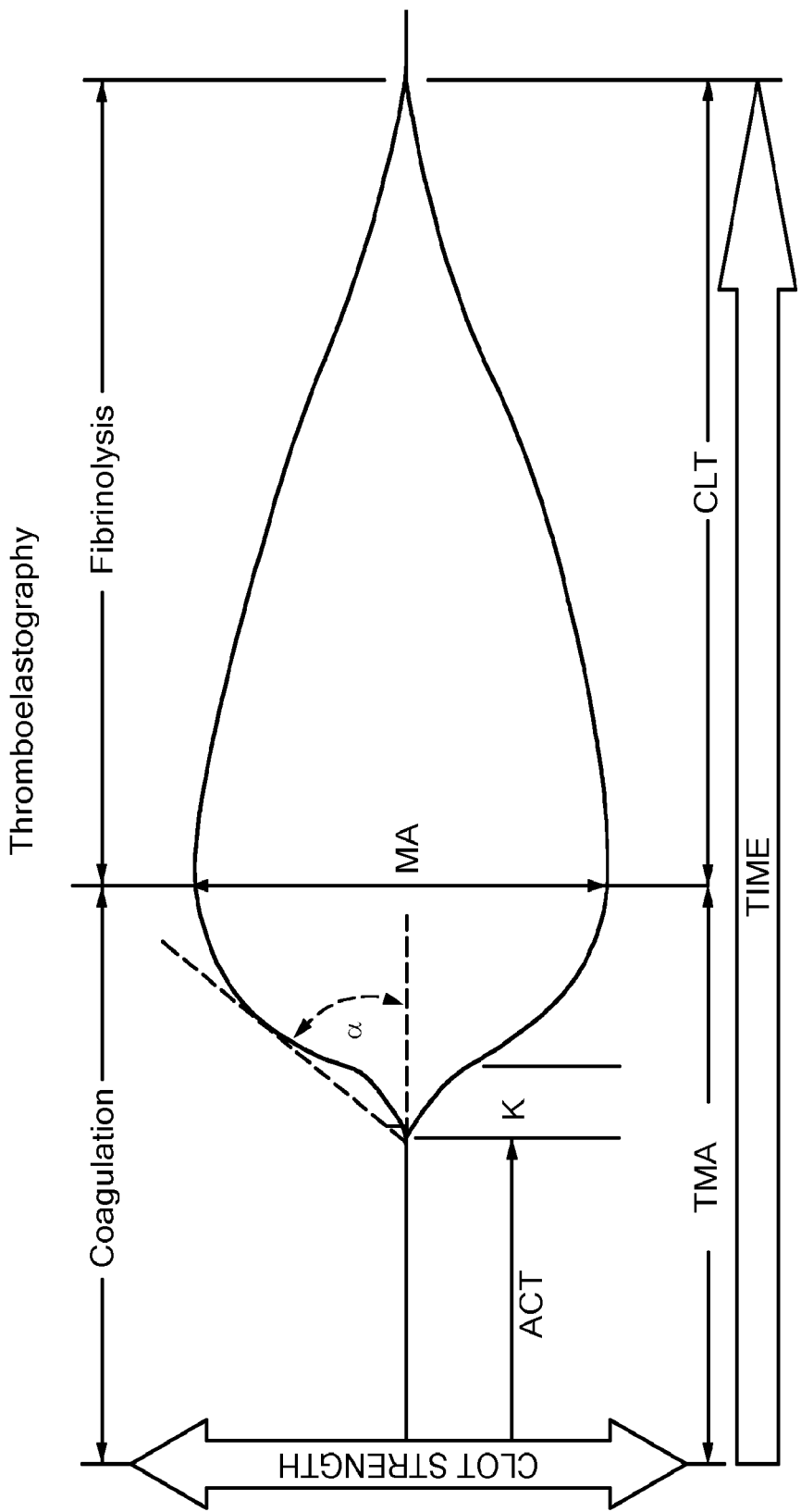
FIG. 28 is a classic TEG curve.
Figure 29:
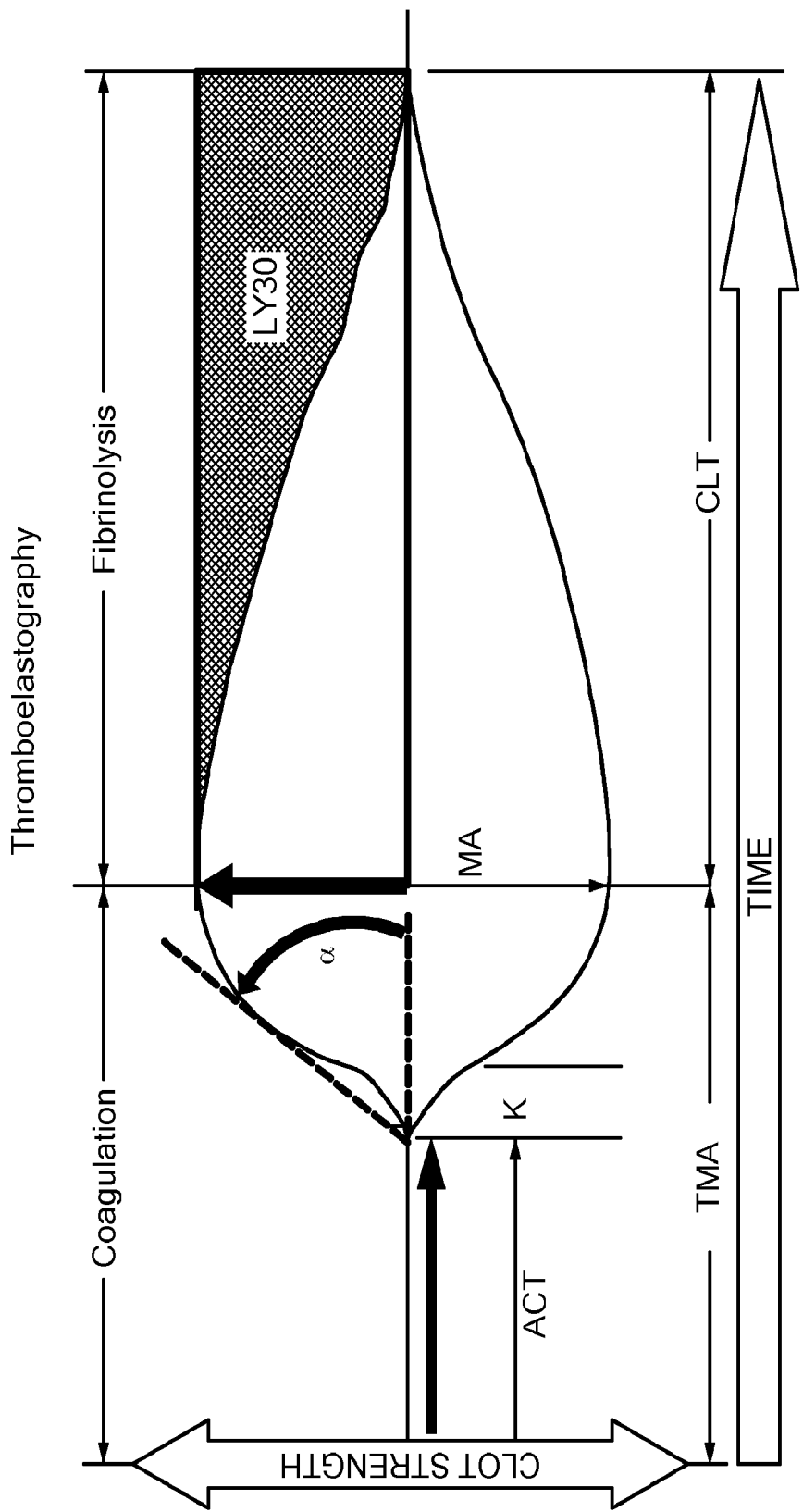
FIG. 29 is the classic TEG curve of FIG. 28 with the alpha angle and LY30 metrics shown.

As the strength of the clot increases over time, the classic TEG curve develops with time on the X-axis and clot strength on the Y-axis. (See FIGS. 4 and 28). The amount of clot lysis in the 30 minutes following MA, or LY30, quantifies fibrinolysis, as the loss of potential area under the TEG curve (see FIG. 29).

Figure 30:
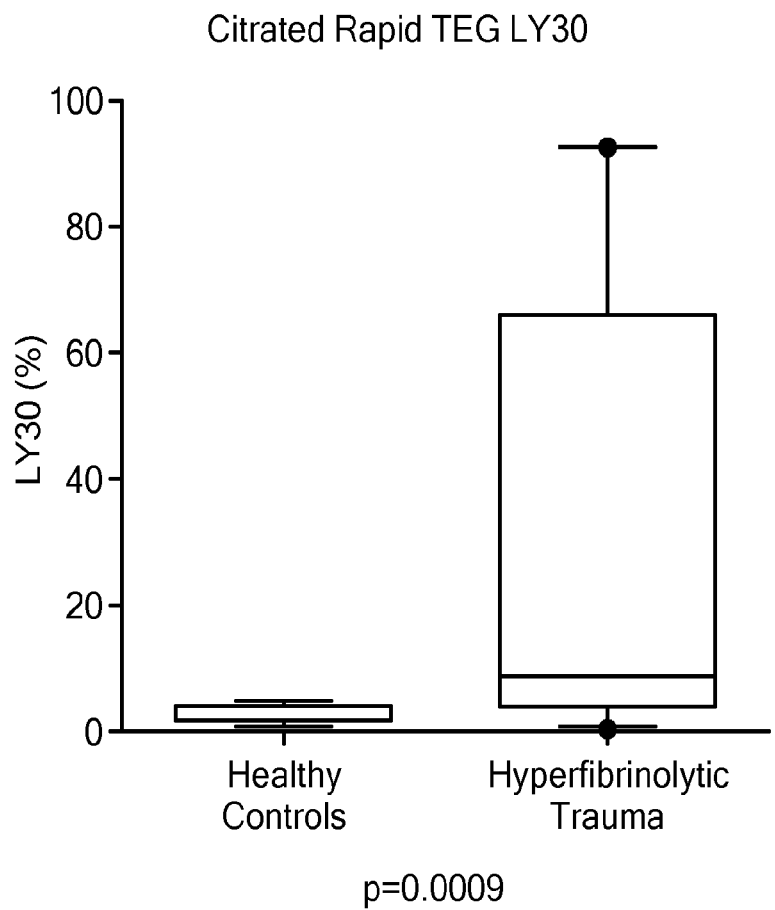
FIG. 30 is a graph showing the LY30 values of hyperfibrinolytic patients as compared to healthy volunteers.

As anticipated, the hyperfibrinolytic patients not only displayed severe clot lysis on their TEG (see FIG. 30), but were also far sicker in general, with a median ISS of 33, a base deficit of 9, and a 52% mortality rate.

Figure 31:
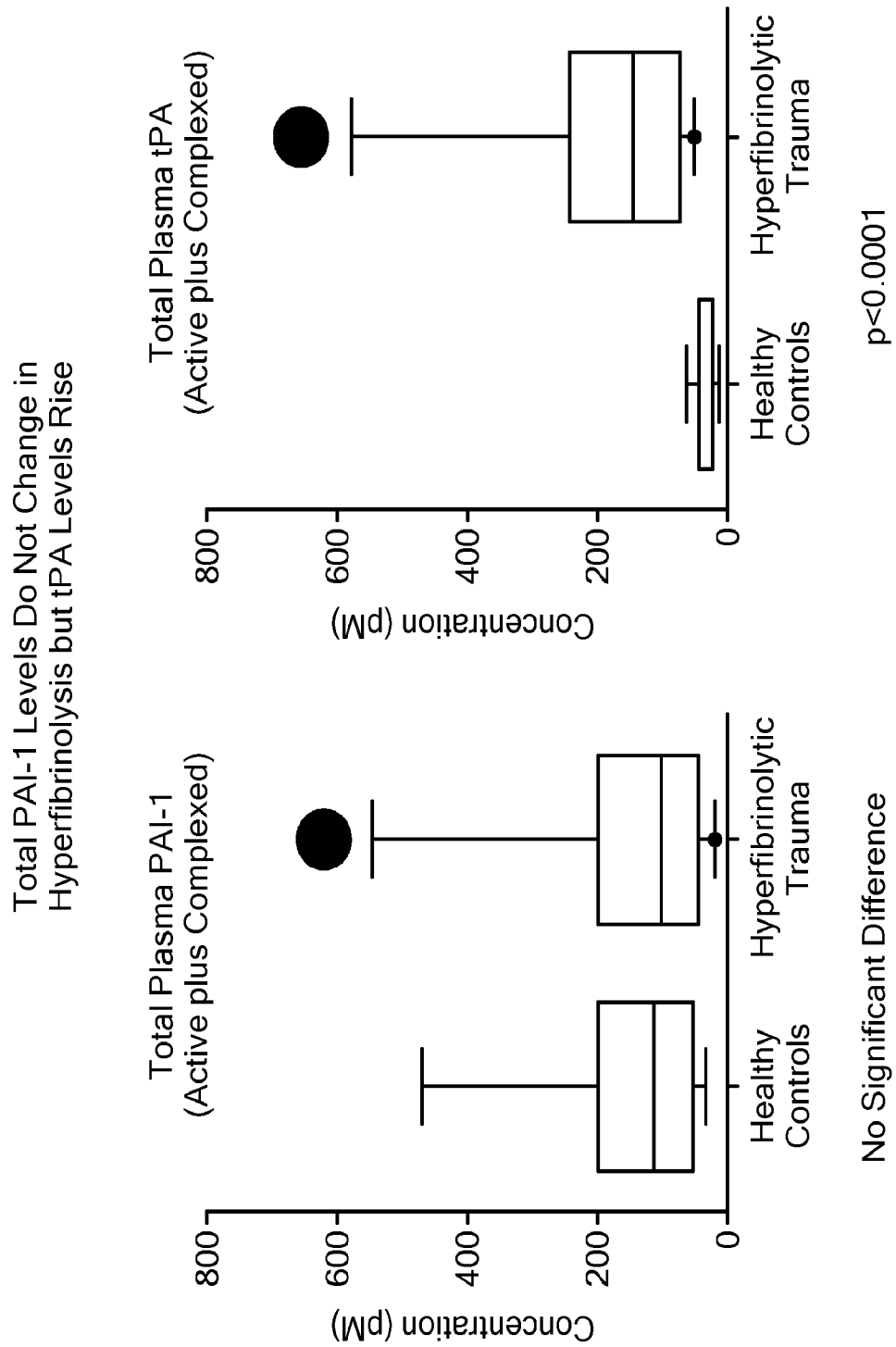
FIG. 31 is a graph showing the concentrations of total plasma PAI-1 (active plus complexed; left panel) and total plasma tPA (active plus complexed; right panel) in healthy volunteers and patients with hyperfibrinolysis.
Figure 32:
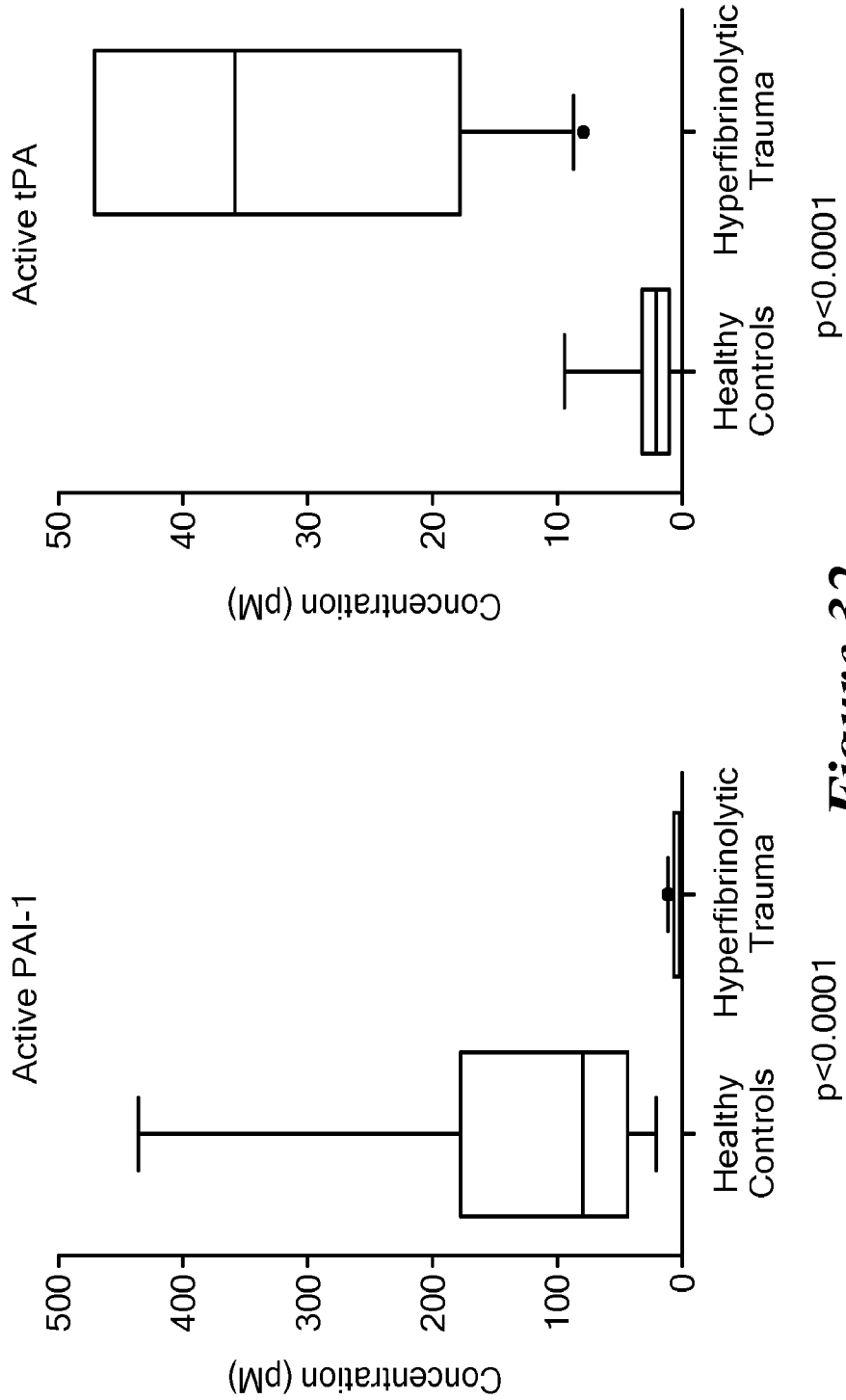
FIG. 32 is a graph showing the concentrations of active PM-1 (left panel) and active tPA (right panel) in healthy volunteers and patients with hyperfibrinolysis.

Total PM-1 levels (the sum of active PM-1 and its complex with tPA) were measured. The levels are identical in hyperfibrinolytic patients and healthy controls (see FIG. 31, left panel), while total plasma tPA rose dramatically—nearly 2 orders of magnitude (see FIG. 31, right panel). This reflects a marked shift to the complexed form of PM-1 with tPA in hyperfibrinolytic patients. In parallel to this shift, active tPA rose almost 10 fold from its minimal levels in healthy controls, reflecting the overflow of tPA as the reserves of PAI-1 are overwhelmed. (See FIG. 32, right panel).

Figure 33:
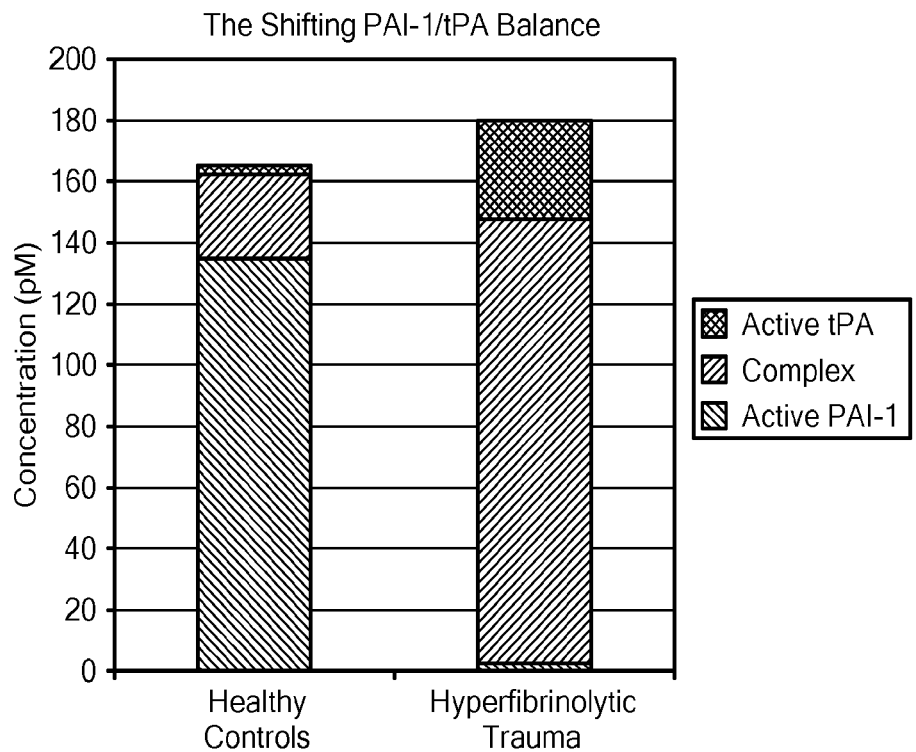
FIG. 33 is a bar graph showing the shifting PM-1/tPA balance in healthy volunteers (left) versus patients with hyperfibrinolysis (right).

To put this in perspective, FIG. 33 is a graphical representation of the global shift between the three species in question: the active form of tPA (top of bars in red), the active form of PAI-1 (bottom of bars in blue) and the inert complex (middle of bars in purple. A healthy person has a vast reserve of active PAI-1, a small amount of complex and almost no active tPA (see FIG. 33, left bar). In hyperfibrinolysis in trauma, the total tPA levels rise markedly, driving the free tPA into complex (see FIG. 33, right bar). Note that the amount of active PAI-1 as blue bars in the hyperfibrinolytic trauma patients in the right bar of FIG. 33 is very low.

Thus, hyperfibrinolysis in trauma with hemorrhagic shock is driven by a massive increase in tPA levels, not destruction of PAI-1. Large excesses of tPA inactivate PM-1 by driving formation of the covalent PAI-1/tPA complex, which is subsequently cleared.

Figure 34:
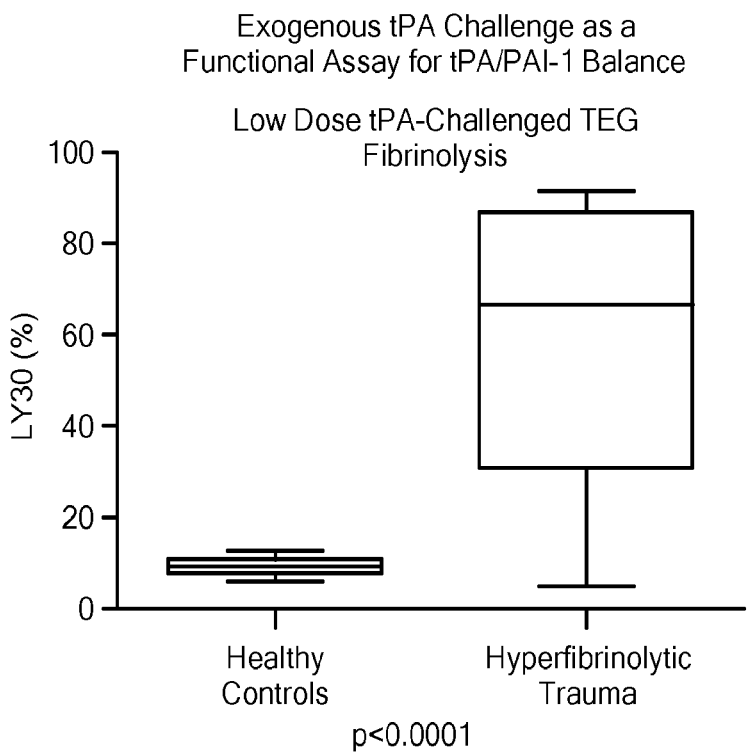
FIG. 34 is a graph showing the LY30 value results of a low dose tPA TEG assay in healthy controls (left) and patients with hyperfibrinolysis (right). As can be seen, the LY30 value increases in patients with hyperfibrinolysis in the viscoelastic assay in the presence of low dose tPA.

To apply this clinically, the assay described herein was developed. In some embodiments, the novel TEG assay described herein was developed, wherein the patient's blood is incubated with a small concentration of tPA prior to running the TEG. This exogenous challenge with tPA unmasks this condition of tPA excess and relative PM-1 deficiency. This assay gives a clearer signal for the state of the plasmin system than traditional TEG, much faster than immunoassays, and also revealing those patients with latent hyperfibrinolysis who may be just on the threshold of decompensation. As shown in FIG. 34, patients with hyperfibrinolysis have significantly higher fibrinolysis (as measured by LY30) as compared to normal healthy volunteers when their blood is incubated with 75 ng/ml tPA prior to taking the TEG measurement.

In conclusion, enzymatic degradation of active PAI-1 is not a significant feature of trauma-induced hyperfibrinolysis, but rather the population of PM-1 shifts from its free, active form to the inactive complex with tPA. tPA-challenged TEG is a simple functional assay for the evolution of tPA excess, early in the course of traumatic injury.

Example 9: Fibrinolysis Shutdown

Figure 35:
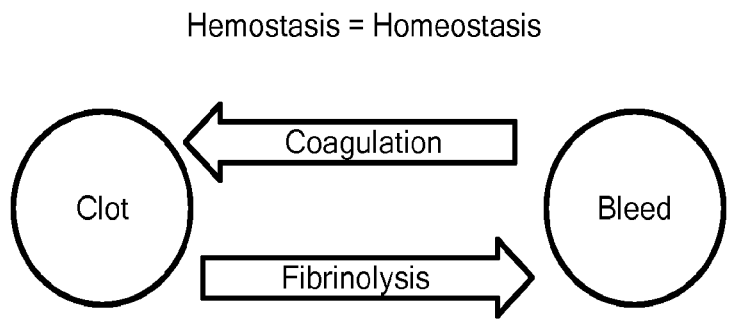
FIGS. 35-37 are a series of schematic diagrams showing the interrelated and counterbalancing systems of coagulation and fibrinolysis in hemostasis.
Figure 36:
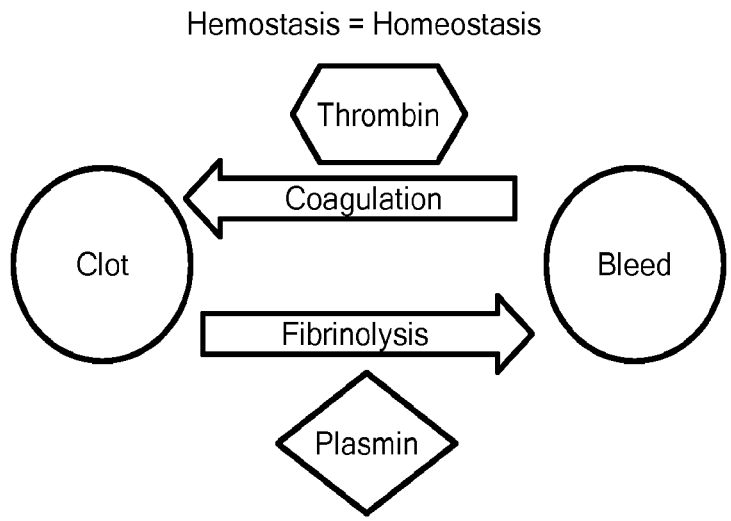
Figure 37:
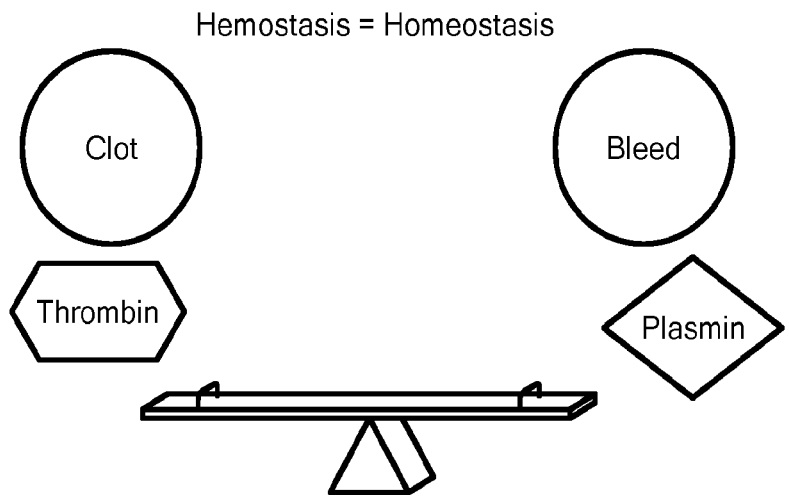

Derangements of hemostasis are common in trauma—but hemostasis (of course) is more than just clotting. Hemostasis is the maintenance of blood flowing where it is supposed to and prevention of its flowing where it should not—of hemorrhage—blood's escape from the vascular compartment. This homeostasis between bleeding and clotting is maintained by two interrelated and counterbalancing systems: that of coagulation and fibrinolysis (see FIG. 35). This balance is driven primarily by the respective activities of thrombin and plasmin (FIG. 36), which catalyze the building and dissolution of the fibrin matrix of the clot and maintain the balance of hemostasis (FIG. 37).

Figure 39:
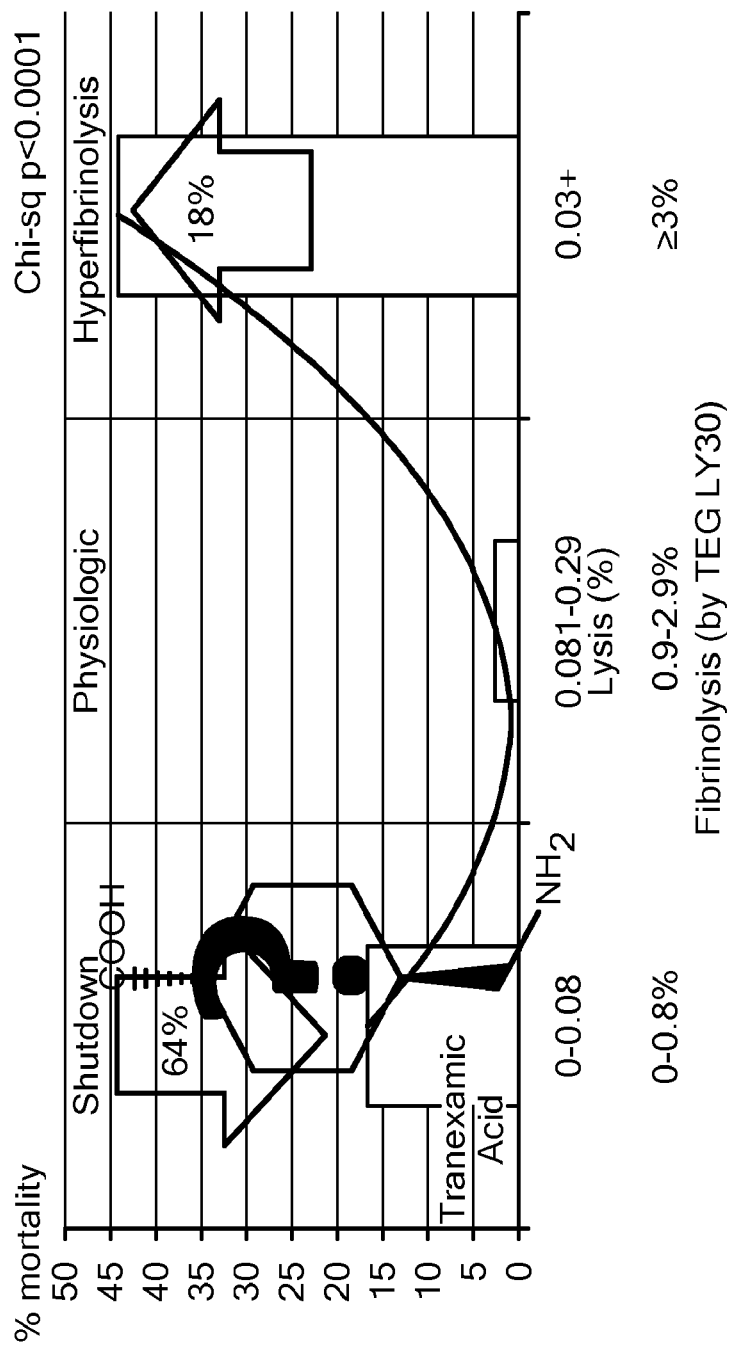
FIG. 39 is the graph of FIG. 38 showing the questionable use of antifibrinolytics (e.g., TXA) in fibrinolysis shutdown patients.

The fibrinolytic system is frequently deranged in trauma. While the lethal phenomenon of hyperfibrinolysis in the setting of trauma induced coagulopathy (TIC) occurs as discussed above in Example 8, this pathology comprises only a small subset of the spectrum of fibrinolytic activity observed in trauma. There are three distinct phenotypes of fibrinolysis, with hyperfibrinolysis at one end of the spectrum with an incidence of less than 20% and the most common state "Fibrinolysis Shutdown" (comprising >60% of severely injured trauma admissions) at the other end of the spectrum (see FIGS. 3 and 38). Mortality is elevated at these two extremes of fibrinolytic activity, compared to patients with physiologic levels of fibrinolysis, yielding the "U-shaped" mortality distribution (see FIG. 38). In the case of fibrinolysis shutdown, the mortality is predominately due to late causes such as multiple organ failure, not from hemorrhage—seriously calling into question whether these sorts of patients would be helped or harmed by the empiric use of antifibrinolytics such as TXA (see FIG. 39).

Fibrinolysis is part of a tightly regulated homeostatic system, whose chief end effector is plasmin. tPA catalyzes the conversion of the zymogen plasminogen to plasmin, its active, fibrinolytic form (See FIGS. 16 and 17). PAI-1 is the cognate inhibitor of tPA, with which it forms a mutually inhibitory covalent complex, shutting down the plasmin system (see FIG. 18).

tPA predominates in hyperfibrinolysis. Elevated tPA activity (FIG. 32, right panel) driving a suppression of PAI-1 activity (FIG. 32, left panel) is the predominant feature of hyperfibrinolysis in trauma. The reversal of this situation is obtained in the setting of fibrinolysis shutdown (e.g., elevated PM-1, driving the suppression of tPA activity). Thus, fibrinolysis shutdown in traumatic injury may be principally due to elevated PM-1.

To test this, field blood and plasma samples from 47 consecutive trauma-activations who were in fibrinolysis shutdown were collected. For the purposes of this study, fibrinolysis shutdown was defined conservatively as <0.8% TXA-reversible fibrinolysis on their admission thromboelastogram. The 47 consecutive highest-level trauma activation patients with fibrinolysis shutdown were screened by TEG (the patients has a median ISS 17, median BD 7). They were compared to 14 healthy volunteers with normal fibrinolysis by two assays: A TEG challenged with exogenous tPA—to test the degree of functional resistance to activation of the patient's plasmin system, and a triple ELISA for active PM-1, active tPA and the inactive complex of the PM-1/tPA.

Figure 40:
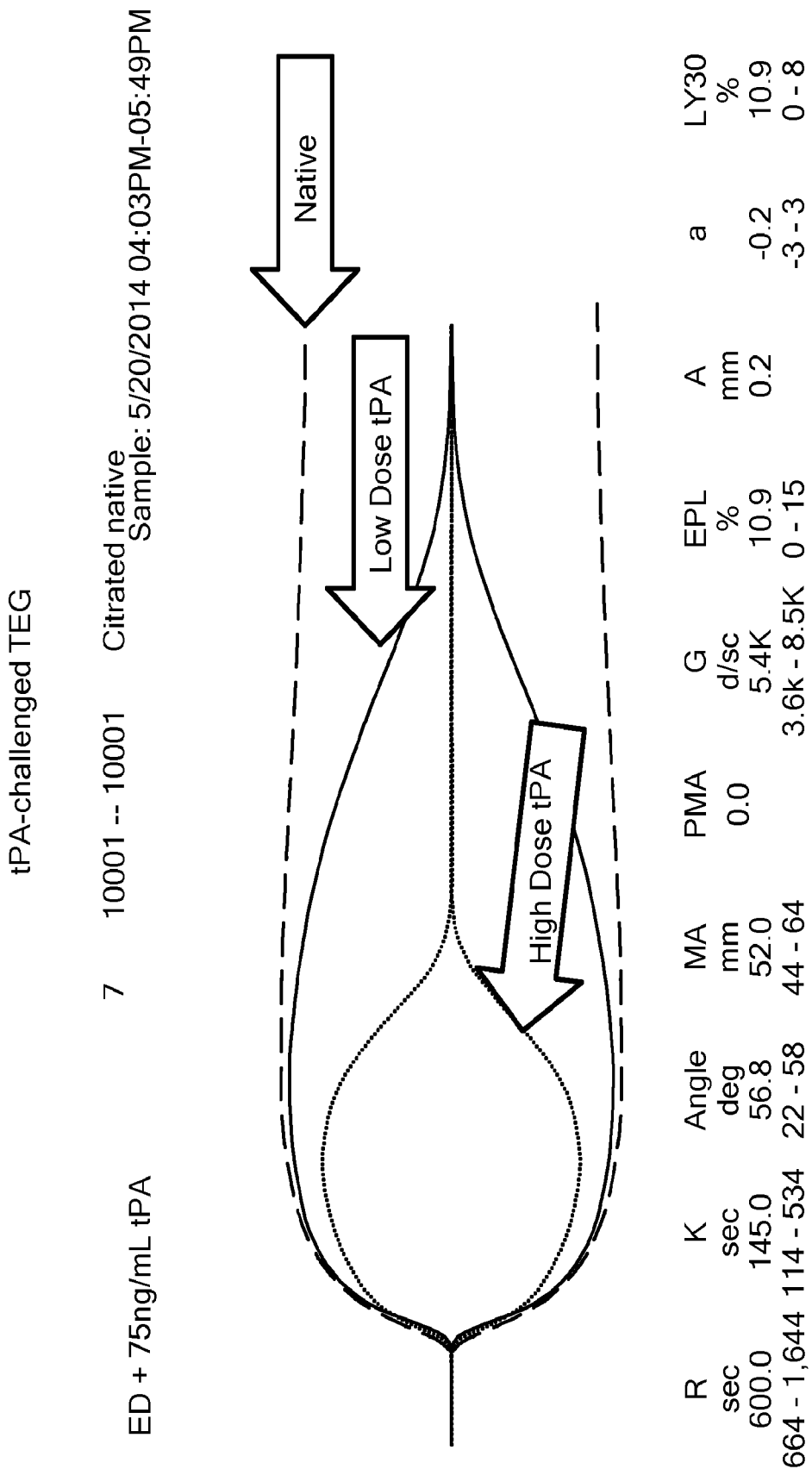
FIG. 40 is the image of the TEG tracing from healthy volunteer patient 33 of FIG. 9B overlaid with labels showing untreated blood (line labeled "Native" in FIG. 40), blood treated with low dose tPA (line labeled "Low Dose tPA" in FIG. 40) or blood treated with high dose tPA (line labeled "High Dose tPA" in FIG. 40).

FIGS. 9B and 40 show the TEG curve of a blood sample from a healthy volunteer patient 33 using the tPA challenged TEG assay described herein and that was used in this study. The assay (sometimes referred to as tPA challenged TEG) is a standard TEG run with whole blood in the presence of various concentrations of exogenous tPA. FIGS. 9B and 40 show the TEG tracings of a healthy control subject whose blood is untreated when the TEG assay is run (the "Native" TEG tracing), whose blood is run in the TEG assay in the presence of a low dose of 75 ng/mL of tPA (the "low dose tPA"), and whose blood is run in the TEG assay in the presence of a high dose of 150 ng/mL of tPA (the "high dose tPA). As expected, fibrinolysis as measured by LY30 increases with the tPA-challenge dose in a healthy individual.

Figure 41:
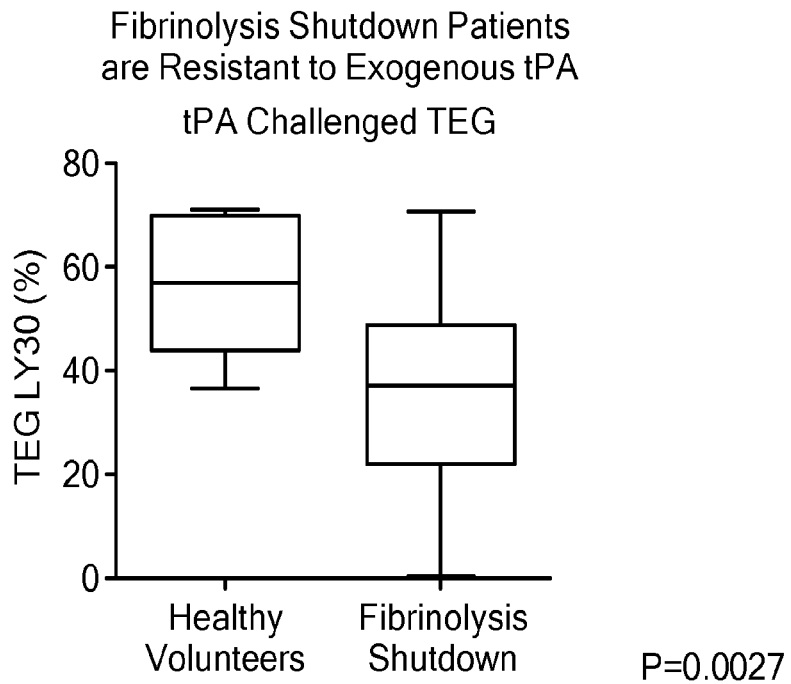
FIG. 41 is a graph showing the LY30 value results of a high dose tPA TEG assay in healthy controls and patients with fibrinolysis shutdown. As can be seen, the LY30 value decreases in patients with fibrinolysis shutdown in the viscoelastic assay in the presence of high dose tPA.

However, fibrinolysis shutdown patients are resistant to exogenous tPA. As shown in FIG. 41, Trauma patients without detectable fibrinolysis on their admission TEG displayed resistance to exogenous tPA on tPA-challenged TEG. FIG. 41 shows the response of these patients' blood to a high dose of tPA (150 ng/mL). As FIG. 41 shows, patients in fibrinolysis shutdown have a median tPA-challenged LY30 20% lower than healthy controls.

Figure 42:
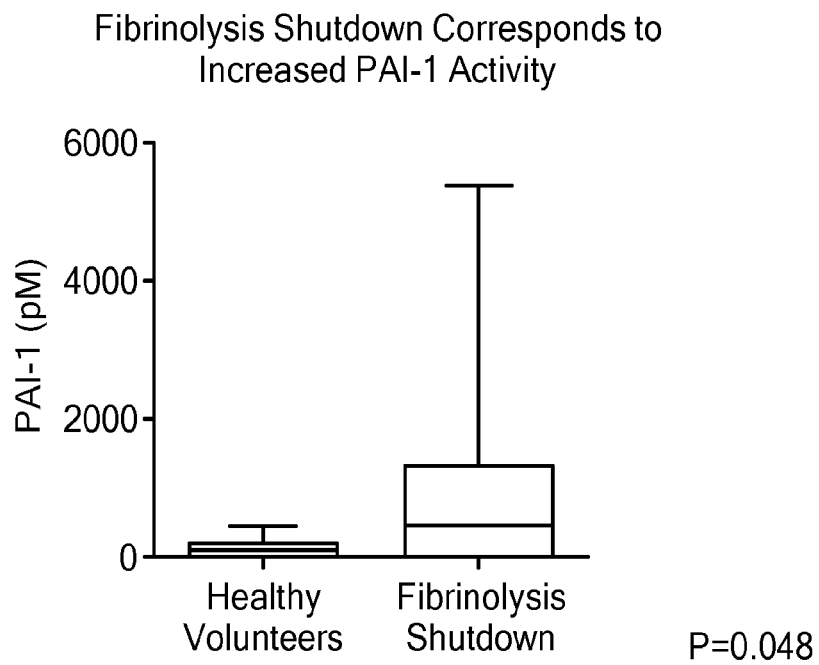
FIG. 42 is a graph showing the active PM-1 activity of healthy controls and patients with fibrinolysis shutdown.

Not surprisingly, active PM-1 is nearly 6-fold higher in trauma patients with fibrinolysis shutdown than healthy volunteers, with some patients reaching levels nearly 100× normal (see FIG. 42).

Figure 43:
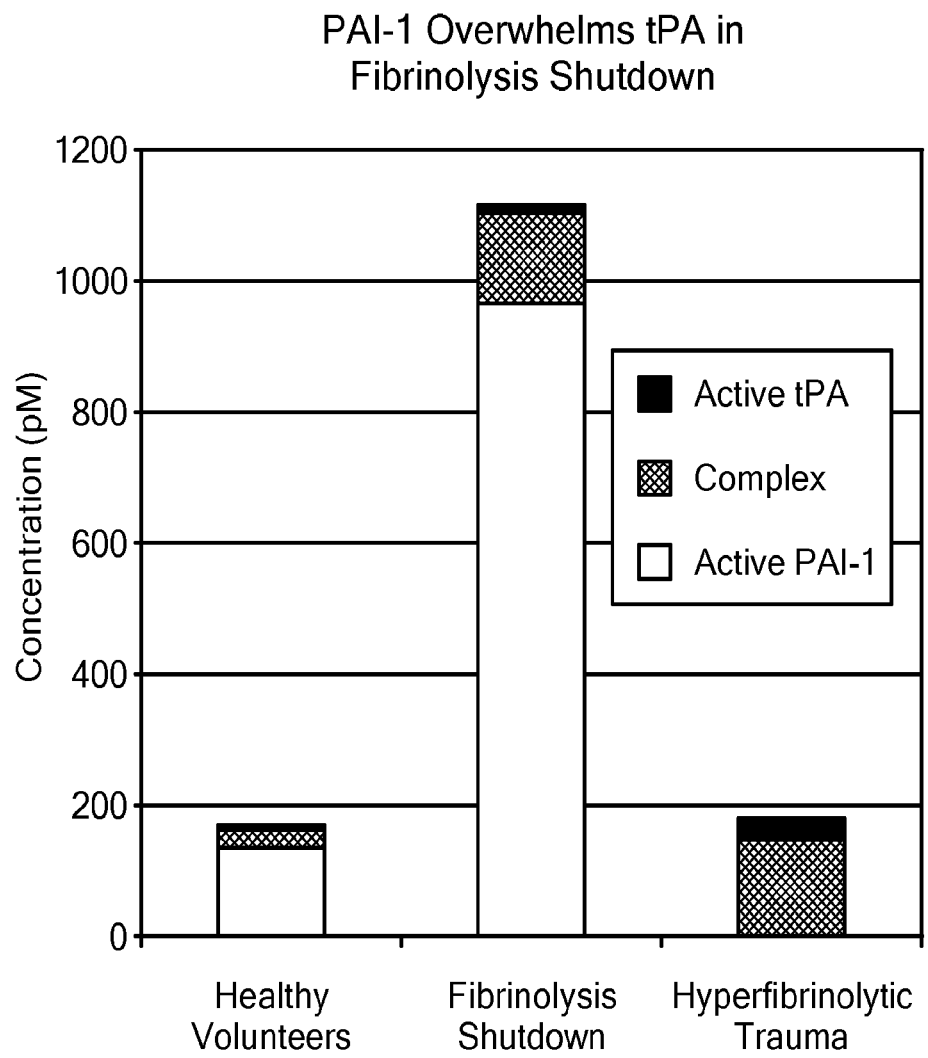
FIG. 43 is a bar graph showing the relative levels of active PM-1 (blue), active tPA (red) and mutually inactivated tPA/PAI-1 complex (purple) in healthy volunteers, patients with fibrinolysis shutdown, and patients with hyperfibrinolysis.

To put these data into global context, FIG. 43 shows a graphical representation of the relative levels of active PAI-1 (in blue at the bottom of the bars in FIG. 43) active tPA (in red at the top of the bars in FIG. 43) and the mutually inactivated complex (in purple in the middle of the bars in FIG. 43) across three distinct populations: Healthy volunteers on the left, trauma patients with fibrinolysis shutdown in the middle displaying massively elevated PAI-1, and hyperfibrinolytic trauma patients on the right. Interestingly, trauma patients with fibrinolysis shutdown display elevated total tPA (the sum of the red and purple portions of the bar) but this is almost all driven to the inactive complex by overwhelming PM-1 (blue at the bottom of the bars in FIG. 43). In contrast, on the right of FIG. 43, there is the inverse relationship for trauma patients with hyperfibrinolysis, which have elevated tPA levels driving PM-1 into the inactive complex. (See also FIG. 2)

In summary, trauma patients with fibrinolysis shutdown on their admission TEG—which comprise >60% of severely injured patients—showed increased resistance to exogenous tPA and a 6-fold increase in active PM-1, compared to healthy controls, while active tPA was suppressed to near zero in these patients with fibrinolysis shutdown.

Figure 44:
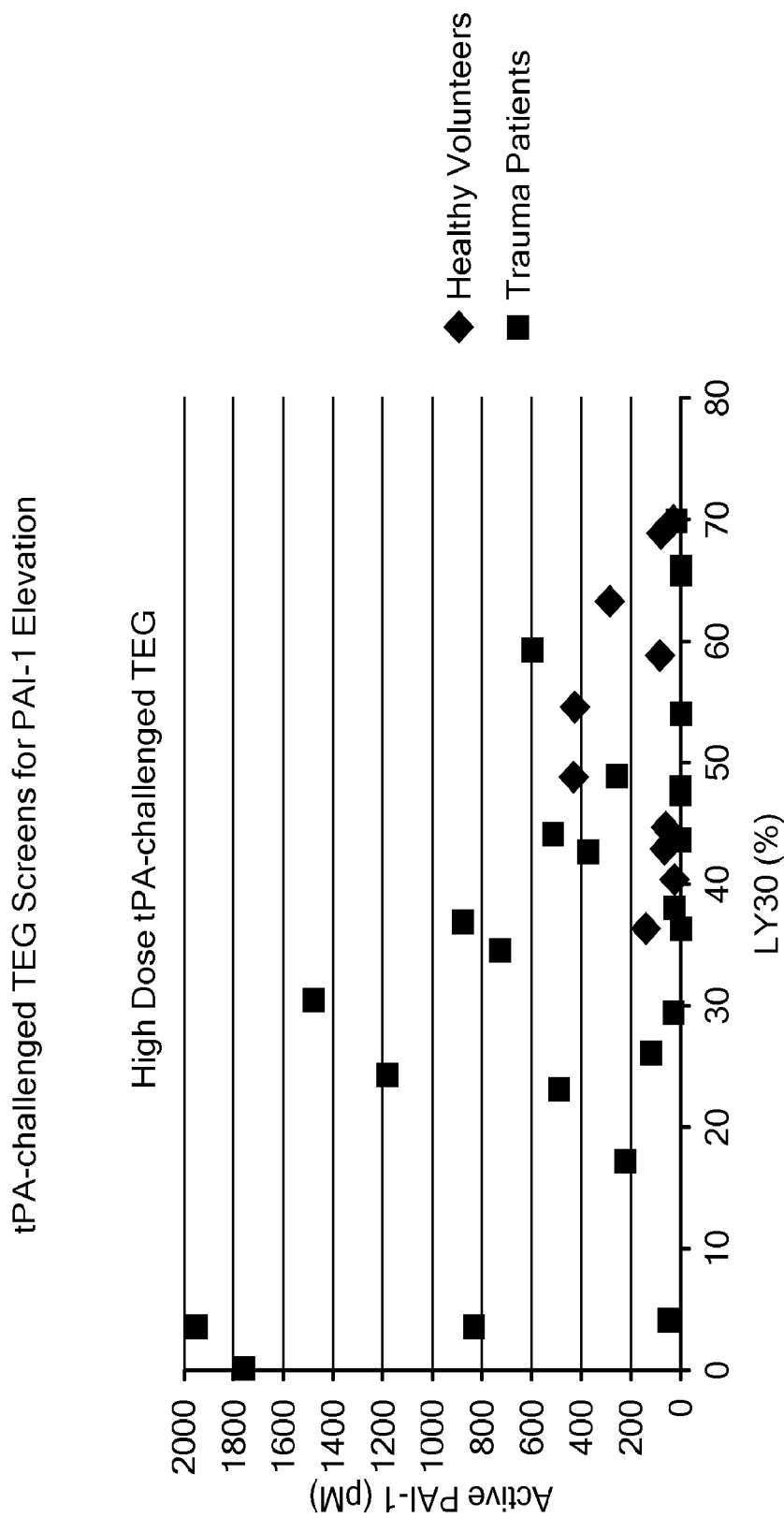
FIG. 44 is a scatter plot plotting active PM-1 levels as a function of LY30 values at the high dose tPA in healthy volunteers (green diamonds) and trauma patients (purple squares).

From a standpoint of clinical applicability, the tPA-challenged TEG as a functional assay may be applied to discriminate trauma patients with abnormally elevated PM-1 and a completely non-functional plasmin system from those who merely have no overt evidence of fibrinolysis on their TEG. FIG. 44 is a simple scatter plot of active PM-1 levels as a function of high-dose tPA-challenged TEG response in both health volunteers (in green diamonds) and trauma patients (in purple squares). As shown in FIG. 44, all trauma patients with abnormally elevated PM-1 displayed suppression of their response to exogenous tPA challenge, meaning that the assay has excellent negative predictive value. Thus, this assay is a good functional screening tool for severe fibrinolysis shutdown.

Thus, most severely injured patients are resistant to tPA due to massive elevation of their PM-1 levels—and therefore potentially at risk for adverse events if given antifibrinolytics. The tPA-challenged TEG assay described herein offers a means to rapidly screen for and diagnose fibrinolysis shutdown in these trauma patients and thus avoid unnecessary and possibly harmful antifibrinolytic therapy.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for detecting latent hyperfibrinolysis or fibrinolysis shutdown in a patient, the method comprising
   a) subjecting a first whole blood sample from the patient to a viscoelastic assay in the presence of a low amount of between about 1 ng/ml to about 100 ng/ml of a thrombolytic agent to obtain a low coagulation characteristic value of the patient, wherein the viscoelastic assay measures mechanical strength of a blood clot in the first whole blood sample over time, wherein the viscoelastic assay is selected from the group consisting of a thromboelastographic (TEG) assay and a thromboelastometry (TEM) assay, wherein the low coagulation characteristic value is selected from the group consisting of an LY30 value or a derivative thereof and an LI30 value or a derivative thereof, and wherein the thrombolytic agent is human single chain tissue plasminogen activator (tPA), human double chain tPA, tPA from a non-human mammalian species, alteplase, reteplase, tenecteplase, anistreplase, serokinase, streptokinase, urokinase, or kallikrein;
   b) subjecting a second whole blood sample from the patient to a viscoelastic assay in the presence of a high amount of between about 110 ng/ml to about 1200 ng/ml of the thrombolytic agent to obtain a high coagulation characteristic value of the patient, wherein the viscoelastic assay measures mechanical strength of a blood clot in the first whole blood sample over time, wherein the viscoelastic assay is selected from the group consisting of a TEG assay and a TEM assay, wherein the high coagulation characteristic value is selected from the group consisting of an LY30 value or a derivative thereof and an LI30 value or a derivative thereof;
   c) comparing the low coagulation characteristic value of the patient to a low coagulation characteristic value of a healthy individual or an averaged low coagulation characteristic value of a group of healthy individuals, the low coagulation characteristic value of the healthy individual obtained by subjecting a blood sample from a healthy individual to the viscoelastic assay in the presence of the low amount of the thrombolytic agent and the averaged low coagulation characteristic value of the group of healthy individuals obtained by subjecting blood samples from healthy individuals to the viscoelastic assay in the presence of the low amount of the thrombolytic agent, and
   d) comparing the high coagulation characteristic value of the patient to a high coagulation characteristic value of a healthy individual or an averaged high coagulation characteristic value of a group of healthy individuals, the high coagulation characteristic value of the healthy individual obtained by subjecting a blood sample from a healthy individual to the viscoelastic assay in the presence of the high amount of the thrombolytic agent and the averaged high coagulation characteristic value of the group of healthy individuals obtained by subjecting blood samples from healthy individuals to the viscoelastic assay in the presence of the high amount of the thrombolytic agent, and
   wherein an increase in the low coagulation characteristic value of the patient as compared to the low coagulation characteristic value of the healthy individual or to the averaged low coagulation characteristic value of the group of healthy individuals identifies the patent as having latent hyperfibrinolysis and wherein a decrease in the high coagulation characteristic value of the patient as compared to the high coagulation characteristic value of the healthy individual or to the averaged high coagulation characteristic value of the group of healthy individuals identifies the patent as having fibrinolysis shutdown.

2. The method of claim 1, wherein the thrombolytic agent is human single chain tissue plasminogen activator (tPA).

3. The method of claim 1, wherein the thrombolytic agent is human single chain tissue plasminogen activator (tPA) and the low amount is about 75 ng/ml.

4. The method of claim 1, wherein the thrombolytic agent is human single chain tissue plasminogen activator (tPA) and the high amount is about 150 ng/ml.

5. The method of claim 1, wherein the viscoelastic assay is performed using a container containing the thrombolytic agent on an interior of the container.

6. The method of claim 5, wherein the assay is performed using the container and a pin, wherein the pin moves relative to the container or wherein the container moves relative to the pin.

7. The method of claim 1, wherein the coagulation characteristic value is a LY30 value.

8. The method of claim 1, wherein the patient is a human or a non-human animal.

9. The method of claim 1, wherein the patient has or is undergoing a condition selected from the group consisting of surgery, a disease condition, a critical illness, trauma, bleeding, and a thromboembolic event.

10. The method of claim 1, wherein the patient identified as having hyperfibrinolysis is administered a therapeutically relevant amount of a therapeutic agent that strengthens a blood clot or slows the dissolution of a blood clot.

11. The method of claim 10, wherein the therapeutic agent that strengthens a blood clot or slows the dissolution of a blood clot is selected from the group consisting of an antifibrinolytic agent, whole blood, blood plasma, cryoprecipitate, factor XIII, fibrinogen and other specific clotting factor concentrates.

12. The method of claim 1, wherein the patient identified as having fibrinolysis shutdown is administered a therapeutically relevant amount of a therapeutic agent that weakens a blood clot or speeds the dissolution of a blood clot.

13. The method of claim 12, wherein the therapeutic agent that weakens a blood clot or speeds the dissolution of a blood clot is selected from the group consisting of aspirin, heparin, clopidogrel, warfarin, a direct thrombin inhibitor, a Factor Xa inhibitor, tPA, an anticoagulant, a thrombolytic agent, an antifibrinogen agent, an anti-Factor XIII agent, a glycoprotein IIb/IIIa inhibitor, and an antiplatelet agent.

14. The method of claim 11, wherein the antifibrinolytic agent is selected from the group consisting of tranexamic acid, aminocaproic acid and aprotinin.

15. The method of claim 1, wherein the coagulation characteristic value is a LI30 value.

* * * * *